US011071768B2

(12) United States Patent
Ryckman et al.

(10) Patent No.: US 11,071,768 B2
(45) Date of Patent: Jul. 27, 2021

(54) CASPOFUNGIN COMPOSITIONS FOR INHALATION

(71) Applicant: TRILOGY THERAPEUTICS, INC., San Diego, CA (US)

(72) Inventors: David M. Ryckman, San Diego, CA (US); Iching G. Yu, San Diego, CA (US)

(73) Assignee: TRILOGY THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/425,458

(22) Filed: May 29, 2019

(65) Prior Publication Data

US 2019/0307837 A1 Oct. 10, 2019

Related U.S. Application Data

(63) Continuation of application No. PCT/US2019/017520, filed on Feb. 11, 2019.

(60) Provisional application No. 62/629,471, filed on Feb. 12, 2018.

(51) Int. Cl.
| | | |
|---|---|---|
| *A61K 38/12* | (2006.01) | |
| *A61K 9/00* | (2006.01) | |
| *A61K 9/19* | (2006.01) | |
| *A61P 11/00* | (2006.01) | |
| *A61K 47/02* | (2006.01) | |
| *A61P 31/10* | (2006.01) | |
| *A61K 47/32* | (2006.01) | |

(52) U.S. Cl.
CPC ............ *A61K 38/12* (2013.01); *A61K 9/0073* (2013.01); *A61K 9/19* (2013.01); *A61K 47/02* (2013.01); *A61K 47/32* (2013.01); *A61P 11/00* (2018.01); *A61P 31/10* (2018.01)

(58) Field of Classification Search
CPC .................................................... A61K 38/12
See application file for complete search history.

(56) References Cited

U.S. PATENT DOCUMENTS

| | | |
|---|---|---|
| 4,496,086 A | 1/1985 | Duchadeau |
| 5,280,784 A | 1/1994 | Koehler |
| 5,309,900 A | 5/1994 | Knoch et al. |
| 5,312,046 A | 5/1994 | Knoch et al. |
| 5,378,804 A | 1/1995 | Balkovec et al. |
| 5,458,136 A | 10/1995 | Jaser et al. |
| 5,461,695 A | 10/1995 | Knoch |
| 5,549,102 A | 8/1996 | Lintl et al. |
| 5,740,966 A | 4/1998 | Blaha-Schnabel |
| 5,936,062 A | 8/1999 | Leonard et al. |
| 5,952,300 A | 9/1999 | Nerurkar et al. |
| 5,957,389 A | 9/1999 | Wunderlich et al. |
| 6,000,394 A | 12/1999 | Blaha-Schnabel et al. |
| 6,085,741 A | 7/2000 | Becker |
| 6,176,237 B1 | 1/2001 | Wunderlich et al. |
| 6,513,519 B2 | 2/2003 | Gallem |
| 6,513,727 B1 | 2/2003 | Jaser et al. |
| 8,006,698 B2 * | 8/2011 | Boehm .................. A61M 11/02 128/207.18 |
| 8,329,198 B2 | 12/2012 | Salama et al. |
| 8,481,591 B2 | 7/2013 | Sawant |
| 8,648,175 B2 | 2/2014 | Vukmirovic et al. |
| 9,636,407 B2 | 5/2017 | Jiang et al. |
| 2005/0232981 A1 * | 10/2005 | Ben-Sasson ............ A61P 25/28 424/448 |
| 2006/0045865 A1 | 3/2006 | Jacob et al. |
| 2007/0172517 A1 * | 7/2007 | Ben-Sasson ......... A61K 9/0031 424/448 |
| 2007/0196452 A1 * | 8/2007 | Zhang .................... A61P 29/00 424/443 |
| 2007/0196453 A1 * | 8/2007 | Zhang .................. A61K 9/7015 424/443 |
| 2007/0202051 A1 * | 8/2007 | Schuschnig .......... A61K 9/0043 424/45 |
| 2008/0159984 A1 * | 7/2008 | Ben-Sasson ......... A61K 38/212 424/85.7 |
| 2009/0170753 A1 | 7/2009 | Welz et al. |
| 2010/0137197 A1 | 6/2010 | Mittal et al. |
| 2011/0081411 A1 * | 4/2011 | Perrett ...................... A61P 1/04 424/451 |
| 2011/0142889 A1 * | 6/2011 | Lee ........................ A61K 38/09 424/400 |
| 2011/0182997 A1 * | 7/2011 | Lewis .................... A61K 9/008 424/490 |
| 2011/0190245 A1 * | 8/2011 | Rundfeldt ............ A61K 31/496 514/171 |
| 2011/0281788 A1 * | 11/2011 | Coote .................... A61K 38/12 514/3.4 |

(Continued)

FOREIGN PATENT DOCUMENTS

| | | |
|---|---|---|
| EP | 2248518 B1 | 1/2013 |
| WO | WO-2019157453 A1 | 8/2019 |

OTHER PUBLICATIONS

Wong-Beringer et al., 2005, Suitability of Caspofungin for Aerosol Delivery, Chest, 128(5): 3711-3716.*
Kaneda et al., 2004, The use of PVP as a polymeric carrier to improve the plasma half-life of drugs, Biomaterials, 25: 3259-3266.*
Mu et al., 1999, Bioconjugation of Laminin-Related Peptide YIGSR with Polyvinyl Pyrrolidone Increases Its Antimetastatic Effect Due to a Longer Plasma Half-Life, Biochemical and Biophysical Research Communications, 264: 763-767.*
Berge et al. Pharmaceutical Salts. Journal of Pharmaceutical Sciences 66(1):1-19 (Jan. 1977).
Cicogna et al. Efficacy of prophylactic aerosol amphotericin B lipid complex in a rat model of pulmonary aspergillosis. Antimicrob Agents Chemother 41(2):259-261 (1997).

(Continued)

*Primary Examiner* — Amber D Steele
(74) *Attorney, Agent, or Firm* — Wilson Sonsini Goodrich & Rosati

(57) ABSTRACT

Compositions and corresponding methods for the treatment and/or prevention of a fungal infection in the pulmonary system of a subject in need thereof with caspofungin or a derivative thereof are disclosed herein.

23 Claims, 11 Drawing Sheets

(56) References Cited

U.S. PATENT DOCUMENTS

| | | | |
|---|---|---|---|
| 2012/0093886 A1* | 4/2012 | Salama | A61P 1/04 424/400 |
| 2012/0108527 A1* | 5/2012 | Sawant | A61K 31/351 514/24 |
| 2012/0251594 A1* | 10/2012 | Longest | A61P 25/24 424/400 |
| 2012/0301517 A1* | 11/2012 | Zhang | A61K 31/473 424/400 |
| 2013/0022564 A1* | 1/2013 | Zhang | A61K 47/18 424/61 |
| 2013/0142879 A1* | 6/2013 | Lewis | A61K 31/00 424/490 |
| 2013/0217777 A1* | 8/2013 | Kirkorian | A61K 9/16 514/630 |
| 2014/0147506 A1* | 5/2014 | Longest | A61K 9/12 424/489 |
| 2015/0031631 A1* | 1/2015 | Mamluk | A61P 3/00 514/21.1 |
| 2017/0348378 A1 | 12/2017 | Ryckman et al. | |

OTHER PUBLICATIONS

Damle et al. Pharmacokinetics and Tissue Distribution of Anidulafungin in Rats. Antimicrob. Agents Chemo 52:2673-2676 (2008).

Espinel-Ingroff et al. Wild-Type MIC Distributions and Epidemiological Cutoff Values for Amphotericin B and *Aspergillus* spp. for the CLSI Broth Microdilution Method (M38-A2 Document). Antimicrob Agents Chemo 55(6):2855-2858 (2011).

Hadju et al. Preliminary Animal Pharmacokinetics of the Parenteral Antifungal Agent MK-0991 (L-743,872). Antimicrob. Agents Chemo 41(11):2339-2344 (1997).

Niwa et al. Tissue Distribution after Intravenous Dosing of Micafungin, an Antifungal Drug, to Rats. Bio Pharm Bull 27(7):1154-1156 (2004).

PCT/US2019/017520 International Search Report and Written Opinion dated Mar. 27, 2019.

Pfaller et al. Correlation of MIC with Outcome for Candida Species Tested against Caspofungin, Anidulafungin, and Micafungin: Analysis and Proposal for Interpretive MIC Breakpoints. J Clin Microbiol 46(8):2620-2629 (2008).

Sandhu et al. Disposition of Caspofungin, a Novel Antifungal Agent, in Mice, Rats, Rabbits, and Monkeys. Antimicrob Agents Chemo 48(4):1272-1280 (2004).

Stone et al. Disposition of Caspofungin: Role of Distribution in Determining Pharmacokinetics in Plasma. Antimicrob. Agents Chemo 48(3):815-823 (2004).

Van De Sande et al. Caspofungin prolongs survival of transiently neutropenic rats with advanced-stage invasive pulmonary aspergillosis. Antimicrob Agents Chemother 52(4):1345-1350 (2008).

Balkovec et al. Discovery and development of first in class antifungal caspofungin (*Cancidas*)—A case study. Nat Prod Rep 31(1):15-34 (2014).

Gombotz et al. The stabilization of a human IgM monoclonal antibody with poly(vinylpyrrolidone). Pharm Res 11(5):624-32 (1994).

Kaneda et al. The use of PVP as a polymeric carrier to improve the plasma half-life of drugs. Biomaterials 25:3529-3266 (2004).

Miklos et al. Volume Exclusion and Soft Interaction Effects on Protein Stability under Crowded Conditions. Biochemistry 49(33):6984-6991 (2010).

Mu et al. Bioconjugation of Laminin-Related Peptide YIGSR with Polyvinyl Pyrrolidone Increases Its Antimetastatic Effect Due to a Longer Plasma Half-Life. Biochemical and Biophysical Research Communications 264:763-767 (1999).

Papageorgiou et al. Improvement in chemical and physical stability of fluvastatin drug through hydrogen bonding interactions with different polymer matrices. Curr Drug Deliv. 6(1):101-12 (2009).

Thompson et al. A molecular design approach to peptide drug stabilization. Molecular Simulation 32:291-295 (2006).

Van De Weert et al. Chapter 4: Characterization of Therapeutic Peptides and Protein. Pharmaceutical Formulation Development of Peptides and Proteins (Hovgaard ed.) (pp. 49-78) (2012).

Wang. Advanced protein formulations. Protein Sci 24:1031-1039 (2015).

Wong-Beringer et al. Suitability of caspofungin for aerosol delivery: physicochemical profiling and nebulizer choice. Chest 128(5):3711-3716 (2005).

Yulianita et. al. Forced Degradation Study of Statins: A Review. Int J App Pharm 10:38-42 (2018).

\* cited by examiner

CASPOFUNGIN COMPOSITIONS FOR INHALATION

CROSS-REFERENCE

This application is a continuation of PCT International Application No. PCT/US2019/017520, filed Feb. 11, 2019, which claims the benefit of U.S. Provisional Application Ser. No. 62/629,471, filed Feb. 12, 2018, each of which are incorporated herein by reference in their entirety.

BACKGROUND

A pulmonary infection caused by *Aspergillus* species is a serious invasive infection that usually occurs in people with compromised immune systems due to cancer, AIDS, leukemia, an organ transplant, chemotherapy, or other conditions or medications that lower the number or function of normal white blood cells or weaken the immune system. The usual course of treatment requires the intravenous or oral use of antifungal agents.

SUMMARY OF THE DISCLOSURE

The present disclosure provides compositions comprising caspofungin and methods of generating and using the same.

In an aspect, the present disclosure provides a composition suitable for inhalation administration comprising i) caspofungin, or a polymorph, pharmaceutically acceptable salt, hydrate, or solvate thereof; and ii) polyvinylpyrrolidone (PVP).

In some embodiments, the composition is essentially free of mannitol. In some embodiments, the composition is essentially free of sugar alcohol or sugar.

In some embodiments, the pharmaceutically acceptable salt of caspofungin is the acetate salt. In some embodiments, the composition comprises from about 1 mg to about 100 mg of caspofungin acetate.

In some embodiments, the weight ratio of polyvinylpyrrolidone (PVP) to caspofungin, or the polymorph, pharmaceutically acceptable salt, hydrate, or solvate thereof, is from about 6:1 to about 1:1. In some embodiments, the weight ratio of polyvinylpyrrolidone (PVP) to caspofungin, or the polymorph, pharmaceutically acceptable salt, hydrate, or solvate thereof is about 4:1.

In some embodiments, the composition further comprises at least one stability-enhancing salt. In some embodiments, the at least one stability-enhancing salt is selected from the group consisting of sodium chloride, potassium chloride, sodium phosphate, potassium phosphate, or a combination thereof.

In some embodiments, the composition further comprises a pH modifier. In some embodiments, the pH modifier is sodium hydroxide or acetic acid.

In some embodiments, the composition has a pH of from about 5 to about 7.

In some embodiments, the composition further comprises a vehicle. In some embodiments, the vehicle is selected from the group consisting of water, saline, or phosphate-buffered saline. In some embodiments, the vehicle is saline.

In some embodiments, the composition is a pre-lyophilized composition.

In some embodiments, the composition is a lyophilized composition. In some embodiments, the composition is a lyophilized composition that has been reconstituted with water, saline, or phosphate-buffered saline (PBS) to provide a reconstituted solution. In some embodiments, the reconstituted solution comprises greater than about 95% of caspofungin, or a polymorph, pharmaceutically acceptable salt, hydrate, or solvate thereof that has not degraded after storage at about 5° C. for at least 240 hours or has not degraded after storage at about 25° C. for 7 hours.

In some embodiments, administration of the composition using an inhalation delivery device provides a lung tissue concentration of caspofungin, or the polymorph, pharmaceutically acceptable salt, hydrate, or solvate thereof, that is from about 25-fold to about 100-fold greater than intravenous administration at the same delivery dose. In some embodiments, the lung tissue concentration of caspofungin, or the polymorph, pharmaceutically acceptable salt, hydrate, or solvate thereof, administered using the inhalation delivery device is greater than intravenous administration at the same delivery dose for about 0.5 hour to about 168 hours.

In some embodiments, administration of the composition provides a concentration of caspofungin, or the polymorph, pharmaceutically acceptable salt, hydrate, or solvate thereof, in the lung that is from about 5-fold greater to about 1000-fold greater than a concentration of caspofungin, or the polymorph, pharmaceutically acceptable salt, hydrate, or solvate thereof, in the liver, kidney, or plasma. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 0.5 hour to about 168 hours.

In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 3 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 168 hours after administration. In some embodiments, the minimum inhibitory concentration (MIC) or the minimum effective concentration (MEC) is from about 0.001 µg/mL to about 32 µg/mL.

In some embodiments, the composition is formulated for administration with an inhalation device selected from a jet nebulizer, ultrasonic wave nebulizer, high efficiency nebulizer, heat vaporizer, soft mist inhaler, thermal aerosol inhaler, or electrohydrodynamic-based solution misting inhaler.

In some embodiments, the half-life of the caspofungin, or a polymorph, pharmaceutically acceptable salt, hydrate, or solvate thereof, in the lung is about 24 hours to about 50 hours.

In some embodiments, the composition provides an increase of greater than about 50% of caspofungin, or a polymorph, pharmaceutically acceptable salt, hydrate, or solvate thereof, deposit in the lung without increasing systemic exposure when compared to a composition that does not comprise polyvinylpyrrolidone (PVP).

In some embodiments, the composition comprises greater than about 95% of caspofungin, or a polymorph, pharmaceutically acceptable salt, hydrate, or solvate thereof that has not degraded after storage at about −20° C., 5° C., or 25° C. for about 0 weeks, about 2 weeks, about 4 weeks, about 8 weeks, about 12 weeks or about 52 weeks.

In some embodiments, the composition consists essentially of (i) caspofungin, or a polymorph, pharmaceutically acceptable salt, hydrate, or solvate thereof, and (ii) polyvinylpyrrolidone (PVP).

The present disclosure also provides a method of preventing or treating a fungal infection in the pulmonary system of a subject in need thereof comprising administering to the subject a composition as described above. In some embodiments, the method is for treating or preventing a fungal infection caused by *Candida* sp., *Aspergillus* sp., and/or *Pneumocystis jirovecii*.

In another aspect, the present disclosure also provides a composition suitable for inhalation administration comprising
- i) caspofungin, or a polymorph, pharmaceutically acceptable salt, hydrate, or solvate thereof;
- ii) polyvinylpyrrolidone (PVP); and
- iii) at least one stability-enhancing salt.

In some embodiments, the at least one stability-enhancing salt is sodium chloride, potassium chloride, or a combination thereof. In some embodiments, the at least one stability-enhancing salt further comprises sodium phosphate, potassium phosphate, or a combination thereof. In some embodiments, the sodium phosphate is disodium hydrogen phosphate, and the potassium phosphate is potassium dihydrogen phosphate.

Provided in another aspect is a composition suitable for inhalation administration comprising
- i) caspofungin, or a polymorph, pharmaceutically acceptable salt, hydrate, or solvate thereof; and
- ii) polyvinylpyrrolidone (PVP);

wherein the composition comprises greater than about 95% of caspofungin, or a polymorph, pharmaceutically acceptable salt, hydrate, or solvate thereof that has not degraded after storage at about −20° C., 5° C., or 25° C. for about 0 weeks, about 2 weeks, about 4 weeks, about 8 weeks, about 12 weeks, about 24 weeks or about 52 weeks.

Provided in another aspect is a composition suitable for inhalation administration comprising
- i) caspofungin, or a polymorph, pharmaceutically acceptable salt, hydrate, or solvate thereof; and
- ii) polyvinylpyrrolidone (PVP);

wherein the composition is a lyophilized composition that comprises less than about 2% by weight of water.

Provided in another aspect is a composition suitable for inhalation administration comprising
- i) caspofungin, or a polymorph, pharmaceutically acceptable salt, hydrate, or solvate thereof; and
- ii) polyvinylpyrrolidone (PVP);

wherein the concentration of caspofungin, or the polymorph, pharmaceutically acceptable salt, hydrate, or solvate thereof, in a lung is greater than about 8 μg/g for about 0.5 hour to about 24 hours.

In some embodiments, the concentration of caspofungin, or the polymorph, pharmaceutically acceptable salt, hydrate, or solvate thereof, in the lung is greater than about 16 μg/g for about 0.5 hour to about 2 hours.

Provided in another aspect is a composition suitable for inhalation administration comprising
- i) caspofungin, or a polymorph, pharmaceutically acceptable salt, hydrate, or solvate thereof; and
- ii) polyvinylpyrrolidone (PVP).

In some embodiments, the composition is essentially free of mannitol. In some embodiments, the composition is essentially free of sugar alcohol. In some embodiments, the composition is essentially free of sugar alcohol or sugar.

In some embodiments, the pharmaceutically acceptable salt of caspofungin is the acetate salt. In some embodiments, the composition comprises from about 1 mg to about 100 mg of caspofungin acetate.

In some embodiments, the weight ratio of polyvinylpyrrolidone (PVP) to caspofungin, or the polymorph, pharmaceutically acceptable salt, hydrate, or solvate thereof, is from about 10:1 to about 1:1. In some embodiments, the weight ratio of polyvinylpyrrolidone (PVP) to caspofungin, or the polymorph, pharmaceutically acceptable salt, hydrate, or solvate thereof is about 6:1 about 4:1, about 2:1, or about 1:1.

In some embodiments, the composition further comprises at least one stability-enhancing salt. In some embodiments, the at least one stability-enhancing salt is sodium chloride, potassium chloride, or a combination thereof. In some embodiments, the at least one stability-enhancing salt further comprises sodium phosphate, potassium phosphate, or a combination thereof. In some embodiments, the sodium phosphate is disodium hydrogen phosphate, and the potassium phosphate is potassium dihydrogen phosphate.

In some embodiments, the composition further comprises a pH modifier. In some embodiments, the pH modifier is sodium hydroxide or acetic acid. In some embodiments, the composition has a pH of from about 5 to about 7. In some embodiments, the composition has a pH of about 6. In some embodiments, the composition further comprises a vehicle. In some embodiments, the vehicle is buffered. In some embodiments, the vehicle is water, saline, or phosphate-buffered saline. In some embodiments, the vehicle has a volume of from about 0.1 mL to about 3 mL. In some embodiments, the composition is a pre-lyophilized composition. In some embodiments, the pre-lyophilized composition is sterilized by filtration. In some embodiments, the composition is a lyophilized composition. In some embodiments, the lyophilized composition comprises less than about 2% by weight of water. In some embodiments, the lyophilized composition is reconstituted with water, saline, or phosphate-buffered saline (PBS) to provide a reconstituted solution. In some embodiments, the reconstituted solution comprises greater than about 95% of caspofungin, or a polymorph, pharmaceutically acceptable salt, hydrate, or solvate thereof that has not degraded after storage at about 5° C., or 25° C. for about 0 hours, about 1 hours, about 4 hours, about 7 hours, about 24 hours, about 72 hours, about 96 hours, about 1 week, or about 10 days In some embodiments, the administration of the composition provides a lung tissue concentration of caspofungin, or the polymorph, pharmaceutically acceptable salt, hydrate, or solvate thereof, that is from about 1-fold to about 100-fold greater than intravenous administration at the same delivery dose. In some embodiments, the lung tissue concentration of caspofungin, or the polymorph, pharmaceutically acceptable salt, hydrate, or solvate thereof, is greater than intravenous administration at the same delivery dose for about 0.5 hour to about 168 hours. In some embodiments, the administration of the composition provides a lung tissue concentration of caspofungin, or the polymorph, pharmaceutically acceptable salt, hydrate, or solvate thereof, that is from about 1-fold to about 50-fold greater than intravenous administration at the same delivery dose. In some embodiments, the lung tissue concentration of caspofungin, or the polymorph, pharmaceutically acceptable salt, hydrate, or solvate thereof, is greater than intravenous administration at the same delivery dose for about 0.5 hour to about 168 hours. In some embodiments, the administration of the composition provides a concentration of caspofungin, or the polymorph, pharmaceutically acceptable salt, hydrate, or solvate thereof, in the lung that is from about 1-fold greater to about 1000-fold greater than a concentration of caspofungin, or the polymorph, pharmaceutically acceptable salt, hydrate, or solvate thereof, in the liver, kidney, or plasma. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 0.5 hour to about 168 hours. In some embodiments, the administration of the composition provides a concentration of caspofungin, or the polymorph, pharmaceutically acceptable salt, hydrate, or solvate thereof, in the lung that is from about 1-fold greater to about 350-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 150-fold greater than a concentration of caspofungin, or the polymorph, pharmaceutically acceptable salt, hydrate, or solvate thereof, in the liver, kidney, or plasma. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 0.5 hour to about 168 hours.

In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 3 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 12 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 24 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 48 hours after administration. the concentration of caspofungin, or the polymorph, pharmaceutically acceptable salt, hydrate, or solvate thereof, in the lung is above the minimum inhibitory concentration (MIC) or the minimum effective concentration (MEC) for about 72 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 96 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 120 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 144 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 168 hours after administration. In some embodiments, the minimum inhibitory concentration (MIC) is from about 0.001 μg/mL to about 128 μg/mL. In some embodiments, the minimum inhibitory concentration (MIC) is from about 0.001 μg/mL to about 32 μg/mL. In some embodiments, the minimum effective concentration (MEC) is from about 0.001 μg/mL to about 128 μg/mL. In some embodiments, the minimum inhibitory concentration (MEC) is from about 0.001 μg/mL to about 32 μg/mL.

In some embodiments, the concentration of caspofungin, or the polymorph, pharmaceutically acceptable salt, hydrate, or solvate thereof, in the lung is greater than about 8 μg/g for about 0.5 hour to about 24 hours. In some embodiments, the concentration of caspofungin, or the polymorph, pharmaceutically acceptable salt, hydrate, or solvate thereof, in the lung is greater than about 16 μg/g for about 0.5 hour to about 2 hours.

In some embodiments, the composition is administered with an inhalation device selected from a jet nebulizer, ultrasonic wave nebulizer, high efficiency nebulizer, heat vaporizer, soft mist inhaler, thermal aerosol inhaler, or electrohydrodynamic-based solution misting inhaler. In some embodiments, the composition is administered by the inhalation device as droplets or particles having a mass median aerodynamic diameter (MMAD) from about 0.1 μm to about 10 μm. In some embodiments, the composition is administered by the inhalation device as droplets or particles having a mass median aerodynamic diameter (MMAD) from about 0.1 μm to about 5 μm. In some embodiments, the droplets or particles have a geometric standard deviation (GSD) from about 2.0 to about 6.0.

In some embodiments, the half-life of the caspofungin, or a polymorph, pharmaceutically acceptable salt, hydrate, or solvate thereof, in the lung is about 1 hour to about 50 hours. In some embodiments, the half-life of the caspofungin, or a polymorph, pharmaceutically acceptable salt, hydrate, or solvate thereof, in the lung is about 20 hours to about 50 hours. In some embodiments, the composition is stable from about −20° C. to about 25° C. In some embodiments, the composition is stable at about −20° C., about 5° C., or about 25° C. In some embodiments, the composition is stable for at least about 3 months to about 2 years. In some embodiments, the composition is stable for at least about 1 year. In some embodiments, the composition comprises greater than about 95% of caspofungin, or a polymorph, pharmaceutically acceptable salt, hydrate, or solvate thereof, that has not degraded after storage at about −20° C. for about 0 weeks, about 2 weeks, about 4 weeks, about 8 weeks, about 12 weeks, about 24 weeks or about 52 weeks. In some embodiments, the composition comprises greater than about 95% of caspofungin, or a polymorph, pharmaceutically acceptable salt, hydrate, or solvate thereof, that has not degraded after storage at about 5° C. for about 0 weeks, about 2 weeks, about 4 weeks, about 8 weeks, about 12 weeks, about 24 weeks or about 52 weeks. In some embodiments, the composition comprises greater than about 95% caspofungin, or a polymorph, pharmaceutically acceptable salt, hydrate, or solvate thereof, that has not degraded after storage at about 25° C. after about 0 weeks, about 2 weeks, about 4 weeks, about 8 weeks, about 12 weeks, about 24 weeks or about 52 weeks. In some embodiments, the composition provides an increase of greater than 50% of caspofungin, or a polymorph, pharmaceutically acceptable salt, hydrate, or solvate thereof, deposit in the lung without increasing systemic exposure when compared to a composition that does not comprise polyvinylpyrrolidone (PVP).

Also provided herein in one aspect is a method of preventing or treating a fungal infection in the pulmonary system of a subject in need thereof comprising administering to the subject any one of the composition described herein. In some embodiments, the method is for treating a fungal infection caused by *Candida* sp., and/or by *Aspergillus* sp., and/or by *Pneumocystis jirovecii*. In some embodiments, the method is for preventing a fungal infection caused by *Candida* sp., and/or by *Aspergillus* sp., and/or by *Pneumocystis jirovecii*.

Provided herein in another aspect is a kit comprising:
 a) a first container comprising a solid composition suitable for inhalation administration, wherein the composition comprises i) caspofungin, or a polymorph, pharmaceutically acceptable salt, hydrate, or solvate thereof, and ii) polyvinylpyrrolidone (PVP); and
 b) a second container comprising a solution for reconstituting the solid composition.

In some embodiments, the kit further comprises an inhalation device. In some embodiments, the solid composition suitable for inhalation administration is a lyophilized composition. In some embodiments, the solution for reconstituting the solid composition is water, saline or phosphate-buffered saline (PBS).

Provided in another aspect is a method for preparing a composition suitable for inhalation administration comprising
 a) forming a liquid solution comprising i) caspofungin, or a polymorph, pharmaceutically acceptable salt, hydrate, or solvate thereof; ii) polyvinylpyrrolidone (PVP); iii) a vehicle; and iv) optionally, a pH modifying agent to form a pre-lyophilized solution; and
 b) lyophilizing the pre-lyophilized solution to provide the composition suitable for inhalation administration.

In some embodiments, the pre-lyophilized solution from step a) is sterilized by filtration.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Figure 1A:
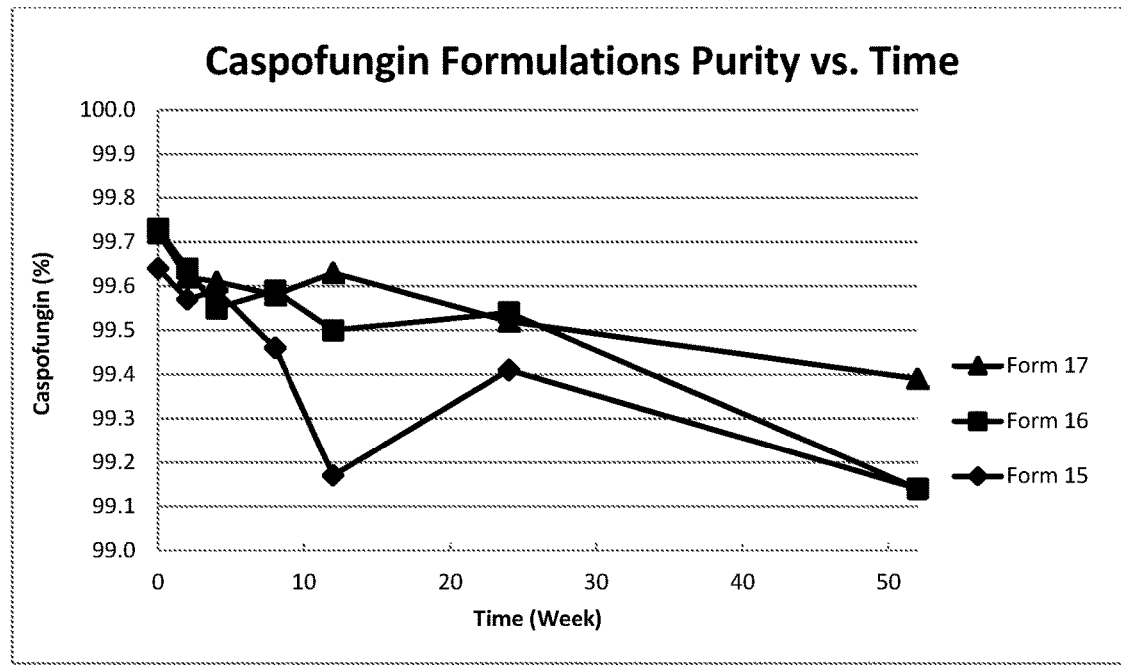
FIG. 1A shows the total caspofungin (%) following storage at 5° C. as determined by HPLC for formulations 15, 16, and 17.

While preferred embodiments of the present disclosure have been shown and described herein, it will be obvious to those skilled in the art that such embodiments are provided by way of example only. Numerous variations, changes, and substitutions will now occur to those skilled in the art without departing from the present disclosure. It should be understood that various alternatives to the embodiments of the present disclosure described herein are employed in some instances. It is intended that the following claims define the scope of the present disclosure and that methods and structures within the scope of these claims and their equivalents be covered thereby.

Unless defined otherwise, all technical and scientific terms used herein have the same meaning as commonly understood by one of skill in the art to which the present disclosure described herein belong. All publications, patents, and patent applications mentioned in this specification are hereby incorporated by reference to the same extent as if each individual publication, patent, or patent application was specifically and individually indicated to be incorporated by reference.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference for such disclosure.

Pulmonary fungal infections are serious infections that usually occur in patients with compromised immune systems and lead to significant mortality and morbidity in such patients. The standard course of treatment requires the administration of antifungal agents intravenously or orally; however, such systemic delivery is associated with numerous side effects, ranging from phlebitis at the infusion site and chills to renal toxicity. The aerosolized delivery of antifungal agents is an attractive alternative for the prevention and treatment of pulmonary fungal lung infections because it allows for the concentrated delivery of the antifungal agent directly to the site of infection with minimal systemic exposure, thus limiting the potential side effects usually associated with intravenous delivery.

The antifungal agent caspofungin is an attractive candidate for aerosolized antifungal therapy. Caspofungin, a macrocyclic lipopeptide, is a member of a class of antifungal agents known as echinocandins, which inhibit the synthesis of glucan in the fungal cell wall through the noncompetitive inhibition of 1,3-β glucan synthesis. Caspofungin has significant activity against fungal infections caused by the *Candida* species, *Aspergillus* species and *Pneumocystis carinii* pneumonia. Furthermore, caspofungin is relatively less toxic than other antifungal agents that are commonly employed for anti-fungal treatment, such as amphotericin B. Despite these advantages, there are no commercially available aerosol formulations of caspofungin for the prevention and/or treatment of antifungal infections.

The commercial formulation of caspofungin is a lyophilized, diacetate salt containing sucrose, mannitol, glacial acetic acid and sodium hydroxide and is reconstituted for intravenous use. Sold by Merck & Company, Inc under the trade name Cancidas®, caspofungin is the first member of the echinocandins to receive US Food and Drug Administration approval and has been approved for the treatment of invasive aspergillosis in patients who are refractory to or intolerant of other therapies; the empirical therapy for presumed fungal infections in febrile, neutropenic patients; the treatment of candidemia; intra-abdominal abscesses, peritonitis and pleural space infections caused by *Candida* infections, and the treatment of esophageal candidiasis.

One challenge in administering caspofungin is that caspofungin is unstable and prone to degradation, especially at room temperature (~25° C.). As such, caspofungin is stored under low temperatures (e.g. 2-8° C.) and is used within 1 hour after reconstitution. There have been various efforts at developing caspofungin formulations with improved stability. The development of the acetate salt of caspofungin, which led to the formulation of Cancidas®, was an improvement over earlier formulations that used the tartrate salt (U.S. Pat. No. 5,952,300). Another example include a formulation that eliminated the acetic acid and sodium hydroxide present in Cancidas® as pH modifiers, wherein the lyophilized and reconstituted formulations demonstrated improved stabilities at 25° C. when compared to the other formulations of caspofungin (U.S. Patent Publication 2009/0170753). In another example, a non-reducible sugar, such as trehalose, was used to replace the sucrose and mannitol present in the Cancidas® to provide formulations that have improved storage stability (US Patent Publication 2010/0137197).

Described herein are compositions for inhalation administration comprising caspofungin, or a polymorph, pharmaceutically acceptable salt, hydrate, or solvate thereof, and polyvinylpyrrolidone (PVP). These compositions are useful for treating and/or preventing fungal infections in the pulmonary system in a subject in need thereof. In some embodiments, the composition is essentially free of mannitol. In some embodiments, the composition is essentially free of sugar alcohol. In some embodiments, the composition is essentially free of sugar alcohol or sugar. The compositions described herein allow for the localized and concentrated delivery the caspofungin, or a polymorph, pharmaceutically acceptable salt, hydrate, or solvate thereof, directly to the site of infection, such as the pulmonary tissues, while minimizing the systemic exposure of caspofungin, or a polymorph, pharmaceutically acceptable salt, hydrate, or solvate thereof, to other organs. In some embodiments, the compositions described herein that comprise polyvinylpyrrolidone also allow for greater localized and concentrated delivery the caspofungin, or a polymorph, pharmaceutically acceptable salt, hydrate, or solvate thereof, directly to the site of infection, such as the pulmonary tissues, when compared to compositions that do not comprise polyvinylpyrrolidone. In some embodiments, the compositions described herein provides improved caspofungin, or a polymorph, pharmaceutically acceptable salt, hydrate, or solvate thereof, retention in the lung when compared to compositions that do not comprise polyvinylpyrrolidone. It is also recognized herein that, in some embodiments, the addition of stability-enhancing salts, such as chloride salts or phosphate salts, to the compositions described herein provide compositions that are stable under storage conditions. In some embodiments, the compositions described herein exhibit improved stability under appropriate storage conditions.

Echinocandin Tissue Distribution

There are three echinocandins approved for antifungal therapy: caspofungin, micafungin and anidulafungin. All of these compounds are active against a similar range of fungi and are structurally very similar as they are chemically close analogs. Despite their structural similarities it is recognized herein that their distribution and disposition in animals and humans are markedly different and not predictable. For instance, in rat studies, anidulafungin rapidly distributes into tissues to achieve peak concentrations within 30 min and maintains levels above MICs for common pathogens over 72 hours. Furthermore anidulafungin exposure is 9-12 fold higher in tissues susceptible to fungal infection, such as the liver, lung, spleen, kidney, than in plasma (Damle et al., Pharmacokinetics and Tissue Distribution of Anidulafungin in Rats, Antimicrob. Agents Chemo., 2008, 52, 7, p 2673-2676). In contrast, in rat studies, micafungin distributes moderately into the liver, kidney, and lungs, and the tissue concentrations decrease in parallel with micafungin in plasma. Micafungin exposures in the liver, kidney, and lung are 1.6, 3.4, and 2.9 fold higher, respectively, than that for plasma (Niwa et al., Tissue Distribution after Intravenous Dosing of Micafungin, an Antifungal Drug, to Rats. *Bio Pharm Bull,* 2004, 27, 7, p 1154-1156). It is clear from these studies that tissue/plasma ratios and, thus, the overall tissue penetration for micafungin is considerably less than that observed with anidulafungin.

Caspofungin's tissue distribution has also been examined in non-human species using radiolabeled compound caspofungin (Hadju et al., Preliminary Animal Pharmacokinetics of the Parenteral Antifungal Agent MK-0991 (L-743,872), *Antimicrob. Agents Chemo.*, 1997, 41, 11, p 2339-2344; Stone et. al, Disposition of Caspofungin: Role of Distribution in Determining Pharmacokinetics in Plasma, *Antimicrob. Agents Chemo.*, 2004, 48, 3, p 815-823; and Sandhu et al., Disposition of Caspofungin, a Novel Antifungal Agent, in Mice, Rats, Rabbits, and Monkeys, *Antimicrob. Agents Chemo.*, 2004, 48, 4, p 1272-1280). However, the use of radiolabeled material enables the detection of both parent compound and labeled metabolites, but not the ability to distinguish between them. As such, the reported quantitation of caspofungin may be all caspofungin, all metabolites or an unknown mix of the two with the final case being the most likely scenario. Caspofungin levels in plasma (but not other tissues) were also analyzed for parent compound by Sandhu in 2004. The most complete analysis of caspofungin tissue distribution was published by Stone in 2004 also using radiolabeled material. Comparing Stone's reported radioactive plasma distribution with Sandhu's analysis of the parent compound in plasma it is clear that the parent compound could be 17%, 24%, or even 49% of the reported radiolabeled amount. From these studies, it is clear that the tissue distribution of caspofungin has not been determined and is not predictable from comparisons with other echinocandins.

Disclosed herein are tissue distribution studies of caspofungin via intravenous and inhalation administration. The lung retention and tissue distribution characteristics of caspofungin upon inhaled delivery are also reported herein.

Definition of Terms

Unless defined otherwise, all technical and scientific terms used herein have the same meaning as is commonly understood by one of skill in the art to which the claimed subject matter belongs. In the event that there is a plurality of definitions for terms herein, those in this section prevail.

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a", "an" and "the" include plural referents unless the context clearly dictates otherwise. It should also be noted that use of "or" means "and/or" unless stated otherwise. Furthermore, use of the term "including" as well as other forms, such as "include", "includes", and "included" is not limiting.

As used herein, the term "about" is used synonymously with the term "approximately." Illustratively, the use of the term "about" with regard to a certain therapeutically effective pharmaceutical dose indicates that values slightly outside the cited values, e.g., plus or minus 0.1% to 10%, or plus or minus 0.1% to 20%, are also effective and safe.

As used herein, the phrase "consisting essentially of" is a transitional phrase used in a claim to indicate that the following list of ingredients, parts or process steps must be present in the claimed composition, machine or process, but that the claim is open to unlisted ingredients, parts or process steps that do not materially affect the basic and novel properties of the present disclosure.

The term "prophylaxis" refers to administration of an active pharmaceutical ingredient to a patient with the purpose of reducing the occurrence or recurrence of one or more acute symptoms associated with a disease state or a condition in the patient. In the present context, prophylaxis entails administering caspofungin or the pharmaceutically acceptable salt thereof to a patient via any route of administration disclosed herein. Thus, prophylaxis includes reduction in the occurrence or recurrence rate of a disorder. However, prophylaxis is not intended to include complete prevention of onset of a disease state or a condition in a patient who has not previously been identified as suffering from the disease or the condition.

As used herein, a difference is "significant" if a person skilled in the art would recognize that the difference is probably real. In some embodiments, significance may be determined statistically, in which case two measured parameters may be referred to as statistically significant. In some embodiments, statistical significance may be quantified in terms of a stated confidence interval (CI), e.g., greater than 90%, greater than 95%, greater than 98%, etc. In some embodiments, statistical significance may be quantified in terms of a p value, e.g., less than 0.5, less than 0.1, less than 0.05, etc. The person skilled in the art will recognize these expressions of significance and will know how to apply them appropriately to the specific parameters that are being compared.

The term "patient", "subject" or "individual" are used interchangeably. As used herein, they refer to individuals suffering from a disorder, and the like, encompasses mammals and non-mammals. None of the terms require that the individual be under the care and/or supervision of a medical professional. Mammals are any member of the Mammalian class, including but not limited to humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In some embodiments of the methods and compositions provided herein, the individual is a mammal. In some embodiments, the individual is a human.

The terms "treat," "treating" or "treatment," and other grammatical equivalents as used herein, include alleviating, abating or ameliorating a disease or condition or one or more symptoms thereof, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the individual, notwithstanding that the individual is still be afflicted with the underlying disorder. For prophylactic benefit, the compositions are administered to an individual at risk of developing a particular disease, or to an individual reporting one or more of the physiological symptoms of a disease, even though a diagnosis of this disease has not been made.

The terms "administer," "administering", "administration," and the like, as used herein, refer to the methods that may be used to enable delivery of compounds or compositions to the desired site of biological action. These methods include, but are not limited to inhalation routes, oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In preferred embodiments, the compounds and compositions described herein are administered via inhalation.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount may differ from one individual to another. An appropriate "effective" amount in any individual case may be determined using techniques, such as a dose escalation study.

The term "acceptable" as used herein, with respect to a formulation, composition or ingredient, means having no persistent detrimental effect on the general health of the individual being treated.

The term "minimum inhibitory concentration" or MIC as used herein, refers to the lowest concentration of an antifungal agent that will inhibit the visible growth of a microorganism after overnight incubation.

The term "minimum effective concentration" or MEC as used herein, refers to the lowest concentration of an antifungal agent that causes abnormal hyphal growth, which is characterized by short abundant branchings.

The term "pharmaceutically acceptable" as used herein, refers to a material, such as a carrier or diluent, which does not abrogate the biological activity or properties of the compounds described herein, and is relatively nontoxic, i.e., the material may be administered to an individual without causing undesirable biological effects or interacting in a deleterious manner with any of the components of the composition in which it is contained.

The term "pharmaceutically acceptable salt" as used herein, refers to salts that retain the biological effectiveness of the free acids and bases of the specified compound and that are not biologically or otherwise undesirable. Compounds described herein may possess acidic or basic groups and therefore may react with any of a number of inorganic or organic bases, and inorganic and organic acids, to form a pharmaceutically acceptable salt. These salts can be prepared in situ during the final isolation and purification of the compounds of the present disclosure, or by separately reacting a purified compound in its free base form with a suitable organic or inorganic acid, and isolating the salt thus formed.

The term "polyvinylpyrrolidone" or "PVP", also known as polyvidone or povidone, is a water-soluble polymer made from the monomer N-vinylpyrrolidone.

The term "stability-enhancing salt" refers to a salt that provides an improvement in composition stability when compared to a similar composition that does not contain such salt. In some instances, a composition with at least one stability-enhancing salt has minimal degradation of the active pharmaceutical ingredient, such as caspofungin, after storage. Examples of suitable stability-enhancing salts include, but are not limited to, chloride salts, such as sodium chloride, potassium chloride, or a combination thereof, or phosphate salts, such as disodium hydrogen phosphate, potassium dihydrogen phosphate, or a combination thereof.

Caspofungin

As used herein, caspofungin (CAS 162808-62-0) refers to the compound of the following structure:

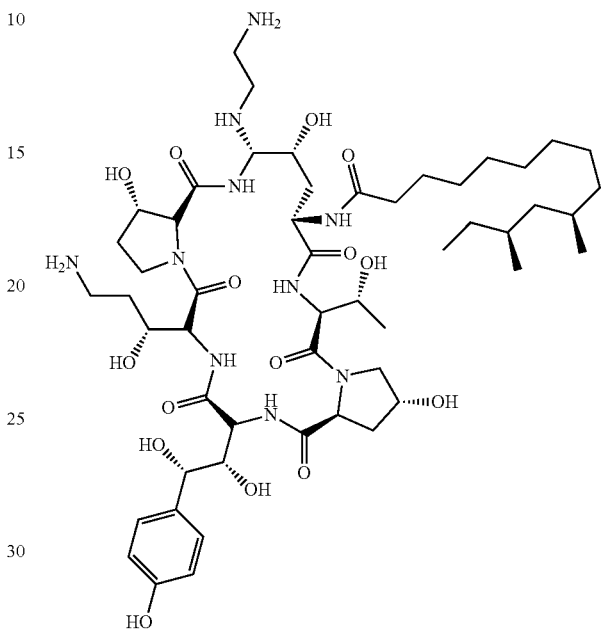

Pharmaceutically Acceptable Salts

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, Handbook of Pharmaceutical Salts: Properties, Selection and Use, Weinheim/Zürich:Wiley-VCHNHCA, 2002.

In some embodiments, the compounds described herein exist as their pharmaceutically acceptable salts. In some embodiments, the compositions disclosed herein include compositions comprising such pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the present disclosure, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate, and xylenesulfonate.

Further, in some embodiments, the compounds described herein are prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, Q-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. In some embodiments, other acids, such as oxalic, while not in themselves pharmaceutically acceptable, are employed in the preparation of salts useful as intermediates in obtaining the compounds of the present disclosure and their pharmaceutically acceptable acid addition salts.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization. The compounds described herein can be prepared as pharmaceutically acceptable salts formed when an acidic proton present in the parent compound either is replaced by a metal ion, for example an alkali metal ion, an alkaline earth ion, or an aluminum ion; or coordinates with an organic base. Base addition salts can also be prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, the salt forms of the disclosed compounds can be prepared using salts of the starting materials or intermediates.

Pharmaceutically acceptable salts of caspofungin include, but are not limited to, those derived with cations, such as sodium, potassium, aluminum, calcium, lithium, magnesium, and zinc; acids, such as hydrochloric, hydrobromic, phosphoric, sulfuric, maleic, citric, tartaric, succinic, oxalic, malic, glutamic, lactic, propionic and pamoic acids; bases, such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethyl-ammonium hydroxide. Pharmaceutically acceptable salts of caspofungin include the mono-, di-, and tri-acid forms. Also included are pharmaceutically acceptable salts disclosed in U.S. Pat. Nos. 5,378,804, 5,936,062, and US 2009/0170753, which are incorporated in reference for their disclosure of such compounds.

In some embodiments, the pharmaceutically acceptable salt of caspofungin is acetate, acrylate, adipate, alginate, aspartate, benzoate, benzenesulfonate, bisulfate, bisulfate, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate. metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylate undeconate, or xylenesulfonate.

Other examples of suitable pharmaceutically acceptable salts of caspofungin include, but are not limited to, acetates, citrates, tartrates, propionates, succinates, oxalates, malates, maleates, lactates, glutamates, and pamoates. In some embodiments, the pharmaceutically acceptable salt of caspofungin is the acetate salt. In some embodiments, the pharmaceutically acceptable salt of caspofungin is the propionate salt. In some embodiments, the pharmaceutically acceptable salt of caspofungin is the lactate salt.

Solvates and Hydrates

In some embodiments, the compounds described herein exist as solvates. The present disclosure provides for compositions comprising such solvates. The present disclosure provides for methods of treating diseases by administering such solvates. The present disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Polymorphs

In some embodiments, the compounds described herein exist as polymorphs. The present disclosure provides for compositions comprising such polymorphs. The present disclosure provides for methods of treating diseases by administering such polymorphs. The present disclosure further provides for methods of treating diseases by administering such polymorphs as pharmaceutical compositions.

Thus, the compounds described herein include all their crystalline forms, known as polymorphs. Polymorphs include the different crystal packing arrangements of the same elemental composition of a compound. In certain instances, polymorphs have different X-ray diffraction patterns, infrared spectra, melting points, density, hardness, crystal shape, optical and electrical properties, stability, and solubility. In certain instances, various factors such as the recrystallization solvent, rate of crystallization, and storage temperature cause a single crystal form to dominate.

In some embodiments, compounds described herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically labeled compounds described herein, for example those with isotopes such as deuterium, i.e., $^{2}H$, can afford certain therapeutic advantages resulting from greater metabolic stability, such as, for example, increased in vivo half-life or reduced dosage requirements. In certain embodiments, caspofungin is isotopically labeled caspofungin, or a polymorph, pharmaceutically acceptable salt, hydrate, or solvate thereof.

Compositions

Provided in one aspect is a composition suitable for inhalation administration comprising i) caspofungin, or a polymorph, pharmaceutically acceptable salt, hydrate, or solvate thereof ii) polyvinylpyrrolidone (PVP); and iii) at least one stability-enhancing salt. In some embodiments, the at least one stability-enhancing salt is sodium chloride, potassium chloride, or a combination thereof. In some embodiments, the at least one stability-enhancing salt further comprises sodium phosphate, potassium phosphate, or a combination thereof. In some embodiments, the sodium phosphate is disodium hydrogen phosphate, and the potassium phosphate is potassium dihydrogen phosphate.

Provided in another aspect is a composition suitable for inhalation administration comprising i) caspofungin, or a polymorph, pharmaceutically acceptable salt, hydrate, or solvate thereof and ii) polyvinylpyrrolidone (PVP); wherein the composition comprises greater than about 95% of caspofungin, or a polymorph, pharmaceutically acceptable salt, hydrate, or solvate thereof, that has not degraded after storage at about −20° C., 5° C., or 25° C. for about 0 weeks, about 2 weeks, about 4 weeks, about 8 weeks, about 12 weeks, about 24 weeks or about 52 weeks.

Provided in another aspect is a composition suitable for inhalation administration comprising i) caspofungin, or a polymorph, pharmaceutically acceptable salt, hydrate, or solvate thereof and ii) polyvinylpyrrolidone (PVP). In some embodiments, the composition comprises greater than about 95% of caspofungin, or a polymorph, pharmaceutically acceptable salt, hydrate, or solvate thereof, that has not degraded after storage at about −20° C., 5° C., or 25° C. for about 0 weeks, about 2 weeks, about 4 weeks, about 8 weeks, about 12 weeks, about 16 weeks, about 20 weeks, about 24 weeks, about 28 weeks, about 32 weeks, about 36 weeks, about 40 weeks, about 44 weeks, about 48 weeks, about 52 weeks, about 104 weeks, about 156 weeks, or about 208 weeks. In some cases, the composition may not degrade after storage at about −20° C., 5° C., or 25° C. for about 52 weeks.

Provided in another aspect is a composition suitable for inhalation administration comprising i) caspofungin, or a polymorph, pharmaceutically acceptable salt, hydrate, or solvate thereof and ii) polyvinylpyrrolidone (PVP). In some embodiments, the composition is a lyophilized composition that comprises less than about 2% by weight of water.

Provided in another aspect is a composition suitable for inhalation administration comprising i) caspofungin, or a polymorph, pharmaceutically acceptable salt, hydrate, or solvate thereof and ii) polyvinylpyrrolidone (PVP). In some embodiments, the concentration of caspofungin, or the polymorph, pharmaceutically acceptable salt, hydrate, or solvate thereof, in a lung is greater than about 8 μg/g for about 0.5 hour to about 24 hours. In some embodiments, the concentration of caspofungin, or the polymorph, pharmaceutically acceptable salt, hydrate, or solvate thereof, in the lung is greater than about 16 μg/g for about 0.5 hour to about 2 hours.

Provided in one aspect is a composition suitable for inhalation administration comprising caspofungin, or a polymorph, pharmaceutically acceptable salt, hydrate, or solvate thereof and polyvinylpyrrolidone (PVP).

It is recognized herein that the aerosolization of the intravenous formulation of caspofungin would not be ideal for inhalation therapy as the mannitol, which is present Cancidas® as a bulking agent that is effective for forming a lyophilized cake, induces cough when inhaled and as well as sugar promotes fungal growth. In some embodiments, the composition disclosed herein is essentially free of mannitol. In some embodiments, the composition disclosed herein is essentially free of sugar alcohol. In some embodiments, composition disclosed herein is essentially free of sugar alcohol or sugar. Examples of relevant sugar alcohols include, but are not limited to, glycerol, erythritol, threitol, arabitol, xylitol, ribitol, mannitol, sorbitol, galactitol, fucitol, iditol, inositol, volemitol, isomalt, maltitol, lactitol, maltotriitol, maltotetraitol, and polyglycitol. In some embodiments, the sugar alcohol is glycerol, erythritol, arabitol, xylitol, mannitol, and sorbitol. Examples of relevant sugars include, but are not limited to, lactose, sucrose, trehalose, dextrose, dextran, and ficoll. In some embodiments, the sugar is sucrose.

In some embodiments, the composition comprises from about 0.1 mg to about 500 mg of caspofungin, or a polymorph, pharmaceutically acceptable salt, hydrate, or solvate thereof. In some embodiments, the composition comprises from about 0.1 mg to about 200 mg of caspofungin, or a polymorph, pharmaceutically acceptable salt, hydrate, or solvate thereof. In some embodiments, the composition comprises from about 0.1 mg to about 100 mg of caspofungin, or a polymorph, pharmaceutically acceptable salt, hydrate, or solvate thereof. In some embodiments, the composition comprises from about 1 mg to about 500 mg of caspofungin, or a polymorph, pharmaceutically acceptable salt, hydrate, or solvate thereof. In some embodiments, the composition comprises from about 1 mg to about 200 mg of caspofungin, or a polymorph, pharmaceutically acceptable salt, hydrate, or solvate thereof. In some embodiments, the composition comprises from about 1 mg to about 100 mg of caspofungin, or a polymorph, pharmaceutically acceptable salt, hydrate, or solvate thereof. In some embodiments, the composition comprises about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg of caspofungin, or a polymorph, pharmaceutically acceptable salt, hydrate, or solvate thereof.

In some embodiments, the compositions comprise caspofungin acetate. In some embodiments, the composition comprises from about 0.1 mg to about 500 mg of caspofungin acetate. In some embodiments, the composition comprises from about 0.1 mg to about 200 mg of caspofungin acetate. In some embodiments, the composition comprises from about 0.1 mg to about 100 mg of caspofungin acetate. In some embodiments, the composition comprises from about 1 mg to about 500 mg of caspofungin acetate. In some embodiments, the composition comprises from about 1 mg to about 200 mg of caspofungin acetate. In some embodiments, the composition comprises from about 1 mg to about 100 mg of caspofungin acetate. In some embodiments, the composition comprises about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, or about 500 mg of caspofungin acetate.

In some embodiments, the weight ratio of polyvinylpyrrolidone (PVP) to caspofungin, or a polymorph, pharmaceutically acceptable salt, hydrate, or solvate thereof, is from about 20:1 to about 1:20. In some embodiments, the weight ratio of polyvinylpyrrolidone (PVP) to caspofungin, or a polymorph, pharmaceutically acceptable salt, hydrate, or solvate thereof, is from about 10:1 to about 1:10. In some embodiments, the weight ratio of polyvinylpyrrolidone (PVP) to caspofungin, or a polymorph, pharmaceutically acceptable salt, hydrate, or solvate thereof, is from about 10:1 to about 1:1. In some embodiments, the weight ratio of polyvinylpyrrolidone (PVP) to caspofungin, or a polymorph, pharmaceutically acceptable salt, hydrate, or solvate thereof, is about 20:1, about 19:1, about 18:1, about 17:1, about 16:1, about 15:1, about 14:1, about 13:1, about 14:1, about 13:1, about 12:1, about 11:1, about 10:1, about 9:1, about 8:1, about 7:1, about 6:1, about 5:1, about 4:1, about 3:1, about 2:1, or about 1:1. In some embodiments, the weight ratio of polyvinylpyrrolidone (PVP) to caspofungin, or a polymorph, pharmaceutically acceptable salt, hydrate, or solvate thereof, is about 10:1, about 9:1, about 8:1, about 7:1, about 6:1, about 5:1, about 4:1, about 3:1, about 2:1, or about 1:1. In some embodiments, the weight ratio of polyvinylpyrrolidone (PVP) to caspofungin, or a polymorph, pharmaceutically acceptable salt, hydrate, or solvate thereof, is about 6:1, about 4:1, about 2:1, or about 1:1. In some embodiments, the weight ratio of polyvinylpyrrolidone (PVP) to caspofungin, or a polymorph, pharmaceutically acceptable salt, hydrate, or solvate thereof, is about 4:1.

In some embodiments, the weight ratio of polyvinylpyrrolidone (PVP) to caspofungin acetate is from about 20:1 to about 1:20. In some embodiments, the weight ratio of polyvinylpyrrolidone (PVP) to caspofungin acetate is from about 10:1 to about 1:10. In some embodiments, the weight ratio of polyvinylpyrrolidone (PVP) to caspofungin acetate is from about 10:1 to about 1:1. In some embodiments, the weight ratio of polyvinylpyrrolidone (PVP) to caspofungin acetate is about 20:1, about 19:1, about 18:1, about 17:1, about 16:1, about 15:1, about 14:1, about 13:1, about 14:1, about 13:1, about 12:1, about 11:1, about 10:1, about 9:1, about 8:1, about 7:1, about 6:1, about 5:1, about 4:1, about 3:1, about 2:1, or about 1:1. In some embodiments, the weight ratio of polyvinylpyrrolidone (PVP) to caspofungin acetate is about 10:1, about 9:1, about 8:1, about 7:1, about 6:1, about 5:1, about 4:1, about 3:1, about 2:1, or about 1:1. In some embodiments, the weight ratio of polyvinylpyrrolidone (PVP) to caspofungin acetate is about 6:1, about 4:1, about 2:1, or about 1:1. In some embodiments, the weight ratio of polyvinylpyrrolidone (PVP) to caspofungin acetate is about 4:1.

In some instances, it is recognized herein the addition of salts provide an enhancement in storage stability. In some embodiments, the composition further comprises at least one stability-enhancing salt. In some embodiments, the at least one stability-enhancing salt is sodium chloride, potassium chloride, or a combination thereof. In some embodiments, the at least one stability-enhancing salt further comprises sodium phosphate, potassium phosphate, or a combination thereof. In some embodiments, the sodium phosphate is disodium hydrogen phosphate, and the potassium phosphate is potassium dihydrogen phosphate.

In some embodiments, the composition further comprises a pH modifier. In some embodiments, the pH modifier is sodium hydroxide or acetic acid. In some embodiments, the pH modifier is sodium hydroxide. In some embodiments, the pH modifier is acetic acid. In some embodiments, the pH modifier is a combination of sodium hydroxide and acetic acid. In some embodiments, the composition has a pH of from about 5 to about 7. In some embodiments, the composition has a pH of from about 6.

In some embodiments, the composition further comprises a vehicle. In some embodiments, the vehicle is buffered. Buffered as referenced herein refers to an aqueous solution that experiences small changes in pH in response to the addition of a small amount of a strong acid or base. In some embodiments, the vehicle is water, saline, or phosphate-buffered saline. In some embodiments, the vehicle is water.

In some embodiments, the buffer is saline. In some embodiments, the vehicle is phosphate-buffered saline.

In some embodiments, the vehicle has a volume of from about 0.1 mL to about 10 mL. In some embodiments, the vehicle has a volume of from about 0.1 mL to about 5 mL. In some embodiments, the vehicle has a volume of from about 0.1 mL to about 3 mL. In some embodiments, the vehicle has a volume of about 0.1 mL. In some embodiments, the vehicle has a volume of about 0.2 mL. In some embodiments, the vehicle has a volume of about 0.3 mL. In some embodiments, the vehicle has a volume of about 0.4 mL. In some embodiments, the vehicle has a volume of about 0.5 mL. In some embodiments, the vehicle has a volume of about 0.6 mL. In some embodiments, the vehicle has a volume of about 0.7 mL. In some embodiments, the vehicle has a volume of about 0.8 mL. In some embodiments, the vehicle has a volume of about 0.9 mL. In some embodiments, the vehicle has a volume of about 1 mL. In some embodiments, the vehicle has a volume of about 1.5 mL. In some embodiments, the vehicle has a volume of about 2 mL. In some embodiments, the vehicle has a volume of about 2.5 mL. In some embodiments, the vehicle has a volume of about 3 mL. In some embodiments, the vehicle has a volume of about 3.5 mL. In some embodiments, the vehicle has a volume of about 4 mL. In some embodiments, the vehicle has a volume of about 4.5 mL. In some embodiments, the vehicle has a volume of about 5 mL. In some embodiments, the vehicle has a volume of about 5.5 mL. In some embodiments, the vehicle has a volume of about 6 mL. In some embodiments, the vehicle has a volume of about 6.5 mL. In some embodiments, the vehicle has a volume of about 7 mL. In some embodiments, the vehicle has a volume of about 7.5 mL. In some embodiments, the vehicle has a volume of about 8 mL. In some embodiments, the vehicle has a volume of about 8.5 mL. In some embodiments, the vehicle has a volume of about 9 mL. In some embodiments, the vehicle has a volume of about 9.5 mL. In some embodiments, the vehicle has a volume of about 10 mL.

In some embodiments, the composition is a pre-lyophilized composition. In some embodiments, the pre-lyophilized composition is sterilized by filtration.

In some embodiments, the composition is a lyophilized composition. In some embodiments, the lyophilized composition comprises less than about 10% by weight of water. In some embodiments, the lyophilized composition comprises less than about 5% by weight of water. In some embodiments, the lyophilized composition comprises less than about 2% by weight of water.

In some embodiments, the lyophilized composition comprises from about 10% to about 0.1% by weight of water. In some embodiments, the lyophilized composition comprises from about 5% to about 0.1% by weight of water. In some embodiments, the lyophilized composition comprises from about 2% to about 0.1% by weight of water. In some embodiments, the lyophilized composition comprises about 10%, about 9%, about 8%, about 7%, about 6%, about 5%, about 4%, about 3%, about 2%, about 1%, about 0.9%, about 0.8%, about 0.7%, about 0.6%, about 0.5%, about 0.4% about 0.3%, about 0.2%, or about 0.1% by weight of water.

In some embodiments, the lyophilized composition is reconstituted with water, saline, or phosphate-buffered saline (PBS) to provide a reconstituted solution. In some embodiments, the lyophilized composition is reconstituted with water to provide a reconstituted solution. In some embodiments, the lyophilized composition is reconstituted with saline to provide a reconstituted solution. In some embodiments, the lyophilized composition is reconstituted with phosphate-buffered saline (PBS) to provide a reconstituted solution.

Inhalation Devices

An "inhalation device," as used herein, refers to any device that is capable of administering a drug formulation to the respiratory airways of a patient. Inhalation devices include, for example, jet nebulizers, ultrasonic wave nebulizers, high efficiency nebulizers, heat vaporizers, soft mist inhalers, thermal aerosol inhaler, or electrohydrodynamic-based solution misting inhaler. Nebulizers deliver pharmaceuticals by forming an aerosol which includes droplet sizes that can easily be inhaled. The aerosol can be used by a patient within the bounds of an inhalation therapy, whereby the caspofungin reaches the patient's respiratory tract upon inhalation.

Inhalation devices may be mechanical or electrical, and include, for example, jet nebulizers and ultrasonic nebulizers. Jet nebulizers generally utilize compressors to generate compressed air, which breaks the liquid medication into small breathable droplets, which form an aerosolized (atomized) mist. In some embodiments, when the patient breathes in, a valve at the top opens, which then allows air into the apparatus, thereby speeding up the mist generation; when the patient breathes out, the top valve closes, thereby slowing down the mist generation while simultaneously permitting the patient to breathe out through the opening of a mouthpiece flap. Some nebulizers may provide the aerosol in a continuous mode (e.g., the eFlow from PARI Pharma Starnberg), by a breath enhanced mode (e.g., the PARI LC Plus or Sprint from PARI Starnberg), by breath actuated mode dependent on the breathing pattern of the patient (e.g., the AeroEclipse from Trudell, Canada or the I-Neb from Philips Respironics), or according to given inhalation profile (e.g., the Akita from Activaero, Gemuenden, Germany).

Some inhalation devices are disclosed in U.S. Pat. Nos. 6,513,727, 6,513,519, 6,176,237, 6,085,741, 6,000,394, 5,957,389, 5,740,966, 5,549,102, 5,461,695, 5,458,136, 5,312,046, 5,309,900, 5,280,784, and 4,496,086, each of which is hereby incorporated by reference in its entirety. Commercial inhalation devices include but are not limited to: PARI (Germany) under the trade names PARI LC Plus®, LC Star®, and PARI-Jet®; A & H Products, Inc. (Tulsa, Okla.) under the trade name AquaTower®; Hudson RCI (Temecula, Calif.) under the trade name AVA-NEB®; Intersurgical, Inc. (Liverpool, N.Y.) under the trade name Cirrus®; Salter Labs (Arvin, Calif.) under the trade name Salter 8900®; Respironics (Murrysville, Pa.) under the trade name Sidestream®; Bunnell (Salt Lake City, Utah) under the trade name Whisper Jet®; Smiths-Medical (Hyth Kent, UK) under the trade name Downdraft®, and DeVilbiss (Somerset, Pa.) under the trade name DeVilbiss®; or Trudell, Canada under the trade name AeroEclipse®.

High efficiency nebulizers are inhalation devices that comprise a micro-perforated membrane through which a liquid solution is converted through electrical or mechanical means into aerosol droplets suitable for inhalation. High efficiency nebulizers can deliver a large fraction of a loaded dose to a patient. Commercial high efficiency nebulizers include, but are not limited to: PART (Germany) under the trade name eFlow®; Aerogen, Ltd. (Ireland) under the trade names AeroNeb® Go and AeroNeb® Pro, AeroNeb® Solo, and other nebulizers utilizing the OnQ® nebulizer technology; Respironics (Murrysville, Calif.) under the trade names I-Neb®; Omron (Bannockburn, Ill.) under the trade name MicroAir®; Activaero (Germany) under the trade name Akita®, and AerovectRx (Atlanta, Ga.) under the trade name AerovectRx®.

In some embodiments, the inhalation device is selected from a jet nebulizer, ultrasonic wave nebulizer, high efficiency nebulizer, heat vaporizer, soft mist inhaler, thermal aerosol inhaler, or electrohydrodynamic-based solution misting inhaler. In some embodiments, the inhalation device is a jet nebulizer. In some embodiments, the inhalation device is an ultrasonic wave nebulizer. In some embodiments, the inhalation device is a high efficiency nebulizer. In some embodiments, the inhalation device is a heat vaporizer. In some embodiments, the inhalation device is a soft mist inhaler. In some embodiments, the inhalation device is a thermal aerosol inhaler. In some embodiments, the inhalation device is an electrohydrodynamic-based solution misting inhaler.

In some embodiments the caspofungin, or a polymorph, pharmaceutically acceptable salt, hydrate, or solvate thereof, is administered with an inhalation device, e.g., jet nebulizers, ultrasonic wave nebulizers, high efficiency nebulizers, heat vaporizers, soft mist inhalers, thermal aerosol inhaler, or electrohydrodynamic-based solution misting inhaler. The methods disclosed herein provide improved efficacy for the treatment or prophylaxis of a fungal infection in the pulmonary system of a subject relative to administration of caspofungin, or a polymorph, pharmaceutically acceptable salt, hydrate, or solvate thereof, by a different route of administration, e.g., intravenously, because administration of the caspofungin, or a polymorph, pharmaceutically acceptable salt, hydrate, or solvate thereof, with an inhalation device, e.g., jet nebulizers, ultrasonic wave nebulizers, high efficiency nebulizers, heat vaporizers, soft mist inhalers, thermal aerosol inhaler, or electrohydrodynamic-based solution misting inhaler, allows for the attainment of high concentration of caspofungin, or a polymorph, pharmaceutically acceptable salt, hydrate, or solvate thereof in the pulmonary system. In further embodiments, administration of caspofungin, or a polymorph, pharmaceutically acceptable salt, hydrate, or solvate thereof via an inhalation device minimizes systemic toxicities.

Inhalation Therapy

In some embodiments, the administration of the composition provides a lung tissue concentration of caspofungin, or the polymorph, pharmaceutically acceptable salt, hydrate, or solvate thereof, that is from about 1-fold to about 100-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 90-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 80-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 70-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 60-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 50-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 40-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 30-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 20-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 10-fold greater than intravenous administration at the same delivery dose. In some embodiments, the administration of the composition provides a lung tissue concentration of caspofungin, or the polymorph, pharmaceutically acceptable salt, hydrate, or solvate thereof, that is from about 1-fold to about 5-fold greater than intravenous administration at the same delivery dose.

In some embodiments, the administration of the composition provides a lung tissue concentration of caspofungin, or the polymorph, pharmaceutically acceptable salt, hydrate, or solvate thereof, that is about 1-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 5-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 10-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 20-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 30-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 40-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 50-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 60-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 70-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 80-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 90-fold greater than intravenous administration at the same delivery dose. In some embodiments, the administration of the composition provides a lung tissue concentration of caspofungin, or the polymorph, pharmaceutically acceptable salt, hydrate, or solvate thereof, that is about 100-fold greater than intravenous administration at the same delivery dose.

In some embodiments, the lung tissue concentration of caspofungin, or the polymorph, pharmaceutically acceptable salt, hydrate, or solvate thereof, is greater than intravenous administration at the same delivery dose for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the lung tissue concentration of caspofungin, or the polymorph, pharmaceutically acceptable salt, hydrate, or solvate thereof, is greater than intravenous administration at the same delivery dose for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the lung tissue concentration of caspofungin, or the polymorph, pharmaceutically acceptable salt, hydrate, or solvate thereof, is greater than intravenous administration at the same delivery dose for 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the lung tissue concentration of caspofungin, or the polymorph, pharmaceutically acceptable salt, hydrate, or solvate thereof, is greater than intravenous administration at the same delivery dose for 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the lung tissue concentration of caspofungin, or the polymorph, pharmaceutically acceptable salt, hydrate, or solvate thereof, is greater than intravenous administration at the same delivery dose for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin, or the polymorph, pharmaceutically acceptable salt, hydrate, or solvate thereof, in the lung that is from about 1-fold greater to about 1000-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 500-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 350-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 300-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 250-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 200-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 150-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 120-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 110-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 100-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 90-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 80-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 70-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 60-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 50-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 40-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 30-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 20-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 10-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is from about 1-fold greater to about 5-fold greater than a concentration of caspofungin, or the polymorph, pharmaceutically acceptable salt, hydrate, or solvate thereof, in the liver, kidney, or plasma.

In some embodiments, the administration of the composition provides a concentration of caspofungin, or the polymorph, pharmaceutically acceptable salt, hydrate, or solvate thereof, in the lung that is about 1-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 2-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 3-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 4-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 5-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 10-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 15-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 20-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 30-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 40-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 50-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 60-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 70-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 80-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 90-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 100-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 110-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 120-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 130-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 140-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 150-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 200-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 250-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 300-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 350-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 400-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 500-fold greater than the concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 600-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 700-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 800-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 900-fold greater than a concentration of caspofungin, or the polymorph, pharmaceutically acceptable salt, hydrate, or solvate thereof, in the liver, kidney, or plasma. In some embodiments, the administration of the composition provides a concentration of caspofungin, or the polymorph, pharmaceutically acceptable salt, hydrate, or solvate thereof, in the lung that is about 1000-fold greater than a concentration of caspofungin, or the polymorph, pharmaceutically acceptable salt, hydrate, or solvate thereof, in the liver, kidney, or plasma.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin, or the polymorph, pharmaceutically acceptable salt, hydrate, or solvate thereof, in the lung that is from about 1-fold greater to about 1000-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 500-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 350-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 300-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 250-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 200-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 150-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 120-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 110-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 100-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 90-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 80-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 70-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 60-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 50-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 40-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 30-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 20-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 10-fold greater than a concentration of caspofungin, or the polymorph, pharmaceutically acceptable salt, hydrate, or solvate thereof, in the liver. In some embodiments, the administration of the composition provides a concentration of caspofungin, or the polymorph, pharmaceutically acceptable salt, hydrate, or solvate thereof, in the lung that is from about 1-fold greater to about 5-fold greater than a concentration of caspofungin, or the polymorph, pharmaceutically acceptable salt, hydrate, or solvate thereof, in the liver.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin, or the polymorph, pharmaceutically acceptable salt, hydrate, or solvate thereof, in the lung that is from about 1-fold greater to about 1000-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 500-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 350-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 300-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 250-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 200-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 150-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 120-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 110-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 100-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 90-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 80-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 70-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 60-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 50-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 40-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 30-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 20-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 10-fold greater than a concentration of caspofungin, or the polymorph, pharmaceutically acceptable salt, hydrate, or solvate thereof, in the kidney. In some embodiments, the administration of the composition provides a concentration of caspofungin, or the polymorph, pharmaceutically acceptable salt, hydrate, or solvate thereof, in the lung that is from about 1-fold greater to about 5-fold greater than a concentration of caspofungin, or the polymorph, pharmaceutically acceptable salt, hydrate, or solvate thereof, in the kidney.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the kidney for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the kidney for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the kidney for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the kidney for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the kidney for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin, or the polymorph, pharmaceutically acceptable salt, hydrate, or solvate thereof, in the lung that is from about 1-fold greater to about 1000-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 500-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 350-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 300-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 250-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 200-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 150-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 120-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 110-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 100-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 90-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 80-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 70-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 60-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 50-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 40-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 30-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 20-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 10-fold greater than a concentration of caspofungin, or the polymorph, pharmaceutically acceptable salt, hydrate, or solvate thereof, in the spleen. In some embodiments, the administration of the composition provides a concentration of caspofungin, or the polymorph, pharmaceutically acceptable salt, hydrate, or solvate thereof, in the lung that is from about 1-fold greater to about 5-fold greater than a concentration of caspofungin, or the polymorph, pharmaceutically acceptable salt, hydrate, or solvate thereof, in the spleen.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the spleen for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the spleen for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the spleen for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the spleen for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the spleen for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin, or the polymorph, pharmaceutically acceptable salt, hydrate, or solvate thereof, in the lung that is from about 1-fold greater to about 1000-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 500-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 350-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 300-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 250-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 200-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 150-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 120-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 110-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 100-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 90-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 80-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 70-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 60-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 50-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 40-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 30-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 20-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 10-fold greater than a concentration of caspofungin, or the polymorph, pharmaceutically acceptable salt, hydrate, or solvate thereof, in the pancreas. In some embodiments, the administration of the composition provides a concentration of caspofungin, or the polymorph, pharmaceutically acceptable salt, hydrate, or solvate thereof, in the lung that is from about 1-fold greater to about 5-fold greater than a concentration of caspofungin, or the polymorph, pharmaceutically acceptable salt, hydrate, or solvate thereof, in the pancreas.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the pancreas for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the pancreas for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the pancreas for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the pancreas for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the pancreas for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the administration of the composition provides a concentration of caspofungin, or the polymorph, pharmaceutically acceptable salt, hydrate, or solvate thereof, in the lung that is from about 1-fold greater to about 1000-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 500-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 350-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 300-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 250-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 200-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 150-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 120-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 110-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 100-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 90-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 80-fold greater than the concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 70-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 60-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 50-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 40-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 30-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 20-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 10-fold greater than a concentration of caspofungin, or the polymorph, pharmaceutically acceptable salt, hydrate, or solvate thereof, in plasma. In some embodiments, the administration of the composition provides a concentration of caspofungin, or the polymorph, pharmaceutically acceptable salt, hydrate, or solvate thereof, in the lung that is from about 1-fold greater to about 5-fold greater than a concentration of caspofungin, or the polymorph, pharmaceutically acceptable salt, hydrate, or solvate thereof, in plasma.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the plasma for about 0.5 hour to about 336 hours, about 0.5 hour to about 168 hours, about 0.5 hour to about 144 hours, about 0.5 hour to about 120 hours, about 0.5 hour to about 96 hours, about 0.5 hour to about 72 hours, about 0.5 hour to about 60 hours, about 0.5 hour to about 48 hours, about 0.5 to about 36 hours, about 0.5 to about 24 hours, about 0.5 hour to about 12 hours, about 0.5 hour to about 6 hours, about 0.5 hour to about 3 hours, or about 0.5 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in plasma for about 1 hour to about 336 hours, about 1 hour to about 168 hours, about 1 hour to about 144 hours, about 1 hour to about 120 hours, about 1 hour to about 96 hours, about 1 hour to about 72 hours, about 1 hour to about 60 hours, about 1 hour to about 48 hours, about 1 hour to about 36 hours, about 1 hour to about 24 hours, about 1 hour to about 12 hours, about 1 hour to about 6 hours, for about 1 hour to about 3 hours, or about 1 hour to about 2 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the plasma for about 3 hours to about 336 hours, about 3 hours to about 168 hours, about 3 hours to about 144 hours, about 3 hours to about 120 hours, about 3 hours to about 96 hours, about 3 hours to about 72 hours, about 3 hours to about 60 hours, about 3 hours to about 48 hours, about 3 hours to about 36 hours, about 3 hours to about 24 hours, about 3 hours to about 12 hours, or about 3 hours to about 6 hours. In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the plasma for about 6 hours to about 336 hours, about 6 hours to about 168 hours, about 6 hours to about 144 hours, about 6 hours to about 120 hours, about 6 hours to about 96 hours, about 6 hours to about 72 hours, about 6 hours to about 60 hours, about 6 hours to about 48 hours, about 6 hours to about 36 hours, about 6 hours to about 24 hours, or about 6 hours to about 12 hours.

In some embodiments, the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the plasma for about 0.5 hour, 1 hour, 2 hours, 3 hours, 4 hours, 5 hours, 6 hours, 7 hours, 8 hours, 9 hours, 10 hours, 11 hours, 12 hours, 18 hours, 24 hours, 32 hours, 48 hours, 72 hours, 96 hours, 120 hours, 144 hours, 168 hours, 240 hours, or 336 hours.

In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 1 hour to about 336 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for at least about 168 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 3 hours to about 336 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 1 hour after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 2 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 3 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 6 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 12 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 24 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 48 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 72 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 96 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 120 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 144 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 168 hours after administration. In some embodiments, the concentration of caspofungin, or the polymorph, pharmaceutically acceptable salt, hydrate, or solvate thereof, in the lung is above the minimum inhibitory concentration (MIC) or the minimum effective concentration (MEC) for about 336 hours after administration.

In some embodiments, the minimum inhibitory concentration (MIC) is from about 0.001 μg/mL to about 500 μg/mL. In some embodiments, the minimum inhibitory concentration (MIC) is from about 0.001 μg/mL to about 300 μg/mL. In some embodiments, the minimum inhibitory concentration (MIC) is from about 0.001 μg/mL to about 128 μg/mL. In some embodiments, the minimum inhibitory concentration (MIC) is from about 0.001 μg/mL to about 32 μg/mL. In some embodiments, the minimum inhibitory concentration (MIC) is from about 0.001 μg/mL to about 16 μg/mL. Generally, if the MIC is above 16 μg/ml, the microorganism is considered resistant to the drug.

In some embodiments, the minimum inhibitory concentration (MIC) is from about 0.125 μg/mL to about 500 μg/mL. In some embodiments, the minimum inhibitory concentration (MIC) is from about 0.125 μg/mL to about 300 μg/mL. In some embodiments, the minimum inhibitory concentration (MIC) is from about 0.125 μg/mL to about 128 μg/mL. In some embodiments, the minimum inhibitory concentration (MIC) is from about 0.125 μg/mL to about 32 μg/mL. In some embodiments, the minimum inhibitory concentration (MIC) is from about 0.125 μg/mL to about 16 μg/mL. In some embodiments, the minimum inhibitory concentration (MIC) is from about 0.25 μg/mL to about 16 μg/mL. In some embodiments, the minimum inhibitory concentration (MIC) is from about 0.25 μg/mL to about 32 μg/mL. In some embodiments, the minimum inhibitory concentration (MIC) is from about 0.25 μg/mL to about 128 μg/mL. In some embodiments, the minimum inhibitory concentration (MIC) is from about 16 μg/mL to about 128 μg/mL.

In some embodiments, the minimum inhibitory concentration (MIC) is about 0.001 μg/mL. In some embodiments, the minimum inhibitory concentration (MIC) is about 0.005 μg/mL. In some embodiments, the minimum inhibitory concentration (MIC) is about 0.010 μg/mL. In some embodiments, the minimum inhibitory concentration (MIC) is about 0.015 μg/mL. In some embodiments, the minimum inhibitory concentration (MIC) is about 0.020 μg/mL. In some embodiments, the minimum inhibitory concentration (MIC) is about 0.030 μg/mL. In some embodiments, the minimum inhibitory concentration (MIC) is about 0.040 μg/mL. In some embodiments, the minimum inhibitory concentration (MIC) is about 0.050 μg/mL. In some embodiments, the minimum inhibitory concentration (MIC) is about 0.060 μg/mL. In some embodiments, the minimum inhibitory concentration (MIC) is about 0.070 μg/mL. In some embodiments, the minimum inhibitory concentration (MIC) is about 0.080 μg/mL. In some embodiments, the minimum inhibitory concentration (MIC) is about 0.090 μg/mL. In some embodiments, the minimum inhibitory concentration (MIC) is about 0.100 μg/mL. In some embodiments, the minimum inhibitory concentration (MIC) is about 0.125 μg/mL. In some embodiments, the minimum inhibitory concentration (MIC) is about 0.20 μg/mL. In some embodiments, the minimum inhibitory concentration (MIC) is about 0.25 μg/mL. In some embodiments, the minimum inhibitory concentration (MIC) is about 0.30 μg/mL. In some embodiments, the minimum inhibitory concentration (MIC) is about 0.50 μg/mL. In some embodiments, the minimum inhibitory concentration (MIC) is about 0.75 μg/mL. In some embodiments, the minimum inhibitory concentration (MIC) is about 1.00 μg/mL. In some embodiments, the minimum inhibitory concentration (MIC) is about 1.50 μg/mL. In some embodiments, wherein the minimum inhibitory concentration (MIC) is about 2.00 μg/mL. In some embodiments, wherein the minimum inhibitory concentration (MIC) is about 2.50 μg/mL. In some embodiments, wherein the minimum inhibitory concentration (MIC) is about 3.00 μg/mL. In some embodiments, the minimum inhibitory concentration (MIC) is about 4.00 μg/mL. In some embodiments, the minimum inhibitory concentration (MIC) is about 8.00 μg/mL. In some embodiments, the minimum inhibitory concentration (MIC) is about 10.00 μg/mL. In some embodiments, the minimum inhibitory concentration (MIC) is about 16.00 μg/mL. In some embodiments, the minimum inhibitory concentration (MIC) is about 20.00 μg/mL. In some embodiments, the minimum inhibitory concentration (MIC) is about 30.00 μg/mL. In some embodiments, the minimum inhibitory concentration (MIC) is about 32.00 μg/mL. In some embodiments, the minimum inhibitory concentration (MIC) is about 40.00 μg/mL. In some embodiments, the minimum inhibitory concentration (MIC) is about 60.00 μg/mL. In some embodiments, the minimum inhibitory concentration (MIC) is about 80.00 μg/mL. In some embodiments, the minimum inhibitory concentration (MIC) is about 100.00 μg/mL. In some embodiments, the minimum inhibitory concentration (MIC) is about 120.00 μg/mL. In some embodiments, the minimum inhibitory concentration (MIC) is about 128.00 μg/mL. In some embodiments, the minimum inhibitory concentration (MIC) is about 150.00 μg/mL. In some embodiments, the minimum inhibitory concentration (MIC) is about 200.00 μg/mL. In some embodiments, the minimum inhibitory concentration (MIC) is about 300.00 μg/mL. In some embodiments, the minimum inhibitory concentration (MIC) is about 400.00 μg/mL. In some embodiments, the minimum inhibitory concentration (MIC) is about 500.00 μg/mL.

In some embodiments, the minimum effective concentration (MEC) is from about 0.001 μg/mL to about 500 μg/mL. In some embodiments, the minimum effective concentration (MEC) is from about 0.001 μg/mL to about 300 μg/mL. In some embodiments, the minimum effective concentration (MEC) is from about 0.001 μg/mL to about 128 μg/mL. In some embodiments, the minimum effective concentration (MEC) is from about 0.001 µg/mL to about 32 µg/mL. In some embodiments, the minimum effective concentration (MEC) is from about 0.001 µg/mL to about 16 µg/mL. In some embodiments, the minimum effective concentration (MEC) is from about 0.001 µg/mL to about 1.0 µg/mL. In some embodiments, the minimum effective concentration (MEC) is from about 0.001 µg/mL to about 0.6 µg/mL. In some embodiments, the minimum effective concentration (MEC) is from about 0.001 µg/mL to about 0.3 µg/mL. In some embodiments, the minimum effective concentration (MEC) is from about 0.001 µg/mL to about 0.1 µg/mL. In some embodiments, the minimum effective concentration (MEC) is from about 0.008 µg/mL to about 0.6 µg/mL. In some embodiments, the minimum effective concentration (MEC) is from about 0.008 µg/mL to about 0.3 µg/mL. In some embodiments, the minimum effective concentration (MEC) is from about 0.008 µg/mL to about 0.06 µg/mL.

In some embodiments, minimum effective concentration (MEC) is about 0.001 µg/mL. In some embodiments, the minimum effective concentration (MEC) is about 0.005 µg/mL. In some embodiments, the minimum effective concentration (MEC) is about 0.010 µg/mL. In some embodiments, the minimum effective concentration (MEC) is about 0.015 µg/mL. In some embodiments, the minimum effective concentration (MEC) is about 0.020 µg/mL. In some embodiments, the minimum effective concentration (MEC) is about 0.030 µg/mL. In some embodiments, the minimum effective concentration (MEC) is about 0.040 µg/mL. In some embodiments, the minimum effective concentration (MEC) is about 0.050 µg/mL. In some embodiments, the minimum effective concentration (MEC) is about 0.060 µg/mL. In some embodiments, the minimum effective concentration (MEC) is about 0.070 µg/mL. In some embodiments, the minimum effective concentration (MEC) is about 0.080 µg/mL. In some embodiments, the minimum effective concentration (MEC) is about 0.090 µg/mL. In some embodiments, the minimum effective concentration (MEC) is about 0.100 µg/mL. In some embodiments, the minimum effective concentration (MEC) is about 0.125 µg/mL. In some embodiments, the minimum effective concentration (MEC) is about 0.200 µg/mL. In some embodiments, the minimum effective concentration (MEC) is about 0.250 µg/mL. In some embodiments, the minimum effective concentration (MEC) is about 0.300 µg/mL. In some embodiments, the minimum effective concentration (MEC) is about 0.400 µg/mL. In some embodiments, the minimum effective concentration (MEC) is about 0.500 µg/mL. In some embodiments, the minimum effective concentration (MEC) is about 0.600 µg/mL. In some embodiments, the minimum effective concentration (MEC) is about 0.700 µg/mL. In some embodiments, the minimum effective concentration (MEC) is about 0.75 µg/mL. In some embodiments, the minimum effective concentration (MEC) is about 0.800 µg/mL. In some embodiments, the minimum effective concentration (MEC) is about 0.900 µg/mL. In some embodiments, the minimum effective concentration (MEC) is about 1.000 µg/mL. In some embodiments, the minimum effective concentration (MEC) is about 1.500 µg/mL. In some embodiments, the minimum effective concentration (MEC) is about 2.000 µg/mL. In some embodiments, the minimum effective concentration (MEC) is about 2.500 µg/mL. In some embodiments, the minimum effective concentration (MEC) is about 3.000 µg/mL. In some embodiments, the minimum effective concentration (MEC) is about 4.000 µg/mL. In some embodiments, the minimum effective concentration (MEC) is about 8.000 µg/mL. In some embodiments, the minimum effective concentration (MEC) is about 10.000 µg/mL. In some embodiments, the minimum effective concentration (MEC) is about 16.00 µg/mL. In some embodiments, the minimum effective concentration (MEC) is about 20.00 µg/mL. In some embodiments, the minimum effective concentration (MEC) is about 30.00 µg/mL. In some embodiments, the minimum effective concentration (MEC) is about 32.00 µg/mL. In some embodiments, the minimum effective concentration (MEC) is about 40.00 µg/mL. In some embodiments, the minimum effective concentration (MEC) is about 60.00 µg/mL. In some embodiments, the minimum effective concentration (MEC) is about 80.00 µg/mL. In some embodiments, the minimum effective concentration (MEC) is about 100.00 µg/mL. In some embodiments, the minimum effective concentration (MEC) is about 120.00 µg/mL. In some embodiments, the minimum effective concentration (MEC) is about 128.00 µg/mL. In some embodiments, the minimum effective concentration (MEC) is about 150.00 µg/mL. In some embodiments, the minimum effective concentration (MEC) is about 200.00 µg/mL. In some embodiments, the minimum effective concentration (MEC) is about 300.00 µg/mL. In some embodiments, the minimum effective concentration (MEC) is about 400.00 µg/mL. In some embodiments, the minimum effective concentration (MEC) is about 500.00 µg/mL.

It is recognized herein that in some embodiments, the compositions containing polyvinylpyrrolidone allow for delivery of the caspofungin, or the polymorph, pharmaceutically acceptable salt, hydrate, or solvate thereof, at a greater concentration to the lung when compared to compositions that do not have polyvinylpyrrolidone.

In some embodiments, the administration of the composition with polyvinylpyrrolidone provides a lung tissue concentration of caspofungin, or the polymorph, pharmaceutically acceptable salt, hydrate, or solvate thereof, that is about 1-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 1.1-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 1.2-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 1.3-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 1.4-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 1.5-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 1.6-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 1.7-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 1.8-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 1.9-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 2-fold greater than a similar composition that does not contain polyvinylpyrrolidone at the same delivery dose. In some embodiments, the administration of the composition with polyvinylpyrrolidone provides a lung tissue concentration of caspofungin, or the polymorph, pharmaceutically acceptable salt, hydrate, or solvate thereof, that is about 3-fold greater than a similar composition that does not contain polyvinylpyrrolidone at the same delivery dose.

In some embodiments, the concentration of caspofungin, or the polymorph, pharmaceutically acceptable salt, hydrate, or solvate thereof, in the lung is greater than about 5 µg/g for about 0.5 hour to about 24 hours. In some embodiments, the concentration of caspofungin, or the polymorph, pharmaceutically acceptable salt, hydrate, or solvate thereof, in the lung is greater than about 5 µg/g for about 0.5 hour. In some embodiments, the concentration of caspofungin, or the polymorph, pharmaceutically acceptable salt, hydrate, or solvate thereof, in the lung is greater than about 5 µg/g for about 1 hour. In some embodiments, the concentration of caspofungin, or the polymorph, pharmaceutically acceptable salt, hydrate, or solvate thereof, in the lung is greater than about 5 µg/g for about 2 hours. In some embodiments, the concentration of caspofungin, or the polymorph, pharmaceutically acceptable salt, hydrate, or solvate thereof, in the lung is greater than about 5 µg/g for about 4 hours. In some embodiments, the concentration of caspofungin, or the polymorph, pharmaceutically acceptable salt, hydrate, or solvate thereof, in the lung is greater than about 5 µg/g for about 8 hours. In some embodiments, the concentration of caspofungin, or the polymorph, pharmaceutically acceptable salt, hydrate, or solvate thereof, in the lung is greater than about 5 µg/g for about 12 hours. In some embodiments, the concentration of caspofungin, or the polymorph, pharmaceutically acceptable salt, hydrate, or solvate thereof, in the lung is greater than about 5 µg/g for about 16 hours. In some embodiments, the concentration of caspofungin, or the polymorph, pharmaceutically acceptable salt, hydrate, or solvate thereof, in the lung is greater than about 5 µg/g for about 20 hours. In some embodiments, the concentration of caspofungin, or the polymorph, pharmaceutically acceptable salt, hydrate, or solvate thereof, in the lung is greater than about 5 µg/g for about 24 hours.

In some embodiments, the concentration of caspofungin, or the polymorph, pharmaceutically acceptable salt, hydrate, or solvate thereof, in the lung is greater than about 8 µg/g for about 0.5 hour to about 24 hours. In some embodiments, the concentration of caspofungin, or the polymorph, pharmaceutically acceptable salt, hydrate, or solvate thereof, in the lung is greater than about 8 µg/g for about 0.5 hour. In some embodiments, the concentration of caspofungin, or the polymorph, pharmaceutically acceptable salt, hydrate, or solvate thereof, in the lung is greater than about 8 µg/g for about 1 hour. In some embodiments, the concentration of caspofungin, or the polymorph, pharmaceutically acceptable salt, hydrate, or solvate thereof, in the lung is greater than about 8 µg/g for about 2 hours. In some embodiments, the concentration of caspofungin, or the polymorph, pharmaceutically acceptable salt, hydrate, or solvate thereof, in the lung is greater than about 8 µg/g for about 4 hours. In some embodiments, the concentration of caspofungin, or the polymorph, pharmaceutically acceptable salt, hydrate, or solvate thereof, in the lung is greater than about 8 µg/g for about 8 hours. In some embodiments, the concentration of caspofungin, or the polymorph, pharmaceutically acceptable salt, hydrate, or solvate thereof, in the lung is greater than about 8 µg/g for about 12 hours. In some embodiments, the concentration of caspofungin, or the polymorph, pharmaceutically acceptable salt, hydrate, or solvate thereof, in the lung is greater than about 8 µg/g for about 16 hours. In some embodiments, the concentration of caspofungin, or the polymorph, pharmaceutically acceptable salt, hydrate, or solvate thereof, in the lung is greater than about 8 µg/g for about 20 hours. In some embodiments, the concentration of caspofungin, or the polymorph, pharmaceutically acceptable salt, hydrate, or solvate thereof, in the lung is greater than about 8 µg/g for about 24 hours.

In some embodiments, concentration of caspofungin, or the polymorph, pharmaceutically acceptable salt, hydrate, or solvate thereof, in the lung is greater than about 10 µg/g for about 0.5 hour to about 2 hours. In some embodiments, concentration of caspofungin, or the polymorph, pharmaceutically acceptable salt, hydrate, or solvate thereof, in the lung is greater than about 10 µg/g for about 0.5 hour. In some embodiments, concentration of caspofungin, or the polymorph, pharmaceutically acceptable salt, hydrate, or solvate thereof, in the lung is greater than about 10 µg/g for about 1 hour. In some embodiments, concentration of caspofungin, or the polymorph, pharmaceutically acceptable salt, hydrate, or solvate thereof, in the lung is greater than about 10 µg/g for about 2 hours. In some embodiments, concentration of caspofungin, or the polymorph, pharmaceutically acceptable salt, hydrate, or solvate thereof, in the lung is greater than about 10 µg/g for about 4 hours. In some embodiments, concentration of caspofungin, or the polymorph, pharmaceutically acceptable salt, hydrate, or solvate thereof, in the lung is greater than about 10 µg/g for about 8 hours. In some embodiments, concentration of caspofungin, or the polymorph, pharmaceutically acceptable salt, hydrate, or solvate thereof, in the lung is greater than about 10 µg/g for about 12 hours. In some embodiments, concentration of caspofungin, or the polymorph, pharmaceutically acceptable salt, hydrate, or solvate thereof, in the lung is greater than about 10 µg/g for about 16 hours. In some embodiments, concentration of caspofungin, or the polymorph, pharmaceutically acceptable salt, hydrate, or solvate thereof, in the lung is greater than about 10 µg/g for about 20 hours. In some embodiments, concentration of caspofungin, or the polymorph, pharmaceutically acceptable salt, hydrate, or solvate thereof, in the lung is greater than about 10 μg/g for about 24 hours.

In some embodiments, concentration of caspofungin, or the polymorph, pharmaceutically acceptable salt, hydrate, or solvate thereof, in the lung is greater than about 12 μg/g for about 0.5 hour to about 2 hours. In some embodiments, concentration of caspofungin, or the polymorph, pharmaceutically acceptable salt, hydrate, or solvate thereof, in the lung is greater than about 12 μg/g for about 0.5 hour. In some embodiments, concentration of caspofungin, or the polymorph, pharmaceutically acceptable salt, hydrate, or solvate thereof, in the lung is greater than about 12 μg/g for about 1 hour. In some embodiments, concentration of caspofungin, or the polymorph, pharmaceutically acceptable salt, hydrate, or solvate thereof, in the lung is greater than about 12 μg/g for about 2 hours. In some embodiments, concentration of caspofungin, or the polymorph, pharmaceutically acceptable salt, hydrate, or solvate thereof, in the lung is greater than about 12 μg/g for about 4 hours. In some embodiments, concentration of caspofungin, or the polymorph, pharmaceutically acceptable salt, hydrate, or solvate thereof, in the lung is greater than about 12 μg/g for about 8 hours. In some embodiments, concentration of caspofungin, or the polymorph, pharmaceutically acceptable salt, hydrate, or solvate thereof, in the lung is greater than about 12 μg/g for about 12 hours. In some embodiments, concentration of caspofungin, or the polymorph, pharmaceutically acceptable salt, hydrate, or solvate thereof, in the lung is greater than about 12 μg/g for about 16 hours. In some embodiments, concentration of caspofungin, or the polymorph, pharmaceutically acceptable salt, hydrate, or solvate thereof, in the lung is greater than about 12 μg/g for about 20 hours. In some embodiments, concentration of caspofungin, or the polymorph, pharmaceutically acceptable salt, hydrate, or solvate thereof, in the lung is greater than about 12 μg/g for about 24 hours.

In some embodiments, concentration of caspofungin, or the polymorph, pharmaceutically acceptable salt, hydrate, or solvate thereof, in the lung is greater than about 14 μg/g for about 0.5 hour to about 2 hours. In some embodiments, concentration of caspofungin, or the polymorph, pharmaceutically acceptable salt, hydrate, or solvate thereof, in the lung is greater than about 14 μg/g for about 0.5 hour. In some embodiments, concentration of caspofungin, or the polymorph, pharmaceutically acceptable salt, hydrate, or solvate thereof, in the lung is greater than about 14 μg/g for about 1 hour. In some embodiments, concentration of caspofungin, or the polymorph, pharmaceutically acceptable salt, hydrate, or solvate thereof, in the lung is greater than about 14 μg/g for about 2 hours. In some embodiments, concentration of caspofungin, or the polymorph, pharmaceutically acceptable salt, hydrate, or solvate thereof, in the lung is greater than about 14 μg/g for about 4 hours. In some embodiments, concentration of caspofungin, or the polymorph, pharmaceutically acceptable salt, hydrate, or solvate thereof, in the lung is greater than about 14 μg/g for about 8 hours. In some embodiments, concentration of caspofungin, or the polymorph, pharmaceutically acceptable salt, hydrate, or solvate thereof, in the lung is greater than about 14 μg/g for about 12 hours. In some embodiments, concentration of caspofungin, or the polymorph, pharmaceutically acceptable salt, hydrate, or solvate thereof, in the lung is greater than about 14 μg/g for about 16 hours. In some embodiments, concentration of caspofungin, or the polymorph, pharmaceutically acceptable salt, hydrate, or solvate thereof, in the lung is greater than about 14 μg/g for about 20 hours. In some embodiments, concentration of caspofungin, or the polymorph, pharmaceutically acceptable salt, hydrate, or solvate thereof, in the lung is greater than about 14 μg/g for about 24 hours.

In some embodiments, the composition provides an increase of greater than about 20% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of greater than about 30% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of greater than about 40% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of greater than about 50% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of greater than about 60% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of greater than about 70% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of greater than about 80% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of greater than about 90% of caspofungin, or a polymorph, pharmaceutically acceptable salt, hydrate, or solvate thereof, deposit in the lung without increasing systemic exposure when compared to a composition that does not comprise polyvinylpyrrolidone (PVP).

In some embodiments, the composition provides an increase of about 20% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of about 30% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of about 40% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of about 50% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of about 60% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of about 70% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of about 80% of caspofungin, or a polymorph, pharmaceutically acceptable salt, hydrate, or solvate thereof, deposit in the lung without increasing systemic exposure when compared to a composition that does not comprise polyvinylpyrrolidone (PVP). In some embodiments, the composition provides an increase of about 90% of caspofungin, or a polymorph, pharmaceutically acceptable salt, hydrate, or solvate thereof, deposit in the lung without increasing systemic exposure when compared to a composition that does not comprise polyvinylpyrrolidone (PVP).

Particle Size

In some embodiments, the composition is administered by the inhalation device as droplets or particles having a mass median aerodynamic diameter (MMAD) from about 0.1 µm to about 15 µm. In some embodiments, the composition is administered by the inhalation device as droplets or particles having a mass median aerodynamic diameter (MMAD) from about 0.1 µm to about 10 µm. In some embodiments, the composition is administered by the inhalation device as droplets or particles having a mass median aerodynamic diameter (MMAD) from about 0.1 µm to about 5 µm. In some embodiments, the composition is administered by the inhalation device as droplets or particles having a mass median aerodynamic diameter (MMAD) from about 0.1 µm to about 4 µm. In some embodiments, the composition is administered by the inhalation device as droplets or particles having a mass median aerodynamic diameter (MMAD) from about 0.1 µm to about 3 µm. In some embodiments, the composition is administered by the inhalation device as droplets or particles having a mass median aerodynamic diameter (MMAD) from about 0.1 µm to about 2 µm. In some embodiments, the composition is administered by the inhalation device as droplets or particles having a mass median aerodynamic diameter (MMAD) from about 0.1 µm to about 1 µm.

In some embodiments, the composition is administered by the inhalation device as droplets or particles having a mass median aerodynamic diameter (MMAD) of about 0.1 µm. In some embodiments, the composition is administered by the inhalation device as droplets or particles having a mass median aerodynamic diameter (MMAD) of about 0.2 µm. In some embodiments, the composition is administered by the inhalation device as droplets or particles having a mass median aerodynamic diameter (MMAD) of about 0.3 µm. In some embodiments, the composition is administered by the inhalation device as droplets or particles having a mass median aerodynamic diameter (MMAD) of about 0.4 µm. In some embodiments, the composition is administered by the inhalation device as droplets or particles having a mass median aerodynamic diameter (MMAD) of about 0.5 µm. In some embodiments, the composition is administered by the inhalation device as droplets or particles having a mass median aerodynamic diameter (MMAD) of about 1 µm. In some embodiments, the composition is administered by the inhalation device as droplets or particles having a mass median aerodynamic diameter (MMAD) of about 2 µm. In some embodiments, the composition is administered by the device as droplets or particles having a mass median aerodynamic diameter (MMAD) of about 3 µm. In some embodiments, the composition is administered by the inhalation device as droplets or particles having a mass median aerodynamic diameter (MMAD) of about 4 µm. In some embodiments, the composition is administered by the inhalation device as droplets or particles having a mass median aerodynamic diameter (MMAD) of about 5 µm. In some embodiments, the composition is administered by the inhalation device as droplets or particles having a mass median aerodynamic diameter (MMAD) of about 6 µm. In some embodiments, the composition is administered by the inhalation device as droplets or particles having a mass median aerodynamic diameter (MMAD) of about 7 µm. In some embodiments, the composition is administered by the inhalation device as droplets or particles having a mass median aerodynamic diameter (MMAD) of about 8 µm. In some embodiments, the composition is administered by the inhalation device as droplets or particles having a mass median aerodynamic diameter (MMAD) of about 9 µm. In some embodiments, the composition is administered by the inhalation device as droplets or particles having a mass median aerodynamic diameter (MMAD) of about 10 µm. In some embodiments, the composition is administered by the inhalation device as droplets or particles having a mass median aerodynamic diameter (MMAD) of about 15 µm.

In some embodiments, the composition is administered by the inhalation device as droplets or particles having a GSD (geometric standard deviation) of about 1.0 to about 6.0. In some embodiments, the composition is administered by the inhalation device as droplets or particles having a GSD (geometric standard deviation) of about 1.0 to about 3.0. In some embodiments, the composition is administered by the inhalation device as droplets or particles having a GSD (geometric standard deviation) of about 2.0 to about 6.0. In some embodiments, the composition is administered by the inhalation device as droplets or particles having a GSD (geometric standard deviation) of about 2.0 to about 3.0.

In some embodiments, the composition is administered by the inhalation device as droplets or particles having a GSD (geometric standard deviation) is about 1.0. In some embodiments, the composition is administered by the inhalation device as droplets or particles having a GSD (geometric standard deviation) is about 2.0. In some embodiments, the composition is administered by the inhalation device as droplets or particles having a GSD (geometric standard deviation) is about 3.0. In some embodiments, the composition is administered by the inhalation device as droplets or particles having a GSD (geometric standard deviation) is about 4.0. In some embodiments, the composition is administered by the inhalation device as droplets or particles having a GSD (geometric standard deviation) is about 5.0. In some embodiments, the composition is administered by the inhalation device as droplets or particles having a GSD (geometric standard deviation) is about 6.0.

Half-Life

In some embodiments, the half-life of the caspofungin, or a polymorph, pharmaceutically acceptable salt, hydrate, or solvate thereof in the lung is about 1 hour to about 100 hours. In some embodiments, the half-life of the caspofungin, or a polymorph, pharmaceutically acceptable salt, hydrate, or solvate thereof in the lung is about 1 hour to about 75 hours. In some embodiments, the half-life of the caspofungin, or a polymorph, pharmaceutically acceptable salt, hydrate, or solvate thereof in the lung is about 1 hour to about 50 hours. In some embodiments, the half-life of the caspofungin, or a polymorph, pharmaceutically acceptable salt, hydrate, or solvate thereof in the lung is about 1 hour to about 20 hours. In some embodiments, the half-life of the caspofungin, or a polymorph, pharmaceutically acceptable salt, hydrate, or solvate thereof in the lung is about 20 hours to about 50 hours. In some embodiments, the half-life of the caspofungin, or a polymorph, pharmaceutically acceptable salt, hydrate, or solvate thereof in the lung is about 30 hours to about 50 hours. In some embodiments, the half-life of the caspofungin, or a polymorph, pharmaceutically acceptable salt, hydrate, or solvate thereof in the lung is about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 50 hours, about 55 hours, about 60 hours, about 65 hours, about 70 hours, about 75 hours, about 80 hours, about 85 hours, about 90 hours, about 95 hours, or about 100 hours.

In some embodiments, the half-life of the caspofungin, or a polymorph, pharmaceutically acceptable salt, hydrate, or solvate thereof in the lung is greater than about 1 hour, greater than about 2 hours, greater than about 3 hours, greater than about 4 hours, greater than about 5 hours, greater than about 6 hours, greater than about 7 hours, greater than about 8 hours, greater than about 9 hours, greater than about 10 hours, greater than about 11 hours, greater than about 12 hours, greater than about 13 hours, greater than about 14 hours, greater than about 15 hours, greater than about 16 hours, greater than about 17 hours, greater than about 18 hours, greater than about 19 hours, greater than about 20 hours, greater than about 21 hours, greater than about 22 hours, greater than about 23 hours, greater than about 24 hours, greater than about 25 hours, greater than about 26 hours, greater than about 27 hours, greater than about 28 hours, greater than about 29 hours, greater than about 30 hours, greater than about 31 hours, greater than about 32 hours, greater than about 33 hours, greater than about 34 hours, greater than about 35 hours, greater than about 36 hours, greater than about 37 hours, greater than about 38 hours, greater than about 39 hours, greater than about 40 hours, greater than about 41 hours, greater than about 42 hours, greater than about 43 hours, greater than about 44 hours, greater than about 45 hours, greater than about 50 hours, greater than about 55 hours, greater than about 60 hours, greater than about 65 hours, greater than about 70 hours, greater than about 75 hours, greater than about 80 hours, greater than about 85 hours, greater than about 90 hours, greater than about 95 hours, or greater than about 100 hours.

In some embodiments, the half-life of the caspofungin, or a polymorph, pharmaceutically acceptable salt, hydrate, or solvate thereof in the lung is less than about 1 hour, less than about 2 hours, less than about 3 hours, less than about 4 hours, less than about 5 hours, less than about 6 hours, less than about 7 hours, less than about 8 hours, less than about 9 hours, less than about 10 hours, less than about 11 hours, less than about 12 hours, less than about 13 hours, less than about 14 hours, less than about 15 hours, less than about 16 hours, less than about 17 hours, less than about 18 hours, less than about 19 hours, less than about 20 hours, less than about 21 hours, less than about 22 hours, less than about 23 hours, less than about 24 hours, less than about 25 hours, less than about 26 hours, less than about 27 hours, less than about 28 hours, less than about 29 hours, less than about 30 hours, less than about 31 hours, less than about 32 hours, less than about 33 hours, less than about 34 hours, less than about 35 hours, less than about 36 hours, less than about 37 hours, less than about 38 hours, less than about 39 hours, less than about 40 hours, less than about 41 hours, less than about 42 hours, less than about 43 hours, less than about 44 hours, less than about 45 hours, less than about 50 hours, less than about 55 hours, less than about 60 hours, less than about 65 hours, less than about 70 hours, less than about 75 hours, less than about 80 hours, less than about 85 hours, less than about 90 hours, less than about 95 hours, or less than about 100 hours.

Stability

In some embodiments, the composition is stable from about −20° C. to about 25° C. In some embodiments, the composition is stable from about 5° C. to about 25° C. In some embodiments, the composition is stable at about −20° C. In some embodiments, the composition is stable at about −15° C. In some embodiments, the composition is stable at about −10° C. In some embodiments, the composition is stable at about −5° C. In some embodiments, the composition is stable at about 0° C. In some embodiments, the composition is stable at about 5° C. In some embodiments, the composition is stable at about 6° C. In some embodiments, the composition is stable at about 7° C. In some embodiments, the composition is stable at about 8° C. In some embodiments, the composition is stable at about 9° C. In some embodiments, the composition is stable at about 10° C. In some embodiments, the composition is stable at about 11° C. In some embodiments, the composition is stable at about 12° C. In some embodiments, the composition is stable at about 13° C. In some embodiments, the composition is stable at about 14° C. In some embodiments, the composition is stable at about 15° C. In some embodiments, the composition is stable at about 16° C. In some embodiments, the composition is stable at about 17° C. In some embodiments, the composition is stable at about 18° C. In some embodiments, the composition is stable at about 19° C. In some embodiments, the composition is stable at about 20° C. In some embodiments, the composition is stable at about 21° C. In some embodiments, the composition is stable at about 22° C. In some embodiments, the composition is stable at about 23° C. In some embodiments, the composition is stable at about 24° C. In some embodiments, the composition is stable at about 25° C. In some embodiments, the composition is stable at about −20° C., about 5° C., or about 25° C.

In some embodiments, the compositions disclosed herein are stable for at least about 3 months to about 2 years. In some embodiments, the composition disclosed herein is stable for at least about 3 months. In some embodiments, the composition disclosed herein is stable for at least about 4 months. In some embodiments, the composition disclosed herein is stable for at least about 5 months. In some embodiments, the composition disclosed herein is stable for at least about 6 months. In some embodiments, the composition disclosed herein is stable for at least about 7 months.

In some embodiments, the composition disclosed herein is stable for at least about 8 months. In some embodiments, the composition disclosed herein is stable for at least about 9 months. In some embodiments, the composition disclosed herein is stable for at least about 10 months. In some embodiments, the composition disclosed herein is stable for at least about 11 months. In some embodiments, the composition disclosed herein is stable for at least about 12 months. In some embodiments, the composition disclosed herein is stable for at least about 13 months. In some embodiments, the composition disclosed herein is stable for at least about 14 months. In some embodiments, the composition disclosed herein is stable for at least about 15 months. In some embodiments, the composition disclosed herein is stable for at least about 16 months. In some embodiments, the composition disclosed herein is stable for at least about 17 months. In some embodiments, the composition is stable for at least about 18 months. In some embodiments, the composition disclosed herein is stable for at least about 19 months. In some embodiments, the composition disclosed herein is stable for at least about 20 months. In some embodiments, the composition disclosed herein is stable for at least about 21 months. In some embodiments, the composition disclosed herein is stable for at least about 22 months. In some embodiments, the composition disclosed herein is stable for at least about 23 months. In some embodiments, the composition disclosed herein is stable for at least about 24 months (2 years). In some embodiments, the composition disclosed herein is stable for at least about 36 months (3 years). In some embodiments, the composition disclosed herein is stable for at least about 48 months (4 years).

In some embodiments, the compositions described are compositions that have minimal degradation of the caspofungin, or a polymorph, pharmaceutically acceptable salt, hydrate, or solvate after storage conditions. In some embodiments, the minimal degradation of the caspofungin, or a polymorph, pharmaceutically acceptable salt, hydrate, or solvate after storage conditions is attributed to the compositions further comprising stability-enhancing salts, such as chloride salts or phosphate salts. In some embodiments, the stability-enhancing salts are from the vehicles used to prepare the pre-lyophilized solutions containing caspofungin, or a polymorph, pharmaceutically acceptable salt, hydrate or solvent and polyvinylpyrrolidone. The pre-lyophilized solutions are then lyophilized to provide solid compositions, which are then stored under appropriate conditions prior to use. In some embodiments, the solid compositions are reconstituted with an appropriate solvent to provide a solution that is then administered to a subject in need thereof.

In some embodiments, the composition comprises from about 95% to about 99.99% of caspofungin, or a polymorph, pharmaceutically acceptable salt, hydrate, or solvate thereof that has not degraded after storage at about a specific temperature for about a specific amount of time. In some embodiments, the composition comprises greater than about 95% of caspofungin, or a polymorph, pharmaceutically acceptable salt, hydrate, or solvate thereof that has not degraded after storage at about a specific temperature for about a specific amount of time. In some embodiments, the composition comprises greater than about 96% of caspofungin, or a polymorph, pharmaceutically acceptable salt, hydrate, or solvate thereof that has not degraded after storage at about a specific temperature for about a specific amount of time. In some embodiments, the composition comprises greater than about 97% of caspofungin, or a polymorph, pharmaceutically acceptable salt, hydrate, or solvate thereof that has not degraded after storage at about a specific temperature for about a specific amount of time. In some embodiments, the composition comprises greater than about 98% of caspofungin, or a polymorph, pharmaceutically acceptable salt, hydrate, or solvate thereof that has not degraded after storage at about a specific temperature for about a specific amount of time. In some embodiments, the composition comprises greater than about 99% of caspofungin, or a polymorph, pharmaceutically acceptable salt, hydrate, or solvate thereof that has not degraded after storage at about a specific temperature for about a specific amount of time. In some embodiments, the composition comprises greater than about 99.5% of caspofungin, or a polymorph, pharmaceutically acceptable salt, hydrate, or solvate thereof that has not degraded after storage at about a specific temperature for about a specific amount of time.

In some embodiments, the specific temperature is about −20° C., about 5° C., or about 25° C. In some embodiments, the specific amount of time is about 0 weeks, about 2 weeks, about 4 weeks, about 8 weeks, about 12 weeks, about 16 weeks, about 20 weeks, about 24 weeks, about 28 weeks, about 32 weeks, about 36 weeks, about 40 weeks, about 44 weeks, about 48 weeks, about 52 weeks, about 104 weeks, about 156 weeks, or about 208 weeks. In some embodiments, the specific amount of time is about 0 weeks, about 2 weeks, about 4 weeks, about 8 weeks, or about 12 weeks. In some embodiments, the specific temperature is about −20° C. and the specific amount of time is about 0 weeks. In some embodiments, the specific temperature is about −20° C. and the specific amount of time is about 2 weeks. In some embodiments, the specific temperature is about −20° C. and the specific amount of time is about 4 weeks. In some embodiments, the specific temperature is about −20° C. and the specific amount of time is about 8 weeks. In some embodiments, the specific temperature is about −20° C. and the specific amount of time is about 12 weeks. In some embodiments, the specific temperature is about −20° C. and the specific amount of time is about 24 weeks. In some embodiments, the specific temperature is about −20° C. and the specific amount of time is about 52 weeks.

In some embodiments, the specific temperature is about 5° C. and the specific amount of time is about 0 weeks. In some embodiments, the specific temperature is about 5° C. and the specific amount of time is about 2 weeks. In some embodiments, the specific temperature is about 5° C. and the specific amount of time is about 4 weeks. In some embodiments, the specific temperature is about 5° C. and the specific amount of time is about 8 weeks. In some embodiments, the specific temperature is about 5° C. and the specific amount of time is about 12 weeks. In some embodiments, the specific temperature is about 5° C. and the specific amount of time is about 24 weeks. In some embodiments, the specific temperature is about 5° C. and the specific amount of time is about 52 weeks.

In some embodiments, the specific temperature is about 25° C. and the specific amount of time is about 0 weeks. In some embodiments, the specific temperature is about 25° C. and the specific amount of time is about 2 weeks. In some embodiments, the specific temperature is about 25° C. and the specific amount of time is about 4 weeks. In some embodiments, the specific temperature is about 25° C. and the specific amount of time is about 8 weeks. In some embodiments, the specific temperature is about 25° C. and the specific amount of time is about 12 weeks. In some embodiments, the specific temperature is about 25° C. and the specific amount of time is about 24 weeks. In some embodiments, the specific temperature is about 25° C. and the specific amount of time is about 52 weeks.

In some embodiments, the composition comprises greater than about 95% of caspofungin, or a polymorph, pharmaceutically acceptable salt, hydrate, or solvate thereof that has not degraded after storage at about −20° C. for about 0 weeks, about 2 weeks, about 4 weeks, about 8 weeks, about 12 weeks, about 24 weeks or about 52 weeks.

In some embodiments, the composition comprises greater than about 95% of caspofungin, or a polymorph, pharmaceutically acceptable salt, hydrate, or solvate thereof that has not degraded after storage at about 5° C. for about 0 weeks, about 2 weeks, about 4 weeks, about 8 weeks, about 12 weeks, about 24 weeks or about 52 weeks.

In some embodiments, the composition comprises greater than about 95% caspofungin, or a polymorph, pharmaceutically acceptable salt, hydrate, or solvate thereof that has not degraded after storage at about 25° C. after about 0 weeks, about 2 weeks, about 4 weeks, about 8 weeks, about 12 weeks, about 24 weeks or about 52 weeks.

In some embodiments, the degradation products of caspofungin, or a polymorph, pharmaceutically acceptable salt, hydrate, or solvate thereof for any one of the compositions described herein is characterized and measured by HPLC analysis after storage under specified conditions.

In some embodiments, the degradation product of caspofungin, or a polymorph, pharmaceutically acceptable salt, hydrate, or solvate thereof is the hydrolysis degradation product, which has a HPLC retention time of about 26.1 minutes. In some embodiments, the composition comprises less than about 30% of the hydrolysis degradation product after storage at a specific temperature and for a specific amount of time. In some embodiments, the composition comprises less than about 20% of the hydrolysis degradation product after storage at a specific temperature and for a specific amount of time. In some embodiments, the composition comprises less than about 15% of the hydrolysis degradation product after storage at a specific temperature and for a specific amount of time. In some embodiments, the composition comprises less than about 10% of the hydrolysis degradation product after storage at a specific temperature and for a specific amount of time. In some embodiments, the composition comprises less than about 5% of the hydrolysis degradation product after storage at a specific temperature and for a specific amount of time. In some embodiments, the composition comprises less than about 4% of the hydrolysis degradation product after storage at a specific temperature and for a specific amount of time. In some embodiments, the composition comprises less than about 3% of the hydrolysis degradation product after storage at a specific temperature and for a specific amount of time. In some embodiments, the composition comprises less than about 2% of the hydrolysis degradation product after storage at a specific temperature and for a specific amount of time. In some embodiments, the composition comprises less than about 1% of the hydrolysis degradation product after storage at a specific temperature and for a specific amount of time. In some embodiments, the composition comprises less than about 0.5% of the hydrolysis degradation product after storage at a specific temperature and for a specific amount of time. In some embodiments, the composition comprises less than about 0.1% of the hydrolysis degradation product after storage at a specific temperature and for a specific amount of time.

In some embodiments, the degradation product of caspofungin, or a polymorph, pharmaceutically acceptable salt, hydrate, or solvate thereof is the dimerization degradation product, which has a HPLC retention time of about 37.3 minutes. In some embodiments, the composition comprises less than about 30% of the dimerization degradation product after storage at a specific temperature and for a specific amount of time. In some embodiments, the composition comprises less than about 20% of the dimerization degradation product after storage at a specific temperature and for a specific amount of time. In some embodiments, the composition comprises less than about 15% of the dimerization degradation product after storage at a specific temperature and for a specific amount of time. In some embodiments, the composition comprises less than about 10% of the dimerization degradation product after storage at a specific temperature and for a specific amount of time. In some embodiments, the composition comprises less than about 5% of the dimerization degradation product after storage at a specific temperature and for a specific amount of time. In some embodiments, the composition comprises less than about 4% of the dimerization degradation product after storage at a specific temperature and for a specific amount of time. In some embodiments, the composition comprises less than about 3% of the dimerization degradation product after storage at a specific temperature and for a specific amount of time. In some embodiments, the composition comprises less than about 2% of the dimerization degradation product after storage at a specific temperature and for a specific amount of time. In some embodiments, the composition comprises less than about 1% of the dimerization degradation product after storage at a specific temperature and for a specific amount of time. In some embodiments, the composition comprises less than about 0.5% of the dimerization degradation product after storage at a specific temperature and for a specific amount of time. In some embodiments, the composition comprises less than about 0.1% of the dimerization degradation product after storage at a specific temperature and for a specific amount of time.

In some embodiments, the specific temperature is about −20° C., about 5° C., or about 25° C. In some embodiments, the specific amount of time is about 0 weeks, about 2 weeks, about 4 weeks, about 8 weeks, about 12 weeks, about 16 weeks, about 20 weeks, about 24 weeks, about 28 weeks, about 32 weeks, about 36 weeks, about 40 weeks, about 44 weeks, about 48 weeks, about 52 weeks, about 104 weeks, about 156 weeks, or about 208 weeks. In some embodiments, the specific amount of time is about 0 weeks, about 2 weeks, about 4 weeks, about 8 weeks, about 12 weeks, about 24 weeks or about 52 weeks.

In some embodiments, the specific temperature is about −20° C. and the specific amount of time is about 0 weeks. In some embodiments, the specific temperature is about −20° C. and the specific amount of time is about 2 weeks. In some embodiments, the specific temperature is about −20° C. and the specific amount of time is about 4 weeks. In some embodiments, the specific temperature is about −20° C. and the specific amount of time is about 8 weeks. In some embodiments, the specific temperature is about −20° C. and the specific amount of time is about 12 weeks. In some embodiments, the specific temperature is about −20° C. and the specific amount of time is about 24 weeks. In some embodiments, the specific temperature is about −20° C. and the specific amount of time is about 52 weeks.

In some embodiments, the specific temperature is about 5° C. and the specific amount of time is about 0 weeks. In some embodiments, the specific temperature is about 5° C. and the specific amount of time is about 2 weeks. In some embodiments, the specific temperature is about 5° C. and the specific amount of time is about 4 weeks. In some embodiments, the specific temperature is about 5° C. and the specific amount of time is about 8 weeks. In some embodiments, the specific temperature is about 5° C. and the specific amount of time is about 12 weeks. In some embodiments, the specific temperature is about 5° C. and the specific amount of time is about 24 weeks. In some embodiments, the specific temperature is about 5° C. and the specific amount of time is about 52 weeks.

In some embodiments, the specific temperature is about 25° C. and the specific amount of time is about 0 weeks. In some embodiments, the specific temperature is about 25° C. and the specific amount of time is about 2 weeks. In some embodiments, the specific temperature is about 25° C. and the specific amount of time is about 4 weeks. In some embodiments, the specific temperature is about 25° C. and the specific amount of time is about 8 weeks. In some embodiments, the specific temperature is about 25° C. and the specific amount of time is about 12 weeks. In some embodiments, the specific temperature is about 25° C. and the specific amount of time is about 24 weeks. In some embodiments, the specific temperature is about 25° C. and the specific amount of time is about 52 weeks.

Reconstituted Solution Stability

In some embodiments, the composition is a reconstituted solution. In some embodiments, the reconstituted solution comprises from about 95% to about 99.99% of caspofungin, or a polymorph, pharmaceutically acceptable salt, hydrate, or solvate thereof that has not degraded after storage at about a specific temperature for about a specific amount of time. In some embodiments, the reconstituted solution comprises greater than about 95% of caspofungin, or a polymorph, pharmaceutically acceptable salt, hydrate, or solvate thereof that has not degraded after storage at about a specific temperature for about a specific amount of time. In some embodiments, the reconstituted solution comprises greater than about 96% of caspofungin, or a polymorph, pharmaceutically acceptable salt, hydrate, or solvate thereof that has not degraded after storage at about a specific temperature for about a specific amount of time. In some embodiments, the reconstituted solution comprises greater than about 97% of caspofungin, or a polymorph, pharmaceutically acceptable salt, hydrate, or solvate thereof that has not degraded after storage at about a specific temperature for about a specific amount of time. In some embodiments, the reconstituted solution comprises greater than about 98% of caspofungin, or a polymorph, pharmaceutically acceptable salt, hydrate, or solvate thereof that has not degraded after storage at about a specific temperature for about a specific amount of time. In some embodiments, the reconstituted solution comprises greater than about 99% of caspofungin, or a polymorph, pharmaceutically acceptable salt, hydrate, or solvate thereof that has not degraded after storage at about a specific temperature for about a specific amount of time. In some embodiments, the reconstituted solution comprises greater than about 99.5% of caspofungin, or a polymorph, pharmaceutically acceptable salt, hydrate, or solvate thereof that has not degraded after storage at about a specific temperature for about a specific amount of time.

In some embodiments, the specific temperature is about −20° C., about 5° C., or about 25° C. In some embodiments, the specific amount of time is about 0 hours, about 24 hours, about 48 hours, about 72 hours, about 96 hours, about 120 hours, about 144 hours, about 1 week, about 4 weeks, about 8 weeks, about 12 weeks, about 16 weeks, about 20 weeks, about 24 weeks, about 28 weeks, about 32 weeks, about 36 weeks, about 40 weeks, about 44 weeks, about 48 weeks, about 52 weeks, about 104 weeks, about 156 weeks, or about 208 weeks. In some embodiments, the specific amount of time is about 0 hours, about 24 hours, about 48 hours, about 72 hours, about 96 hours, about 120 hours, about 144 hours, about 1 week, about 4 weeks, about 8 weeks, or about 12 weeks.

In some embodiments, the specific temperature is about 5° C. and the specific amount of time is about 24 hours. In some embodiments, the specific temperature is about 5° C. and the specific amount of time is about 48 hours. In some embodiments, the specific temperature is about 5° C. and the specific amount of time is about 72 hours. In some embodiments, the specific temperature is about 5° C. and the specific amount of time is about 96 hours. In some embodiments, the specific temperature is about 5° C. and the specific amount of time is about 168 hours. In some embodiments, the specific temperature is about 5° C. and the specific amount of time is about 240 hours.

In some embodiments, the specific temperature is about 25° C. and the specific amount of time is about 1 hours. In some embodiments, the specific temperature is about 25° C. and the specific amount of time is about 4 hours. In some embodiments, the specific temperature is about 25° C. and the specific amount of time is about 7 hours.

In some embodiments, the reconstituted solution comprises greater than about 95% of caspofungin, or a polymorph, pharmaceutically acceptable salt, hydrate, or solvate thereof that has not degraded after storage at about 5° C. about 0 hours, about 24 hours, about 48 hours, about 72 hours, or about 96 hours.

In some embodiments, the reconstituted solution comprises greater than about 95% caspofungin, or a polymorph, pharmaceutically acceptable salt, hydrate, or solvate thereof that has not degraded after storage at about 25° C. after about 0 hours, about 24 hours, about 48 hours, about 72 hours, about 96 hours, about 168 hours or about 240 hours.

pH

In some embodiments, the composition has a pH from about 4.0 to about 8.5. In some embodiments, the composition has a pH from about 4.0 to about 7.5. In some embodiments, the composition has a pH from about 5.0 to about 7.0. In some embodiments, the composition has a pH from about 5.0 to about 8.5. In some embodiments, the composition has a pH from about 6.0 to about 7.5. In some embodiments, the composition has a pH from about 7.0 to about 7.5. In some embodiments, the composition has a pH of about 4.0. In some embodiments, the composition has a pH of about 4.5. In some embodiments, the composition has a pH of about 5.0. In some embodiments, the composition has a pH of about 5.5. In some embodiments, the composition has a pH of about 6.0. In some embodiments, the composition has a pH of about 6.5. In some embodiments, the composition has a pH of about 7.0. In some embodiments, the composition has a pH of about 7.5. In some embodiments, the composition has a pH of about 8.0. In some embodiments, the composition has a pH of about 8.5.

Methods of Treatment

Described herein is a method of preventing or treating a fungal infection in the pulmonary system of a subject in need thereof comprising administering to the subject a composition comprising caspofungin, or a polymorph, pharmaceutically acceptable salt, hydrate, or solvate thereof, and polyvinylpyrrolidone (PVP).

Pulmonary Infections

Disclosed herein is a method for the prevention or treatment of a pulmonary infection in the pulmonary system. In some embodiments, the method is for treating a fungal infection caused by *Candida* sp., and/or by *Aspergillus* sp., and/or by *Pneumocystis jirovecii*. In some embodiments, the method is for treating an infection caused by *Candida* sp., and/or by *Aspergillus* sp. In some embodiments, the method is for treating a fungal infection caused by *Candida albicans*, *Candida tropicalis*, *Candida krusei*, *Candida glabrata*, *Candida guilliermondii*, or *Candida parapsilosis*. In some embodiments, the method is for treating a fungal infection caused by *Candida albicans*, *Candida tropicalis*, *Candida krusei*, or *Candida glabrata*. In some embodiments, the method for treating a fungal infection caused by *Aspergillus fumigatus*, *Aspergillus flavus*, *Aspergillus niger*, or *Aspergillus terreus*. In some embodiments, the method for treating a fungal infection is caused by *Aspergillus fumigatus*, *Aspergillus flavus*, or *Aspergillus niger*.

In some embodiments, the method is for preventing a fungal infection caused by *Candida* sp., and/or by *Aspergillus* sp., and/or by *Pneumocystis jirovecii*. In some embodiments, the method is for preventing an infection caused by *Candida* sp., and/or by *Aspergillus* sp. In some embodiments, the method is for treating a fungal infection caused by *Candida albicans*, *Candida tropicalis*, *Candida krusei*, *Candida glabrata*, *Candida guilliermondii*, or *Candida parapsilosis*. In some embodiments, the method is for preventing a fungal infection caused by *Candida albicans*, *Candida tropicalis*, *Candida krusei*, or *Candida glabrata*. In some embodiments, the method for treating a fungal infection caused by *Aspergillus fumigatus*, *Aspergillus flavus*, *Aspergillus niger*, or *Aspergillus terreus*. In some embodiments, the method for preventing a fungal infection is caused by *Aspergillus fumigatus*, *Aspergillus flavus*, or *Aspergillus niger*.

In some embodiments, the subject is immunocompromised. In some embodiments, the subject is a transplant recipient or a subject undergoing cancer chemotherapy. In some embodiments, the subject is a transplant recipient. In some embodiments, the subject is undergoing cancer chemotherapy. In some embodiments, the subject is a recipient of a hematopoietic stem-cell transplant, bone marrow transplant, lung transplant, liver transplant, heart transplant, kidney transplant, pancreas transplant or a combination thereof. In some embodiments, the subject is a recipient of a hematopoietic stem-cell transplant. In some embodiments, the subject is a recipient of a bone marrow transplant. In some embodiments, the subject is a recipient of a lung transplant. In some embodiments, the subject is a recipient of a liver transplant. In some embodiments, the subject is a recipient of a heart transplant. In some embodiments, the subject is a recipient of a kidney transplant. In some embodiments, the subject is a recipient of a pancreas transplant.

Kits

Also provided herein is a kit comprising: a) a first container comprising a solid composition suitable for inhalation administration, wherein the composition comprises i) caspofungin, or a polymorph, pharmaceutically acceptable salt, hydrate, or solvate thereof, and ii) polyvinylpyrrolidone (PVP); and b) a second container comprising a solution for reconstituting the solid composition.

In some embodiments, the kit further comprises an inhalation device. In some embodiments, the solid composition suitable for inhalation administration is a lyophilized composition. In some embodiments, the composition further comprises at least one stability-enhancing salt. In some embodiments, the solution for reconstituting the solid composition is water, saline, or phosphate-buffered saline (PBS). In some embodiments, the solution for reconstituting the solid composition is water. In some embodiments, the solution for reconstituting the solid composition is saline. In some embodiments, the solution for reconstituting the solid composition is phosphate-buffered saline (PBS).

In some embodiments, the kit is used for preventing or treating a fungal infection in the pulmonary system of a subject. In some embodiments, the kit is used for preventing a fungal infection in the pulmonary system of a subject. In some embodiments, the kit is used for treating a fungal infection in the pulmonary system of a subject.

In some embodiments, the kit is for treating a fungal infection caused by *Candida* sp., and/or by *Aspergillus* sp., and/or by *Pneumocystis jirovecii*. In some embodiments, the kit is for treating an infection caused by *Candida* sp., and/or by *Aspergillus* sp. In some embodiments, the kit is for treating a fungal infection caused by *Candida albicans*, *Candida tropicalis*, *Candida krusei*, *Candida glabrata*, *Candida guilliermondii*, or *Candida parapsilosis*. In some embodiments, the kit is for treating a fungal infection caused by *Candida albicans*, *Candida tropicalis*, *Candida krusei*, or *Candida glabrata*. In some embodiments, the kit for treating a fungal infection caused by *Aspergillus fumigatus*, *Aspergillus flavus*, *Aspergillus niger*, or *Aspergillus terreus*. In some embodiments, the kit is for treating a fungal infection caused by *Aspergillus fumigatus*, *Aspergillus flavus*, or *Aspergillus niger*.

In some embodiments, kit is for preventing a fungal infection caused by *Candida* sp., and/or by *Aspergillus* sp., and/or by *Pneumocystis jirovecii*. In some embodiments, the kit is for preventing an infection caused by *Candida* sp., and/or by *Aspergillus* sp. In some embodiments, the kit is for treating a fungal infection caused by *Candida albicans*, *Candida tropicalis*, *Candida krusei*, *Candida glabrata*, *Candida guilliermondii*, or *Candida parapsilosis*. In some embodiments, the kit is for preventing a fungal infection caused by *Candida albicans*, *Candida tropicalis*, *Candida krusei*, or *Candida glabrata*. In some embodiments, the kit for treating a fungal infection caused by *Aspergillus fumigatus*, *Aspergillus flavus*, *Aspergillus niger*, or *Aspergillus terreus*. In some embodiments, the kit is for preventing a fungal infection caused by *Aspergillus fumigatus*, *Aspergillus flavus*, or *Aspergillus niger*.

Methods of Preparation

Also provided herein is a method for preparing a composition suitable for inhalation administration comprising: a) forming a liquid solution comprising i) caspofungin, or a polymorph, pharmaceutically acceptable salt, hydrate, or solvate thereof, ii) polyvinylpyrrolidone (PVP); iii) a vehicle; and iv) optionally, a pH modifier to form a pre-lyophilized solution; and b) lyophilizing the pre-lyophilized solution to provide the composition suitable for inhalation administration.

In some embodiments, the pH modifier is sodium hydroxide or acetic acid. In some embodiments, the vehicle is water, saline, or phosphate buffered-saline. In some embodiments, the vehicle has a volume of from about 0.1 mL to about 3 mL. In some embodiments, the pre-lyophilized solution from step a) is sterilized by filtration.

EMBODIMENTS

In some cases, the present disclosure provides compositions, methods, and kits consistent with the following embodiments:

1. A composition suitable for inhalation administration comprising
   i) caspofungin, or a polymorph, pharmaceutically acceptable salt, hydrate, or solvate thereof;
   ii) polyvinylpyrrolidone (PVP); and
   iii) at least one stability-enhancing salt.

2. The composition of embodiment 1, wherein the at least one stability-enhancing salt is sodium chloride, potassium chloride, or a combination thereof.

3. The composition of embodiment 2, wherein the at least one stability-enhancing salt further comprises sodium phosphate, potassium phosphate, or a combination thereof 4. The composition of embodiment 3, wherein the sodium phosphate is disodium hydrogen phosphate, and the potassium phosphate is potassium dihydrogen phosphate.

5. A composition suitable for inhalation administration comprising
   i) caspofungin, or a polymorph, pharmaceutically acceptable salt, hydrate, or solvate thereof; and
   ii) polyvinylpyrrolidone (PVP);
   wherein the composition comprises greater than about 95% of caspofungin, or a polymorph, pharmaceutically acceptable salt, hydrate, or solvate thereof that has not degraded after storage at about −20° C., 5° C., or 25° C. for about 0 weeks, about 2 weeks, about 4 weeks, about 8 weeks, or about 12 weeks.

6. A composition suitable for inhalation administration comprising
   i) caspofungin, or a polymorph, pharmaceutically acceptable salt, hydrate, or solvate thereof; and
   ii) polyvinylpyrrolidone (PVP);
   wherein the composition is a lyophilized composition that comprises less than about 2% by weight of water.

7. A composition suitable for inhalation administration comprising
   i) caspofungin, or a polymorph, pharmaceutically acceptable salt, hydrate, or solvate thereof; and
   ii) polyvinylpyrrolidone (PVP);
   wherein the concentration of caspofungin, or the polymorph, pharmaceutically acceptable salt, hydrate, or solvate thereof, in a lung is greater than about 5 µg/g for about 0.5 hour to about 24 hours.

8. The composition of embodiment 7, wherein the concentration of caspofungin, or the polymorph, pharmaceutically acceptable salt, hydrate, or solvate thereof, in the lung is greater than about 12 µg/g for about 0.5 hour to about 2 hours.

9. A composition suitable for inhalation administration comprising
   i) caspofungin, or a polymorph, pharmaceutically acceptable salt, hydrate, or solvate thereof; and
   ii) polyvinylpyrrolidone (PVP).

10. The composition of any one of embodiments 1-9, wherein the composition is essentially free of mannitol.

11. The composition of embodiment 10, wherein the composition is essentially free of sugar alcohol.

12. The composition of embodiment 10, wherein the composition is essentially free of sugar alcohol or sugar.

13. The composition of any one of embodiments 1-12, wherein the pharmaceutically acceptable salt of caspofungin is the acetate salt.

14. The composition of embodiment 13, wherein the composition comprises from about 1 mg to about 100 mg of caspofungin acetate.

15. The composition of any one of embodiments 1-14, wherein the weight ratio of polyvinylpyrrolidone (PVP) to caspofungin, or the polymorph, pharmaceutically acceptable salt, hydrate, or solvate thereof, is from about 10:1 to about 1:1.

16. The composition of embodiment 15, wherein the weight ratio of polyvinylpyrrolidone (PVP) to caspofungin, or the polymorph, pharmaceutically acceptable salt, hydrate, or solvate thereof is about 6:1 about 4:1, about 2:1, or about 1:1.

17. The composition of any one of embodiments 2-16, wherein the composition further comprises at least one stability-enhancing salt.

18. The composition of embodiment 17, wherein the at least one stability-enhancing salt is sodium chloride, potassium chloride, or a combination thereof 19. The composition of embodiment 18, wherein the at least one stability-enhancing salt further comprises sodium phosphate, potassium phosphate, or a combination thereof 20. The composition of embodiment 19, wherein the sodium phosphate is disodium hydrogen phosphate, and the potassium phosphate is potassium dihydrogen phosphate.

21. The composition of any one of embodiments 1-20, wherein the composition further comprises a pH modifier.

22. The composition of embodiment 21, wherein the pH modifier is sodium hydroxide or acetic acid.

23. The composition of any one of embodiments 1-22, wherein the composition has a pH of from about 5 to about 7.

24. The composition of embodiment 23, wherein the composition has a pH of about 6.

25. The composition of any one of embodiments 1-24, wherein the composition further comprises a vehicle.

26. The composition of embodiment 25, wherein the vehicle is water, saline, or phosphate-buffered saline.

27. The composition of embodiment 25 or embodiment 26, wherein the vehicle has a volume of from about 0.1 mL to about 3 mL.

28. The composition of any one of embodiments 1-5 and 7-27, wherein the composition is a pre-lyophilized composition.

29. The composition of embodiment 28, wherein the pre-lyophilized composition is sterilized by filtration.

30. The composition of any one of embodiments 1-27, wherein the composition is a lyophilized composition.

31. The composition of embodiment 30, wherein the lyophilized composition comprises less than about 2% by weight of water.

32. The composition of embodiment 31, wherein the lyophilized composition is reconstituted with water, saline, or phosphate-buffered saline (PBS) to provide a reconstituted solution.

33. The composition of embodiment 32, wherein the reconstituted solution comprises greater than about 95% of caspofungin, or a polymorph, pharmaceutically acceptable salt, hydrate, or solvate thereof that has not degraded after storage at about −20° C., 5° C., or 25° C. for about 0 hours, about 24 hours, about 48 hours, about 72 hours, about 96 hours, about 120 hours, about 144 hours, about 1 week, about 4 weeks, about 8 weeks, or about 12 weeks.

34. The composition of any one of embodiments 1-33, wherein the administration of the composition provides a lung tissue concentration of caspofungin, or the polymorph, pharmaceutically acceptable salt, hydrate, or solvate thereof, that is from about 1-fold to about 100-fold greater than intravenous administration at the same delivery dose.

35. The composition of embodiment 34, wherein the lung tissue concentration of caspofungin, or the polymorph, pharmaceutically acceptable salt, hydrate, or solvate thereof, is greater than intravenous administration at the same delivery dose for about 0.5 hour to about 168 hours.

36. The composition of any one of embodiments 1-35, wherein the administration of the composition provides a lung tissue concentration of caspofungin, or the polymorph, pharmaceutically acceptable salt, hydrate, or solvate thereof, that is from about 1-fold to about 50-fold greater than intravenous administration at the same delivery dose.

37. The composition of embodiment 36, wherein the lung tissue concentration of caspofungin, or the polymorph, pharmaceutically acceptable salt, hydrate, or solvate thereof, is greater than intravenous administration at the same delivery dose for about 0.5 hour to about 168 hours.

38. The composition of any one of embodiments 1-37, wherein the administration of the composition provides a concentration of caspofungin, or the polymorph, pharmaceutically acceptable salt, hydrate, or solvate thereof, in the lung that is from about 1-fold greater to about 1000-fold greater than a concentration of caspofungin, or the polymorph, pharmaceutically acceptable salt, hydrate, or solvate thereof, in the liver, kidney, or plasma.

39. The composition of embodiment 38, wherein the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 0.5 hour to about 168 hours.

40. The composition of any one of embodiments 1-39, wherein the administration of the composition provides a concentration of caspofungin, or the polymorph, pharmaceutically acceptable salt, hydrate, or solvate thereof, in the lung that is from about 1-fold greater to about 350-fold greater than a concentration of caspofungin, or the polymorph, pharmaceutically acceptable salt, hydrate, or solvate thereof, in the liver, kidney, or plasma.

41. The composition of any one of embodiments 1-39, wherein the administration of the composition provides a concentration of caspofungin, or the polymorph, pharmaceutically acceptable salt, hydrate, or solvate thereof, in the lung that is from about 1-fold greater to about 150-fold greater than a concentration of caspofungin, or the polymorph, pharmaceutically acceptable salt, hydrate, or solvate thereof, in the liver, kidney, or plasma.

42. The composition of embodiment 40 or embodiment 41, wherein the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 0.5 hour to about 168 hours.

43. The composition of any one of embodiments 1-42, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 3 hours after administration.

44. The composition of any one of embodiments 1-43, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 12 hours after administration.

45. The composition of any one of embodiments 1-44, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 24 hours after administration.

46. The composition of any one of embodiments 1-45, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 48 hours after administration.

47. The composition of any one of embodiments 1-46, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 72 hours after administration.

48. The composition of any one of embodiments 1-47, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 96 hours after administration.

49. The composition of any one of embodiments 1-48, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 120 hours after administration.

50. The composition of any one of embodiments 1-49, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 144 hours after administration.

51. The composition of any one of embodiments 1-50, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 168 hours after administration.

52. The composition of any one of embodiments 43-51, wherein the minimum inhibitory concentration (MIC) is from about 0.001 µg/mL to about 128 µg/mL.

53. The composition of any one of embodiments 43-51, wherein the minimum inhibitory concentration (MIC) is from about 0.001 µg/mL to about 32 µg/mL.

54. The composition of any one of embodiments 43-51, wherein the minimum effective concentration (MEC) is from about 0.001 µg/mL to about 128 µg/mL.

55. The composition of any one of embodiments 43-51, wherein the minimum inhibitory concentration (MEC) is from about 0.001 µg/mL to about 32 µg/mL.

56. The composition of any one of embodiments 1-6 and 9-55, wherein the concentration of caspofungin, or the polymorph, pharmaceutically acceptable salt, hydrate, or solvate thereof, in the lung is greater than about 5 µg/g for about 0.5 hour to about 24 hours.

57. The composition of any one of embodiments 1-6 and 9-55, wherein the concentration of caspofungin, or the polymorph, pharmaceutically acceptable salt, hydrate, or solvate thereof, in the lung is greater than about 12 µg/g for about 0.5 hour to about 2 hours.

58. The composition of any one of embodiments 1-57, wherein the composition is administered with an inhalation device selected from a jet nebulizer, ultrasonic wave nebulizer, high efficiency nebulizer, heat vaporizer, soft mist inhaler, thermal aerosol inhaler, or electrohydrodynamic-based solution misting inhaler.

59. The composition of embodiment 58, wherein the composition is administered by the inhalation device as droplets or particles having a mass median aerodynamic diameter (MMAD) from about 0.1 µm to about 10 µm.

60. The composition of embodiment 58, wherein the composition is administered by the inhalation device as droplets or particles having a mass median aerodynamic diameter (MMAD) from about 0.1 µm to about 5 µm.

61. The composition of embodiment 59 or embodiment 60, wherein the droplets or particles have a geometric standard deviation (GSD) from about 2.0 to about 6.0.

62. The composition of any one of embodiments 1-61, wherein the half-life of the caspofungin, or a polymorph, pharmaceutically acceptable salt, hydrate, or solvate thereof, in the lung is about 1 hour to about 50 hours.

63. The composition of any one of embodiments 1-61, wherein the half-life of the caspofungin, or a polymorph, pharmaceutically acceptable salt, hydrate, or solvate thereof, in the lung is about 20 hours to about 50 hours.

64. The composition of any one of embodiments 1-63, wherein the composition is stable from at about −20° C. to about 25° C.

65. The composition of embodiment 64, wherein the composition is stable from at about −20° C., about 5° C., or about 25° C.

66. The composition of any one of embodiments 1-65, wherein the composition is stable for at least about 3 months to about 2 years.

67. The composition of any one of embodiments 1-66, wherein the composition comprises greater than about 95% of caspofungin, or a polymorph, pharmaceutically acceptable salt, hydrate, or solvate thereof, that has not degraded after storage at about −20° C. for about 0 weeks, about 2 weeks, about 4 weeks, about 8 weeks, or about 12 weeks.

68. The composition of any one of embodiments 1-66, wherein the composition comprises greater than about 95% of caspofungin, or a polymorph, pharmaceutically acceptable salt, hydrate, or solvate thereof, that has not degraded after storage at about 5° C. for about 0 weeks, about 2 weeks, about 4 weeks, about 8 weeks, or about 12 weeks.

69. The composition of any one of embodiments 1-66, wherein the composition comprises greater than about 95% caspofungin, or a polymorph, pharmaceutically acceptable salt, hydrate, or solvate thereof, that has not degraded after storage at about 25° C. after about 0 weeks, about 2 weeks, about 4 weeks, about 8 weeks, or about 12 weeks.

70. The composition of any one of embodiments 1-69, wherein the composition provides an increase of greater than about 50% of caspofungin, or a polymorph, pharmaceutically acceptable salt, hydrate, or solvate thereof, deposit in the lung without increasing systemic exposure when compared to a composition that does not comprise polyvinylpyrrolidone (PVP).

71. A method of preventing or treating a fungal infection in the pulmonary system of a subject in need thereof comprising administering to the subject a composition of any one of embodiments 1-70.

72. The method of embodiment 71, wherein the method is for treating a fungal infection caused by *Candida* sp., and/or by *Aspergillus* sp., and/or by *Pneumocystis jirovecii*.

73. The method of embodiment 71, wherein the method is for preventing a fungal infection caused by *Candida* sp., and/or by *Aspergillus* sp., and/or by *Pneumocystis jirovecii*.

74. A kit comprising:
   a) a first container comprising a solid composition suitable for inhalation administration, wherein the composition comprises i) caspofungin, or a polymorph, pharmaceutically acceptable salt, hydrate, or solvate thereof, and ii) polyvinylpyrrolidone (PVP); and
   b) a second container comprising a solution for reconstituting the solid composition.

75. The kit of embodiment 74, wherein the kit further comprises an inhalation device.

76. The kit of embodiment 74 or embodiment 75, wherein the solid composition suitable for inhalation administration is a lyophilized composition.

77. The kit of any one of embodiments 74-76, wherein the solution for reconstituting the solid composition is water, saline or phosphate-buffered saline (PBS).

78. A method for preparing a composition suitable for inhalation administration comprising
   a) forming a liquid solution comprising i) caspofungin, or a polymorph, pharmaceutically acceptable salt, hydrate, or solvate thereof; ii) polyvinylpyrrolidone (PVP); iii) a vehicle; and iv) optionally, a pH modifying agent to form a pre-lyophilized solution; and
   b) lyophilizing the pre-lyophilized solution to provide the composition suitable for inhalation administration.

79. The method of embodiment 78, wherein the pre-lyophilized solution from step a) is sterilized by filtration.

80. The composition of embodiment 16, wherein the weight ratio of polyvinylpyrrolidone (PVP) to caspofungin, or the polymorph, pharmaceutically acceptable salt, hydrate, or solvate thereof is about 4:1.

Other embodiments and uses will be apparent to one skilled in the art in light of the present disclosures. The following examples are provided merely as illustrative of various embodiments and shall not be construed to limit the present disclosure in any way.

EXAMPLES

Example 1: Aerosolization Studies

Objective: The objective of this study was to determine the suitability of various formulations with different combination of caspofungin diacetate and polyvinylpyrrolidone (PVP K30) based on their aerosolization potential. The stock solutions of caspofungin diacetate (100 mg/mL) and polyvinylpyrrolidone (PVP K30, 100 mg/mL) were prepared. Six different combinations were prepared and tested and their concentrations were listed in Table 1. In addition, 0.9% saline was used to generate aerosols for the purpose of comparing particle size.

Methods: Test Solution Preparation and Composition:
1. Preparation of Caspofungin Diacetate Stock Solution:
   500 mg of caspofungin diacetate was dissolved in 5.0 mL of 0.9% saline to obtain 5 mL of caspofungin diacetate stock solution. The concentration should have been close to 100 mg/mL (assuming the density of the stock solution was close to 1).
2. Preparation of PVP K30 Stock Solution:
   In a 25 mL volumetric flask 2.5 g of PVP K30 was dissolved in 20 mL 0.9% saline. Adjusted the pH to 6 with 1N NaOH solution. Normal saline was added to the mark and mix well. This provided 100 mg/mL PVP K30 stock solution.

The suitability of formulations was tested by aerosolizing it with the use of one PART Star nebulizer which was connected to compressed air at 28 psi. The air flow to the nebulizer was about 6.2 L/min. Approximately 7 mL of the test formulation solution was placed in the nebulizer, weighed and connected to air supply for aerosolization. The nebulizer was allowed to operate for 12 minutes and the nebulizer was disconnected from the air supply and post weighed. The generated aerosol was delivered into a plenum with a narrow opening. A stream of test aerosol was sampled from the plenum for particle size determination. A Quartz Crystal Microbalance (QCM) based cascade impactor was used for these determinations. This procedure was repeated for all six formulations plus saline.

Results: Aerosol generation was possible with all six solutions. The dispersion rate and particle size are summarized in Table 1. The aerosolization rate in mg/min decreased with increasing concentration of polyvinylpyrrolidone (PVP) in the formulation, possibly due to increase in viscosity of the formulation with increased polyvinylpyrrolidone (PVP). Solution #2 and 4 were noticed to foam during the aerosolization.

Particle size distribution, showed a tendency to be bimodal for most of the measurements. The saline (salt) used in the solution possibly contributed to the second mode. Since these data were fitted to a unimodal distribution for calculation of MMAD and GSD, it resulted in higher GSDs than normal (typically <3). MMAD showed an increasing trend with increased concentration of polyvinylpyrrolidone (PVP) in the formulation but all MMADs were within the respirable range.

Example 2: Caspofungin Formulations

General: HPLC analysis was carried out on a Waters 2695 separations module equipped with an autosampler and a Waters 996 photodiode array detector. The HPLC method is described below:
Column: Waters symmetry C18 3.5 µm, 4.6×75 mm
Flow rate: 1.0 mL/min
Detection: 220 nm
Column Temperature: 30° C.
Autosampler temperature: 4° C.
Injection volume: 50 µL
Run time: 70 min
Mobile phase: A: Add 1.0 mL of perchloric acid and 0.75 g of sodium chloride in 1000 mL HPLC grade water; B: Acetonitrile.
Gradient: As shown in Table 2

TABLE 2

| HPLC Gradient | | |
| --- | --- | --- |
| Time (min) | Mobile phase A (%) | Mobile phase B (%) |
| 0 | 67 | 33 |
| 14.5 | 67 | 33 |
| 35 | 50 | 50 |
| 45 | 25 | 75 |
| 50 | 20 | 80 |
| 52 | 20 | 80 |
| 53 | 67 | 33 |
| 70 | 67 | 33 |

Lyophilization was accomplished using a VirTis benchtop manifold lyophilizer under vacuum of <50 mTorr.

TABLE 1

Aerosolization Test Results
Formulation Configuration

| | Solution Number | | | | | | |
| --- | --- | --- | --- | --- | --- | --- | --- |
| | A1 | A2 | A3 | A4 | A5 | A6 | A7 |
| Caspofungin diacetate final concentration, mg/mL | 5 | 5 | 5 | 10 | 10 | 10 | 0.9% Saline |
| PVP concentration final concentration, mg/mL | 5 | 10 | 20 | 10 | 20 | 40 | |
| Caspofungin diacetate/PVP K30 ratio (w/w) | 1:1 | 1:2 | 1:4 | 1:1 | 1:2 | 1:4 | |
| Caspofungin diacetate Stock (100 mg/mL) in mL | 0.5 | 0.5 | 0.5 | 1 | 1 | 1 | |
| PVP K30 Stock (100 mg/mL) in mL | 0.5 | 1 | 2 | 1 | 2 | 4 | |
| 0.9% normal saline (approx volumes) in mL | 9 | 8.5 | 7.5 | 8 | 7 | 5 | |
| Total (fill to mark in 10 mL vol flask w saline) | 10 mL | 10 mL | 10 mL | 10 mL | 10 mL | 10 mL | |
| Aerosolization Data | | | | | | | |
| Aerosolization time, min (A) | 12 | 12 | 12 | 12 | 12 | 12 | 12 |
| Pre wt, g (nebulizer + formulation), B | 42.49 | 42.7 | 42.6 | 44.8 | 42.8 | 42.9 | 44.7 |
| Post wt, g (nebulizer + formulation), C | 40.32 | 40.8 | 40.8 | 43.0 | 41.0 | 41.3 | 42.6 |
| Dispersion rate, mg/min = (B − C)/A (Calculation carried out with unrounded data for pre and post weights) | 180.6 | 157.7 | 151.1 | 149.6 | 151.2 | 137.8 | 169.4 |
| Aerosol Particle Size Distribution[1] | | | | | | | |
| MMAD[2], microns | 0.94 | 0.90 | 0.94 | 0.89 | 1.09 | 1.10 | 0.52 |
| GSD[3] | 2.8-4.0 | 3.1-4.1 | 2.7-2.9 | 3.4-3.8 | 3.1-3.7 | 4.6-5.6 | 2.2-3.3 |

[1] Aerosol showed bimodal distribution; this resulted in high GSD values
[2] Mass Median Aerodynamic Diameter
[3] Geometric Standard Deviation Lyophilized Caspofungin Diacetate Formulation Screen in Acetate Buffer pH 4

Aliquots of 0.5 mL of each formulation listed in Table 3 were frozen on dry ice for 30 min and lyophilized for 40 h to obtain white cakes. A portion of each cake was reconstituted in 1 mL of deionized water and analyzed by HPLC. The vials were stoppered, crimp sealed and placed on stability at 5° C. and 40° C.

TABLE 3

Compositions of Caspofungin Diacetate Liquid Formulations before Lyophilization

|  | Form 1 | Form 2 | Form 3 |
|---|---|---|---|
| Caspofungin diacetate | 46.6 mg | 46.6 mg | 46.6 mg |
| Povidone | 80 mg | 40 mg | 20 mg |
| Acetate buffer pH 4 | 1 mL | 1 mL | 1 mL |
| Povidone/caspofungin diacetate ratio (w/w) | 1.72:1 | 0.86:1 | 0.43:1 |

Lyophilized Caspofungin Diacetate Formulation Screen

TABLE 4

Solid Compositions of Lyophilized Caspofungin Formulations 7-9

|  | Form 7 | Form 8 | Form 9 | Pure API |
|---|---|---|---|---|
| Caspofungin diaceate (free base) | 40 mg | 40 mg | 40 mg | 40 mg |
| Povidone K30 | 80 mg | 160 mg | 240 mg | — |
| Povidone K30/API (freebase) ratio | 2:1 | 4:1 | 6:1 | 0:1 |

TABLE 5

Compositions Before Lyophilization for Formulations 7-9

|  | Form 7 | Form 8 | Form 9 | Pure API |
|---|---|---|---|---|
| Caspofungin diacetate 200 mg/mL (freebase) stock pH 5.7 | 0.2 mL | 0.2 mL | 0.2 mL | 0.2 mL |
| Povidone K30 100 mg/ml stock pH 6.0 adjusted with 1N NaOH/HOAc | 0.8 mL | 1.6 mL | 2.4 mL | — |
| DI water | 2.0 mL | 1.2 mL | 0.4 mL | 2.8 mL |
| Total volume (mL) | 3.0 | 3.0 | 3.0 | 3.0 |

Each liquid formulation in Table 5 was equally split into two vials, frozen on dry ice for 1 h and lyophilized for 90 h to obtain white cakes. The vials were stoppered, crimp sealed and placed on stability at 5° C. and 40° C.

Preparation of Lyophilized Caspofungin Diacetate Formulations with PVP/API Ratio of 2:1 and 4:1

The liquid formulations to be lyophilized were prepared according to Table 6. Aliquots of 0.5 mL of each liquid formulation were placed in 3 mL glass vials, frozen on dry ice for 40 min. The vials were partially stoppered with lyo septa and lyophilized for 5 days. The vials were placed on stability at 5° C., ambient (dark) and −20° C.

TABLE 6

Liquid Formulations to be Lyophilized

|  | API | Form 13 | Form 14 |
|---|---|---|---|
| Caspofungin diaceate 160 mg/mL stock | 0.25 mL | 0.625 mL | 0.625 ml |
| Povidone K30 100 mg/mL stock pH 6.05 adjusted with 1N NaOH | — | 2.0 mL | 4.0 mL |
| Deionized water | 1.75 mL | 2.375 mL | 0.375 mL |
| Total volume | 2.0 mL | 5.0 mL | 5.0 mL |
| PVP K30/Caspofungin diacetate ratio (w/w) | 0 | 2:1 | 4:1 |

Caspofungin Acetate Lyo Formulation Preparation and Assay by HPLC

Preparation of 20 mg/mL Caspofungin Acetate Pre-Lyo Solution (Caspofungin Acetate/PVP=1:

4). Caspofungin acetate (100 mg, 97.6% assay) was dissolved in DI water (0.525 g) to obtain 0.625 g caspofungin acetate stock solution at a nominal concentration of 160 mg/mL (assuming density=1). PVP K30 (400 mg) was dissolved in PBS buffer (3.6 g), adjust pH to 6 with 25 µL of 1.0 N HCl to obtain 4.0 g of PVP stock solution with a nominal concentration of 100 mg/mL (assuming density=1). Caspofungin acetate stock solution of step 1 was combined with the PVP solution of step 2. An additional 0.375 g of PBS buffer was added to obtain 5.0 g of the pre-lyo solution with a nominal caspofungin acetate concentration of 20 mg/mL (assuming density=1). The theoretical wt % caspofungin acetate concentration is 100×(100×97.6%)/5000=1.952%

Preparation of Caspofungin Acetate Lyo Formulation Based on Weight of the Pre-Lyo Solution (0.5 g/Vial).

0.5 g of the pre-lyo solution was weighed into a lyo vial. The vial was frozen on dry ice for 1 hr and lyophilized for 5 days as described above.

Preparation of Caspofungin Acetate Lyo Formulation Based on Volume of the Pre-Lyo Solution (0.5 mL/Vial).

0.5 mL of the pre-lyo solution was pipetted into a lyo vial. The vial was frozen on dry ice for 1 hr and lyophilized for 5 days as described above.

HPLC Assay.

HPLC analysis was carried out on a Waters 2695 separations module equipped with an autosampler and a Waters 996 photodiode array detector. The HPLC method is described below:

Column: Waters Symmetry C18 Column, 3.5 µm, 4.6 mm×100 mm

UV detection: 220 nm

Column temperature: 30° C.

Flow rate: 1.0 mL

Injection volume: 50 µL

Sample tray temperature: 4° C.

Run time: 70 min

Mobile phase:

Mobile phase A: Add 1.0 mL of perchloric acid and 0.75 g of sodium chloride, q.s. with water to 1000 mL.

Mobile phase B: Acetonitrile

Gradient program: As shown in Table 7.

TABLE 7

HPLC Gradient

| Time (min) | Mobile phase A (%) | Mobile phase B (%) |
|---|---|---|
| 0 | 67 | 33 |
| 14.5 | 67 | 33 |
| 35 | 50 | 50 |
| 45 | 25 | 75 |
| 50 | 20 | 80 |
| 52 | 20 | 80 |
| 53 | 67 | 33 |
| 70 | 67 | 33 |

Preparation of Caspofungin Acetate Standard Solution.

Corrected assay: (100−2.7)×99.3%=96.6%. In a 25.00 mL volumetric flask was placed 13.78 mg of the caspofungin acetate working standard. DI water was added to dissolve and q.s. to mark.

Preparation of HPLC Sample of Pre-Lyo Solution.

23.17 mg of the pre-lyo solution was weighed into an HPLC vial. DI water was added to give a total weight of 1.000 g (1.000 mL) of solution.

Assay Calculation for Pre-Lyo Solution.

Calculation of Caspofungin acetate concentration in HPLC sample:

Caspo conc.=(Area$_{sample}$/Area$_{std}$)×corr. Assay$_{std}$×
$W_{std}/W_{std}$=(14974300/18005050)×96.6%×13.78/
25=0.44 mg/mL Caspofungin acetate concentration (wt %) in pre-lyo solution:

Caspofungin acetate concentration (wt %)=(Caspofungin acetate conc. of HPLC sample×volume of HPLC sample)/Weight of Pre-lyo solution)×
100=(0.44×1.0/23.17)×100=1.90%

% Lyo solution concentration=100×(1.90%/1.978%)=
96.1%

Reconstituted Caspofungin Acetate Lyo Vial for HPLC Analysis.

Caspofungin acetate lyo cake (50 mg) was reconstituted by adding 1.0 mL of DI water via a pipette to obtain stock solution. The solution was vortexed for 20-30 seconds and visually checked to ensure complete dissolution. 55 μL of the stock solution was pipetted and added into a HPLC vial containing 1.0 ml of DI water. The solution was vortexed for a few seconds to mix.

Preparation of Caspofungin Acetate Standard Solution.

Corrected assay: (100−2.7)×99.3%=96.6%. In a 25.00 mL volumetric flask was placed 13.95 mg of the caspofungin acetate standard. DI water was added to dissolve and q.s. to mark.

Assay Calculation for Lyo Cake.

Lyo cake based on 0.5 g of the pre-lyo solution:

Theoretical amount of caspofungin acetate (mg)/
vial=0.5×1000×1.90%=9.5 mg

Step 1: Calculation of Caspofungin acetate concentration in HPLC sample

HPLC sample Caspofungin acetate conc.=(Area$_{sample}$/Area$_{std}$)×corr. Assay$_{std}$×$W_{std}/W_{std}$=
(15655992/17947658)×96.6%×13.95/25=0.47
mg/mL Calculation of caspofungin acetate in lyo vial:

Weight of caspofungin acetate in lyo vial=(HPLC sample Caspofungin acetate conc. of step 1×Volume of HPLC sample/Volume of reconstituted solution used to make HPLC sample×total volume of reconstituted solution=(HPLC sample Caspofungin acetate conc. of step 1×1.055/0.055)×1.050=(0.47×1.055/0.055)×1.050=9.47 mg Calculation of caspofungin acetate assay:

Assay=100×(weight by HPLC/label claim)=100×
(9.47/9.5)=99.7%

Table 8 shows details of a caspofungin acetate lyo solution prepared as described herein.

TABLE 8

Caspofungin acetate lyo solution

| | Amount of lyo solution | Theoretical | Results based on HPLC assay | % Theoretical |
|---|---|---|---|---|
| Caspofungin acetate Lyo solution 20 mg/mL | N/A | 19.56 mg/mL (adjusted for assay) | 19.0 mg/mL | 97.1 |

Preparation of Lyophilized Caspofungin Diacetate Formulations (Caspofungin Diacetate/PVP K30=1:4) in Deionized Water, 0.9% Saline and PBS Buffer A. Preparation of Caspofungin Diacetate Stock Solution Caspofungin diacetate (0.8 g) was dissolved in deionized water (4.2 g) to obtain 5.0 g of a clear solution with caspofungin diacetate concentration of 160 mg/ml (assuming density=1 mg/mL).

B. Preparation of PVP K30 Stock Solution in Deionized Water, 0.9% Saline and PBS Buffer PVP K30 (0.8 g) was dissolved in a diluent (7.2 g) as shown in Table 9 to obtain a clear solution. The pH of the resultant solution was adjusted to about 6 with 1N NaOH solution.

TABLE 9 pH of PVP K30 Stock Solutions in DI water, 0.9% Saline and PBS buffer.

| Diluent | pH |
|---|---|
| Deionized water | 6.03 |
| 0.9% saline | 6.2 |
| PBS buffer | 5.95 |

C. Preparation of Liquid Formulations for Lyophilization

Caspofungin diacetate/PVP K30 formulations: The caspofungin diacetate stock solution of Part A (1.25 mL), the PVP K30 stock solution (8.0 g) and the corresponding diluent in the PVP K30 solution (0.75 mL) of Part B was combined to obtain 10 mL of the liquid formulations ready for lyophilization. The ratio of caspofungin diacetate/PVP K30 is 1:4 (w/w).

Caspofungin diacetate only (control): Caspofungin diacetate (0.2 g) was dissolved in deionized water (9.8 mL) to obtain a clear solution with caspofungin diacetate concentration of 20 mg/mL.

D. Lyophilization

Fourteen 0.5 mL aliquots of each liquid formulation prepared in part C were placed in 14 3-mL glass vials. The vials were frozen on dry ice for about 1 h and lyophilized for 5 days to obtain white cake. The vials were stoppered, crimp sealed and placed on stability at −20° C., 5° C., and ambient (dark) conditions.

TABLE 10

Lyophilized Caspofungin Diacetate Formulations Prepared from Water, Saline and PBS.

| | Form 15 | Form 16 | Form 17 |
|---|---|---|---|
| Caspofungin diacetate (mg) | 10 | 10 | 10 |
| Povidone K30 (mL) | 40 | 40 | 40 |
| Total Volume (mL) | 0.5 | 0.5 | 0.5 |
| Acetate buffer pH | 6.13 | 6.01 | 6.14 |
| PVP K30/Caspofungin diacetate ratio (w/w) | 4:1 | 4:1 | 4:1 |

E. HPLC Analysis

One vial of the lyophilized cake was reconstituted in 1 mL of deionized water to obtain a 10 mg/mL caspofungin diacetate solution. An aliquot (55 µL) was removed and diluted with 1 mL of deionized water for HPLC analysis.

Results

Figure 1B:
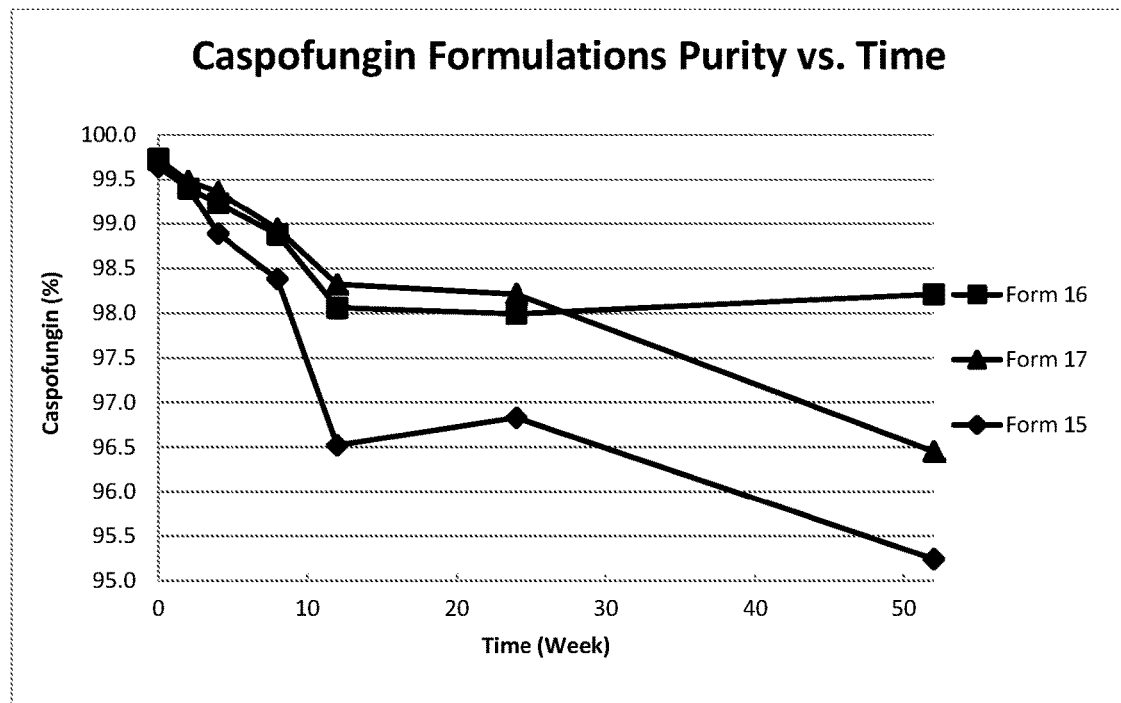
FIG. 1B shows the total caspofungin (%) following storage at 25° C. as determined by HPLC for formulations 15, 16, and 17.

Tables 11, 12, 13, and 14 summarize the total caspofungin (%) as determined by HPLC present for each formulation prepared prior to storage and after several storage conditions. RT as below refers to HPLC retention time. The product with a retention time of 26.1 minutes is a hydrolysis degradation product while the product with a retention time of 37.3 minutes is a dimerization degradation product that is obtained from the dimerization of the hydrolysis products. FIG. 1A shows the total caspofungin (%) following storage at 5° C. as determined by HPLC for formulations 15, 16, and 17. FIG. 1B shows the total caspofungin (%) following storage at 25° C. as determined by HPLC for formulations 15, 16, and 17.

TABLE 11

Total Caspofungin (%) in Formulations 1-3 Under Storage Conditions by HPLC Assay

| | Pure API (control, 99.72%) | Form 1 | Form 2 | Form 3 |
|---|---|---|---|---|
| HPLC purity % 5° C. 1 week | — | 99.11 | 98.13 | 98.4 |
| RT 26.1 | — | 1.19 | 1.38 | 1.22 |
| RT 37.3 | — | 0.14 | 0.23 | 0.22 |
| HPLC purity % 5° C. 3 week | — | 98.7 | — | — |
| RT 26.1 | — | 1.04 | — | — |
| RT 37.3 | — | 0.14 | — | — |
| HPLC purity % 40° C. 1 week | 88.48 | 91.86 | 89.5 | 87.32 |
| RT 26.1 | — | 1.07 | 1.88 | 2.1 |
| RT 37.3 | — | 2.45 | 3.06 | 3.35 |
| HPLC purity % 40° C. 3 week | 75.71 | 88.12 | — | — |
| RT 26.1 | 6.09 | 1.22 | — | — |
| RT 37.3 | 4.38 | 2.8 | — | — |
| HPLC purity % 40° C. 6 week | — | 79.41 | — | — |
| RT 26.1 | — | 5.53 | — | — |
| RT 37.3 | — | 3.31 | — | — |

TABLE 12

Total Caspofungin (%) in Formulations 7-9 Under Storage Conditions by HPLC Assay

| | API (lyo process) | Form 7 | Form 8 | Form 9 |
|---|---|---|---|---|
| HPLC purity % T0 | 95.82 | 98.73 | 99.3 | 99.38 |
| RT 26.1 | 2.17 | 0.73 | 0.42 | 0.49 |
| RT 37.3 | 1.57 | 0.19 | 0.08 | 0.04 |
| HPLC purity % 40° C. 1 week | 82.32 | 91.69 | 93.87 | 94.97 |

TABLE 12-continued

Total Caspofungin (%) in Formulations 7-9 Under Storage Conditions by HPLC Assay

| | API (lyo process) | Form 7 | Form 8 | Form 9 |
|---|---|---|---|---|
| RT 26.1 | 2.88 | 1.33 | 1.66 | 1.25 |
| RT 37.3 | 9.26 | 4.87 | 3.25 | 2.78 |

TABLE 13

Total Caspofungin (%) in of Formulations 13 and 14 Under Storage Conditions by HPLC Assay

| | Form 13 | Form 14 |
|---|---|---|
| HPLC purity % @T0 | 98.97 | 99.14 |
| HPLC purity % 5° C. 8 week | 98.46 | 99.03 |
| HPLC purity % 25° C. 8 week | 96.63 | 97.73 |

TABLE 14

Total Caspofungin (%) in Formulations 15, 16, and 17 Under Storage Conditions by HPLC Assay

| | API (lyo process) | Form 15 | Form 16 | Form 17 |
|---|---|---|---|---|
| HPLC purity % T0 | 95.42 | 99.64 | 99.73 | 99.72 |
| HPLC purity % −20° C. 2 week | — | 99.68 | 99.73 | 99.67 |
| HPLC purity % −20° C. 1 month | — | 99.64 | 99.63 | 99.69 |
| HPLC purity % −20° C. 6 month | — | 99.63 | 99.75 | 99.66 |
| HPLC purity % −20° C. 12 month | — | 99.41 | 99.59 | 99.64 |
| HPLC purity % 5° C. 2 week | — | 99.57 | 99.64 | 99.62 |
| HPLC purity % 5° C. 1 month | — | 99.59 | 99.55 | 99.61 |
| HPLC purity % 5° C. 2 month | — | 99.46 | 99.59 | 99.58 |
| HPLC purity % 5° C. 3 month | — | 99.17 | 99.50 | 99.63 |
| HPLC purity % 5° C. 6 month | — | 99.41 | 99.54 | 99.52 |
| HPLC purity % 5° C. 12 month | — | 99.14 | 99.14 | 99.39 |
| HPLC purity % 25° C. 2 week | — | 99.40 | 99.40 | 99.48 |
| HPLC purity % 25° C. 1 month | — | 98.89 | 99.23 | 99.36 |
| HPLC purity % 25° C. 2 month | — | 98.38 | 98.88 | 98.94 |
| HPLC purity % 25° C. 3 month | — | 96.52 | 98.06 | 98.32 |
| HPLC purity % 25° C. 6 month | — | 96.83 | 97.99 | 98.21 |
| HPLC purity % 25° C. 12 month | — | 95.24 | 97.14 | 96.45 |

The effect of salt vs. increased PVP ratio affects water content and contributes to HPLC purity at different storage solutions, as shown in Tables 15 and 16.

TABLE 15

Lyophilized Caspofungin Diacetate Formulations Prepared with PBS buffer with different PVP K30 ratio.

| | Form 18 | Form 19 | Form 20 |
|---|---|---|---|
| Caspofungin diacetate (mg) | 10 | 10 | 10 |
| Povidone K30 (mg) | 10 | 20 | 30 |
| Total Volume of PBS buffer (mL) | 0.5 | 0.5 | 0.5 |
| PVP K30/Caspofungin diacetate ratio (w/w) | 1:1 | 2:1 | 3:1 |
| KF water content % | 5.33 | 2.44 | 2.05 |

TABLE 16

Total Caspofungin (%) in Formulations 18-20
Under Storage Conditions by HPLC purity.

|  | Form 18 | Form 19 | Form 20 |
|---|---|---|---|
| HPLC purity % T0 | 99.27 | 99.34 | 99.40 |
| HPLC purity % −20° C. 3 month | 98.88 | 99.15 | 99.29 |
| HPLC purity % 5° C. 43 days | 98.42 | 98.89 | 99.21 |
| HPLC purity % 5° C. 3 month | 97.75 | 98.13 | 98.94 |
| HPLC purity % 25° C. 43 days | 91.87 | 98.04 | 98.40 |
| HPLC purity % 25° C. 3 month | 87.35 | 96.67 | 97.46 |

Tables 17 and 18 summarize the % water content measured of the prepared formulations.

TABLE 17

Water Content of Formulations 1, 7, 8, 13 and 14

|  | Form 1 | Form 7 | Form 8 | API (lyo process) | Form 13 | Form 14 |
|---|---|---|---|---|---|---|
| KF water content % T0 | 6.52 | 10.29 | 9.38 | 3.94 | 2.83 | 1.60 |

|  | API (lyo process) | Form 15 | Form 16 | Form 17 | Form 18 | Form 19 | Form 20 |
|---|---|---|---|---|---|---|---|
| KF water content % T0 (Average of duplicates) | 6.16 | 0.92 | 0.87 | 0.79 | 5.33 | 2.44 | 2.05 |

TABLE 18

Water Content of Formulations 15-20.

|  | API (lyo process) | Form 15 | Form 16 | Form 17 | Form 18 | Form 19 | Form 20 |
|---|---|---|---|---|---|---|---|
| KF water content % T0 (Average of duplicates) | 6.16 | 0.92 | 0.87 | 0.79 | 5.33 | 2.44 | 2.05 |

Example 3. In Vitro Antifungal Activity with Formulations 16 and 17

The antifungal potency of the test article(s) was measured using the in vitro broth microdilution assay under assay conditions described by the Clinical and Laboratory Standards Institute. In this assay, the Minimum Inhibitory Concentration (MIC) is defined as the lowest concentration of an agent that causes a specified reduction in visible growth of the microorganism. The Minimal Effective Concentration (MEC) is defined as the lowest concentration of an agent that leads to the growth of small, rounded, compact hyphal forms as compared to the hyphal growth seen in the growth control well. In this study, MIC values are determined for the 9 *Candida* species and *Cryptococcus neoformans*. MEC values are determined for 3 filamentous fungi (2 *Aspergillus fumigatus* and *Trichophyton rubrum*). Test articles were prepared as the following:

CANCIDAS®:

The 5 mg/mL stock solution was prepared as the following.
(1) The refrigerated vial was equilibrated to room temperature.
(2) Test vial was reconstituted aseptically with 10.5 mL 0.9% NaCl.
(3) The white to off-white powder was dissolved completely, mixing gently until a clear solution was obtained.
(4) The final concentration was 5.0 mg/mL of Caspofungin freebase. The reconstituted solution was stable for 1 hr at room temperature.
(5) The 5 mg/mL stock solution was then diluted in 0.9% NaCl to prepare the 3.2 mg/mL working stock solution for MIC testing.

Formulations 16 and 17:

The 5 mg/mL stock solution was prepared as the following.
(1) The refrigerated vial was equilibrated to room temperature.
(2) Test vial was reconstituted aseptically with 1.8 mL 0.9% NaCl.
(3) The white to off-white powder was dissolved completely, mixing gently until a clear solution was obtained.
(4) The final concentration was 5.0 mg/mL of Caspofungin freebase. The reconstituted solution was used within 1 hr at room temperature.
(5) The 5 mg/mL stock solution was then diluted with 0.9% NaCl to prepare the 3.2 mg/mL working stock solution for MIC testing.

Caspofungin Diacetate:

The 5 mg/mL stock solution was prepared as the following.
(1) The refrigerated vial was equilibrated to room temperature.
(2) Test vial was filled aseptically with 1.8 mL 0.9% NaCl.
(3) The white to off-white powder was dissolved completely, mixing gently until a clear solution was obtained.
(4) The final concentration was 5.0 mg/mL of Caspofungin freebase. The reconstituted solution was used within 1 hr at room temperature.
(5) The 5 mg/mL stock solution was then diluted with 0.9% NaCl to prepare the 3.2 mg/mL working stock solution for MIC testing.

Amphotericin B:

2.88 mg compound, corresponding to 1.2 mg active compound with a correction factor of 2.40 was added 0.375 mL of water for injection to generate the 3.2 mg/mL working stock solution for MIC testing.

The 3.2 mg/mL working stock solution was 2-fold diluted serially in 0.9% NaCl to prepare a total of eleven 50-fold stock solutions, concentrations ranging from 3.2 to 0.003 mg/mL. A 4 µL aliquot of each dilution was added to 196 µL of broth medium seeded with the organism suspension in wells of a 96 well plate (fungal cell count: $1 \times 10^3$ to $1 \times 10^4$ colony forming units per mL). The final volume was 200 µL in each well. Following incubation, the test plates were visually examined and wells were scored for growth or complete growth inhibition to define the MIC values. Microscopy examination was used to determine the MEC values. Each test substance was evaluated in duplicate and the results below are the duplicate test values. Vehicle-control and an active reference agent were used as blank and positive controls, respectively. The Formulations 16 and 17 retained its anti-fungal activity against the tested *Candida, Cryptococcus, Aspergillus* and *Trichophyton* strains (Table 19 and 20). The Formulations 16 and 17 have similar antifungal activity compared to CANCIDAS® and Caspofungin diacetate against *Candida, Cryptococcus, Aspergillus* and *Trichophyton* strains (Table 19 and 20)

Example 4: Pharmacokinetic Studies with Caspofungin Formulations

Experimental Design: Caspofungin was administered to rats at a target dose of 2 mg/kg by nose only inhalation (by deposition) or intravenously (IV) to determine the plasma and tissue concentrations and pharmacokinetics.

Whole blood samples were collected from three animals per time-point at approximately 0.5, 1, 2, 4, 8, 12, 24 and 48 hours and 7 days after dose administration for plasma drug level determination. Rats were anesthetized with 70% CO2/30% air and blood was collected from the retro-orbital plexus and placed into tubes containing anticoagulant (EDTA). Blood samples were placed on ice immediately following collection and processed (i.e., centrifuged) to plasma. The samples were then stored frozen (at approximately −70° C.) until analyzed.

Tissue specimens (lung, liver and kidney) were collected from three animals per time point at 0.5, 2, 24 and 48 hours and 7 days after dose administration. All tissue specimens were stored frozen at approximately −70° C. until analyzed.

Plasma and tissue samples were analyzed for levels of caspofungin using high performance liquid chromatography-mass spectrometry-mass spectrometry (LC-MS-MS) according to methods established for the study.

TABLE 19

Minimum Inhibitory Concentrations of various formulations against selected Fungus.

| No. | Species | Strain ID | CANCIDAS® | Form 16 | Form 17 | Caspofungin diacetae | amphotericin B |
|---|---|---|---|---|---|---|---|
| | | | MIC, µg/ml | | | | |
| 1 | *Candida albicans* | ATCC44858 | 0.5 | 0.25 | 0.25 | 0.25 | 0.125 |
| 2 | *Candida albicans* | ATCC90028 | 0.25 | 0.25 | 0.25 | 0.25 | 0.125 |
| 3 | *Candida albicans* | ATCC90028 + 50% human serum | 0.125 | 0.25 | 0.25 | 0.125 | 0.25 |
| 4 | *Candida albicans* | Azole-R (20183.073) | 0.25 | 0.25 | 0.25 | 0.25 | 0.125 |
| 5 | *Candida albicans* | Azole-R (20186.025) | 0.5 | 0.5 | 0.25 | 0.25 | 0.25 |
| 6 | *Candida glabrata* | ATCC 36583 | 0.25 | 0.5 | 0.25 | 0.25 | 0.125 |
| 7 | *Candida krusei* | ATCC 6258 | 1 | 1 | 1 | 1 | 0.25 |
| 8 | *Candida parapsilosis* | ATCC 22019 | 1 | 2 | 1 | 1 | 0.25 |
| 9 | *Candida tropicalis* | ATCC 200956 | 0.5 | 0.5 | 0.25 | 0.25 | 1 |
| 10 | *Cryptococcus neoformans* | ATCC 24067 | 16 | 16 | 16 | 16 | 0.125 |

TABLE 20

Minimum Effective Concentrations of various formulations against selective Fungus.

| No. | Species | Strain ID | CANCIDAS® | Form 16 | Form 17 | Caspofungin diacetae | MIC, µg/ml amphotericin B |
|---|---|---|---|---|---|---|---|
| | | | MEC, µg/ml | | | | |
| 1 | *Aspergillus fumigatus* | ATCC 13073 | 0.125 | 0.125 | 0.125 | 0.0625 | 0.25 |
| 2 | *Aspergillus fumigatus* | ATCC204305 | 0.125 | 0.25 | 0.125 | 0.125 | 0.5 |
| 3 | *Trichophyton rubrum* | ATCC 10218 | 0.25 | 0.25 | 0.25 | 0.125 | 0.125 |

Exposure of male rats to caspofungin via nose-only inhalation or via intravenous injection resulted in no test-article related mortality; no clinical signs of toxicity; no effects on body weight; and no gross necropsy findings attributable to exposure to the test article.

In Vivo Details: Thirty Sprague-Dawley derived rats [Crl:CD®(CD)Br] were obtained from Charles River Laboratories, Inc., Wilmington, Mass., for use in this study. The rats were 52 days of age (approximately 7.5 weeks) upon arrival. One day following receipt, body weights of the rats ranged from 171 g to 213 g. The animals were held in quarantine for 7 days prior to administration of the test article. Throughout the quarantine period, animals were observed at least once daily for mortality or evidence of a moribund state. Before being released from quarantine, the animals were given a detailed, hand-held physical examination to ensure their health and suitability as test subjects. The test animals were approximately 8.5 weeks old at the start of the first exposure to the test article.

During non-exposure periods of the study all animals were housed in Lab Products Inc., polycarbonate "shoe-box" cages (10.5"×19"×8"), with absorbent hardwood chip bedding. The animals were double housed for the quarantine period), in cages equipped with automatic water and food containers. Animals were double housed for the treatment period in cages equipped with automatic water and food containers. Following group assignment, racks and cages were cleaned and sanitized.

Animal room environmental conditions were recorded at least once daily throughout the quarantine and exposure periods. Temperatures ranged from 20° C. to 21° C. throughout the study, and relative humidity (% RH) values ranged from 46 to 56%. Fluorescent lighting in the animal room was provided on a cycle of 12 hours of light followed by 12 hours of darkness (light from approximately 6:00 a.m. to 6:00 μm).

To condition the animals to placement and restraint in the nose-only exposure system and reduce stress during the exposure phase, the animals were acclimated to the holding tubes by placing each rat in a nose-only holding tube for approximately 45 minutes one working day prior to exposure.

The study complied with all applicable sections of the Animal Welfare Act (AWA; Title 9, Code of Federal Regulations), the Public Health Service Policy on Humane Care and Use of Laboratory Animals (National Institutes of Health's Office of Laboratory Animal Welfare, 2002), and the Guide for the Care and Use of Laboratory Animals (National Research Council, 2011). To the extent possible, procedures used in this study were designed to avoid or minimize discomfort, stress, and pain to animals.

The animals were fed Harlan's Certified Global 18% Protein Rodent (2018C). Each certified lot of diet was analyzed for contaminants to ensure that none are present at concentrations that would be expected to interfere with the conduct or purpose of this study. Analytical data from the lots of diet to be used in the study are retained on file. Coarse-filtered City of Chicago water was provided ad libitum to all rats via automatic watering system. Supply water is analyzed periodically for bacterial contamination and chemical composition (e.g., electrolytes, metals, etc.).

Test Article Preparation for Solution 1 (Inh1)

One day prior to the study day, caspofungin diacetate was transferred from the −70° C. freezer to −20° C. freezer overnight. On the study day, caspofungin diacetate was transferred from −20° C. freezer to 4° C. refrigerator for 2 hrs. Prior to opening the vial, the vial was stored in a room temperature desiccator for 1 hour to allow the contents to come to room temperature.

For inhalation exposure, a 10 mg/mL dosing solution was prepared by dissolving 800 mg of caspofungin diacetate powder in 80 mL of 0.9% saline solution. The resulting solution was aseptically filtered and kept refrigerated between 2-8° C. until used. The formulation was aerosolized for inhalation administration.

Test Article Preparation for Inhalation Solution 2 (Inh2)

1. Preparation of Caspofungin Diacetate Stock Solution 800 mg of caspofungin diacetate, which was warmed from storage as previously described, was dissolved in 8.0 mL of 0.9% saline to obtain 8 mL of caspofungin diacetate stock solution. The concentration should have been close to 100 mg/mL (assuming the density of the stock solution was close to 1).

2. Preparation of PVP K30 Stock Solution

In a 50 mL volumetric flask, 5.0 g of PVP K30 was dissolved in 45 mL of 0.9% saline. The pH was adjusted to 6 with 1N NaOH solution dropwise. Normal saline was added to the mark, approx 5 mL, and was mixed well to give a total volume of 50 mL. This provided 100 mg/mL PVP K30 stock solution.

3. Preparation of Test Article: Caspofungin Diacetate (10 mg/mL), PVP K30 (40 mg/ML)

In a 100 mL flask or glass bottle, 8.0 mL of caspofungin diacetate stock solution and 32 mL of PVP stock solution were added. 40 mL of normal saline was added in the flask and gently well mixed. The solution was sterile filtered through a 0.2-micron filter using a slight vacuum into a sterile 100 mL flask or bottle. The flask was stoppered. The test article was stored at 4° C. until use.

TABLE 21

| | |
|---|---|
| Caspofungin diacetate final concentration | 10 mg/mL |
| PVP concentration final concentration | 40 mg/mL |
| Caspofungin diacetate/PVP K30 ratio (w/w) | 1:4 |
| Caspofungin diacetate Stock (100 mg/mL) | 8 mL |
| PVP K30 Stock (100 mg/mL) | 32 mL |
| 0.9% normal saline (approx volumes) | 40 mL |
| Total | 80 mL |

Solution for IV administration (IV): A 2 mg/mL dosing solution from commercially obtained Cancidas (containing 54.6 mg of caspofungin diacetate) was prepared by a) adding into 10.8 mL of 0.9% saline into the Cancidas vial and swirling gently until the powder dissolved. 10.0 mL of this solution was extracted and added a 25 mL volumetric flask which was diluted to the mark with 0.9% saline and mixed well. The resulting solution was aseptically filtered and kept refrigerated between 2-8° C. until used.

Test Article Dosing: The animals were randomized into two groups of 15 animals based on body weight. Each group was dosed as shown in Table 22 below.

TABLE 22

| Exposure Group | Target Dose | Route | Duration (minutes) | Number of Animals |
|---|---|---|---|---|
| I | 2 mg/kg | Inhalation (Inh1) | 125 | 15 |
| II | 2 mg/kg | Inhalation (Inh2) | 140 | 15 |
| III | 2 mg/kg | IV | — | 15 |

The dose targeted for deposition via inhalation was 2 mg/kg and was calculated based on this equation:

Deposited dose=($C$×RMV×$T$×DF)/BW where C is the average caspofungin concentration in the exposure atmosphere during the exposure period, RMV is the respiratory minute volume, T is the exposure time, DF is the deposition fraction (assumed to be 10% per FDA guidelines) and BW is the average animal body weight on exposure day.

The dose for IV administration was calculated based on the body weight of each animal Delivered dose=$W$×2 mg/kg where W is animal weight (kg).
Inhalation Exposure Methods:

Inhalation Exposure Laboratory: The inhalation exposure part of the study was conducted in an inhalation facility. The supply air to the laboratories was preconditioned and automatically controlled with a thermostat and humidistat. Each flow-past nose-only inhalation exposure chamber (Lab Products Inc., Seaford, Del.) is comprised of 52 ports. The chambers were encased in an acrylic enclosure to isolate the exposure chamber and protect laboratory personnel. The test atmosphere inlet and exhaust configurations provided a uniform and continuous stream of fresh test atmosphere to the animals undergoing exposure. After flowing out of the supply port, any excess test atmosphere, along with exhaled air, is drawn into the chamber exhaust manifold without entering other ports.

During the inhalation exposure, the animals were restrained in nose-only holding tubes (CH Technologies, USA, Westwood, N.J.). Following confirmation of the correct animal number, each tube was placed in a pre-designated port of the inhalation exposure chamber. Chamber ports were rotated for each exposure; placement for each exposure is documented in the study records. Animal tube loading and unloading and tube insertion and removal from the chamber manifold processes were performed according to laboratory standard operating procedures that are designed to minimize stress to the rats. The rats were observed frequently while restrained to ensure that they remained in the tubes and were not in danger of injury. At the end of each exposure, when the chamber was purged of the test substance (less than one minute), the tubes with the animals were removed. The rats were removed from the tubes and returned to their home cages. The holding tubes were sanitized after each use.

Test Atmosphere Generation: Test atmosphere at the desired concentrations was generated by aerosolizing the test substance and mixing it with compressed filtered air to produce a continuous supply of test atmosphere. Test atmospheres were generated by aerosolizing the test formulation with a commercially available nebulizer using compressed air of breathable quality and which is filtered with a compressed air filter and a carbon adsorber.

Exhaust from the exposure chambers was moved through a high efficiency particulate air (HEPA) filter by a ring compressor and exhausted outside the building. Inlet and exhaust flows to and from the chamber were controlled and continuously monitored by rotometers.
Test Atmosphere Monitoring:

Gravimetric Analysis: The test atmosphere concentration in the exposure chamber was determined gravimetrically each exposure by collecting test atmosphere samples on filters placed in closed-face filter holders in the breathing zone of the animals. The gravimetric sampling train consisted of a pre-weighed filter in series with a dry-gas meter connected to a constant flow vacuum pump. Samples were collected at a constant flow rate equal to the port flow of the delivery tube. The filter samples were weighed to determine the aerosol mass collected. The dry-gas meter measured the corresponding volume of chamber air sampled and the weight-to-volume ratio was determined to obtain the aerosol mass concentration.

Aerosol Particle Size Distribution: Aerosol particle size distribution was determined once with a quartz crystal microbalance (QCM) cascade impactor (California Measurements Inc., Sierra Madre, Calif.) equipped with 10 stages to collect size-segregated samples. The mass median aerodynamic diameter (MMAD) and geometric standard deviation (GSD) were calculated from the mass accumulated on each collection stage of the QCM.

Temperature, Relative Humidity and Airflow Rate: Inhalation exposure chamber temperature, relative humidity and airflow rate (liters per minute; LPM) were measured and recorded once during the exposure. The chamber temperature and relative humidity were monitored with a hand-held thermohygrometer (35612 series, Oakton Instruments, Vernon Hills, Ill.).
Intravenous Administration:

Animals in the IV dosing group received a single injection via the tail vein at a dosing volume of 1 mL/kg.
Toxicology Methods:

Moribundity/Mortality Observations and Physical Examinations/Clinical Observations: Prior to initiation of dosing (exposure), animals were observed at least once daily for mortality or evidence of moribundity. A detailed, hand-held physical examination was conducted on all animals once during the quarantine period (prior to randomization). During the treatment period, the animals were observed daily for mortality or evidence of moribundity; these checks were separated by a minimum of four hours. Daily cage-side clinical observations were conducted during exposure, and daily hand-held clinical observations were conducted before and after exposure. Observations included, but were not limited to the following: changes in the skin and fur, eyes, and mucous membranes; effects on the respiratory, circulatory, autonomic and central nervous systems; and effects on somatomotor activity and behavior pattern.

Body Weights and Body Weight Changes: Body weights were determined one day after animal receipt; at randomization; and prior to exposure on Study Day 1, 2, 3 and 7 (as applicable based on scheduled euthanization).

Plasma and Tissue Samples/Necropsy: Whole blood samples were collected from three animals per time-point at approximately 0.5, 1, 2, 4, 8, 12, 24 and 48 hours and 7 days after dose administration for plasma drug level determination. Rats were anesthetized with 70% CO2/30% air and blood was collected from the retro-orbital plexus and placed into tubes containing anticoagulant (EDTA). Blood samples were placed on ice immediately following collection and processed (i.e., centrifuged) to plasma. The samples were then stored frozen (at approximately −70° C.) until analyzed. All study animals surviving to scheduled necropsy were euthanized by an overdose of an intraperitoneal injection of sodium pentobarbital at 35-45 mg/kg. Tissue specimens (lung, liver and kidney) were collected from three animals per time point at 0.5, 2, 24 and 48 hours and 7 days after dose administration. All tissue specimens were stored frozen at approximately −70° C. until analyzed.
Bioanalytical Method and Analysis:

Calibration and Internal Standards: The reference standard, caspofungin acetate (lot number 02220902; Chunghwa Chemical Synthesis & Biotech, Taiwan), was stored at approximately −70° C.; and used without further purification for the preparation of calibration standards and quality control (QC) samples for the determination of caspofungin in plasma and tissue samples collected from this study. The internal standard (caspofungin acetate-d4; lot number 10-GJF-162-1) was stored at −20° C.

Sample Preparation: For the determination of caspofungin in plasma, a 100 μL aliquot from each sample (in a 2 mL centrifuge tube) was mixed with 0.3 mL of acetonitrile (ACN; Spectrum, New Brunswick, N.J.) containing 150 ng of internal standard. After shaking for five minutes, the sample was centrifuged at 4° C. for 10 minutes to remove precipitated proteins and supernatant was transferred to an autosampler tube, diluted with 0.5 mL of water, and vortex-mixed for instrumental analysis.

For the determination of caspofungin in tissue, samples (lung—entire organ; liver—1 gram; kidneys—one organ) were finely cut and extracted for analysis by adding 2.5 mL of ASTM Type I water and shaking for approximately 0.5 hour, after which 2.5 mL of acetonitrile (ACN; Spectrum, New Brunswick, N.J.) were added following by shaking for another 0.5 hour. Subsequently, 100 μL of the supernatant was transferred to a 2 mL centrifuge tube and processed for analysis using the same procedure as for plasma.

Freshly prepared caspofungin standard curves and quality control (QC) samples were analyzed along with the study samples. Instrument calibrators and QC samples were prepared by adding 10 μL of a stock caspofungin solution in ACN/water (v/v 50/50) to 100 μL of blank rat plasma (for both plasma and tissue samples). Calibrator concentrations for plasma specimen analysis were approximately 0.050, 0.10, 0.20, 0.50, 1.0, 2.5, 5.0 and 10 μg/mL; QC samples were prepared at approximately 0.12, 4.0 and 8.0 μg/mL. Calibrator concentrations for tissue specimen analysis were approximately 1, 2, 5, 10, 20, 50 and 100 ng/sample; QC samples were prepared at approximately 2.4, 40 and 80 ng/sample. Calibrators and QC samples were processed for analysis following the procedure described above.

Analytical Equipment and Conditions: Calibrator, QC and study samples were analyzed under LC-MS-MS instrument conditions as detailed in Table 23.
The retention time of caspofungin was approximately 2.3 minutes. Calibration curves were calculated from the linear regression (weighting factor of $1/x^2$) of the caspofungin peak area to internal standard peak area ratios versus caspofungin concentration. Concentration of caspofungin in the samples was determined using the peak area ratio and the regression parameters of the calibration curve. Tissue results in ng were converted to μg/g using the amount of tissue extracted and the final extract volume.

TABLE 23

| Instrument Operating Conditions SYSTEM: | 4000 QTrap LC-MS-MS (AB SCIEX, Foster City, CA) equipped with a 1200 HPLC (Agilent Technologies, Wilmington, DE) |
|---|---|
| HPLC CONDITIONS | |
| HPLC Column: | Kinetex Biphenyl 50 mm × 2.1 mm, 5 μm, 100 Å (Phenomenex, Torrance, CA) |
| Column Temperature | 25° C. |
| Injection Volume: | 5 μL |
| Flow Rate: | 300 μL/min |
| Mobile Phase A: | 0.1% formic acid in water |
| Mobile Phase B: | 0.1% formic acid in acetonitrile |

TABLE 23-continued

| Program: | Time (minutes) | Mobile Phase A (%) | Mobile Phase B (%) |
|---|---|---|---|
| | 0.00 | 70 | 30 |
| | 0.5 | 70 | 30 |
| | 1.0 | 5 | 95 |
| | 4.0 | 5 | 95 |
| | 4.1 | 70 | 30 |
| | 8.0 | 70 | 30 |
| Run Time: | 8 minutes | | |
| Retention Time: | Caspofungin and Internal Standard - approximately 2.3 minutes | | |
| MS-MS CONDITIONS | | | |
| Scan Type: | MRM | | |
| Ion Source: | Turbo Spray ESI | | |
| Ion Spray Voltage: | 5500 Volts | | |
| Polarity: | Positive | | |
| Ion Source Temperature: | 550° C. | | |
| Collision Energy: | Caspofungin and Internal Standard: 20 Volts | | |
| Ions monitored (Q1→Q3): | Caspofungin: 547.4 → 538.5; Internal Standard: 550.3→ 540.8 | | |
| Resolution: | Unit | | |
| Data System: | Analyst ® 1.6.3 (Applied Biosystems/MDS Sciex, Foster City, CA) | | |

Study Results: The pharmacokinetic experiment was performed as described. The concentrations of caspofungin in plasma, lung, kidney and liver tissues were determined and the results are depicted in the following figures and tables described below.

Comparison Between Inhalation Solution 2 (Inh2) and IV Solution Administered

Figure 2:
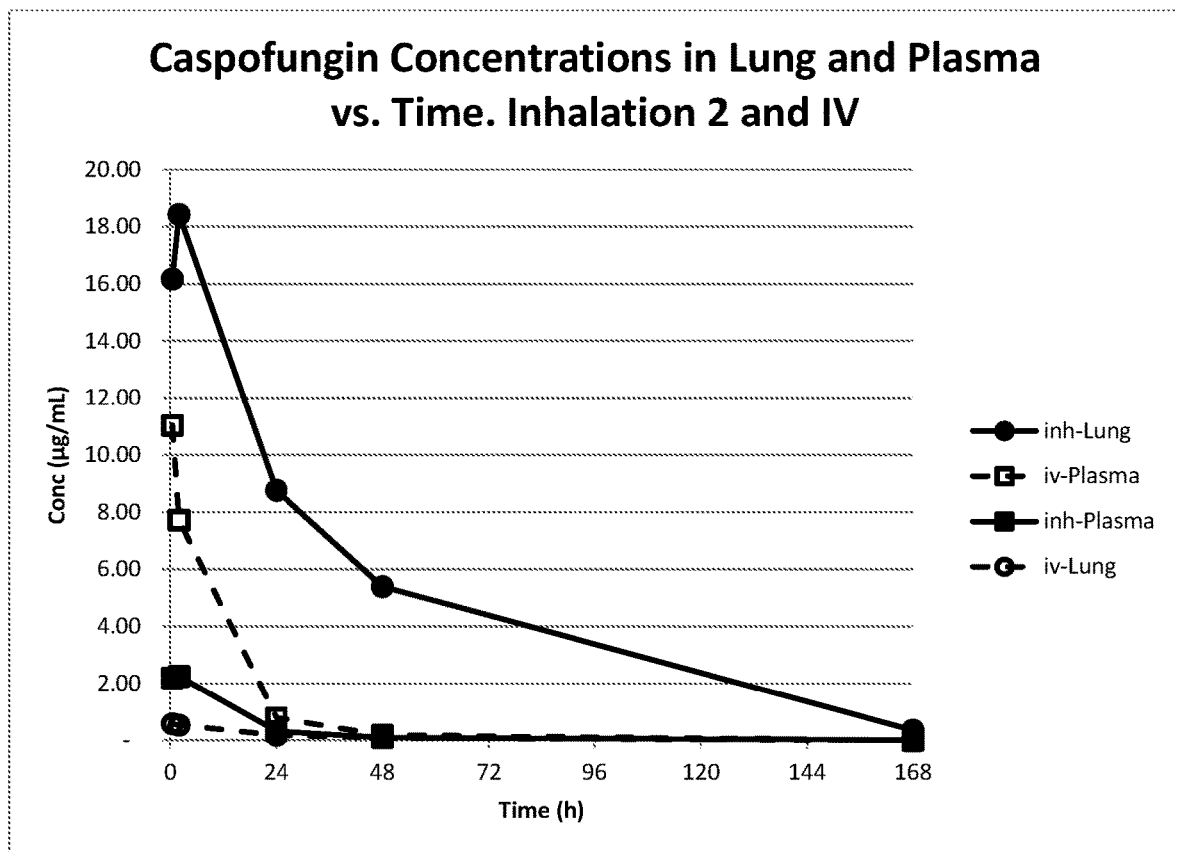
FIG. 2 shows the pharmacokinetics of caspofungin in rat lung and plasma when the caspofungin was delivered intravenously or via inhalation with inhalation solution 2 (inh2) at 2 mg/kg.

FIG. 2 shows the pharmacokinetics of caspofungin in rat lung and plasma when the caspofungin was delivered intravenously or via inhalation with inhalation solution 2 (inh2) at 2 mg/kg.

Figure 3:
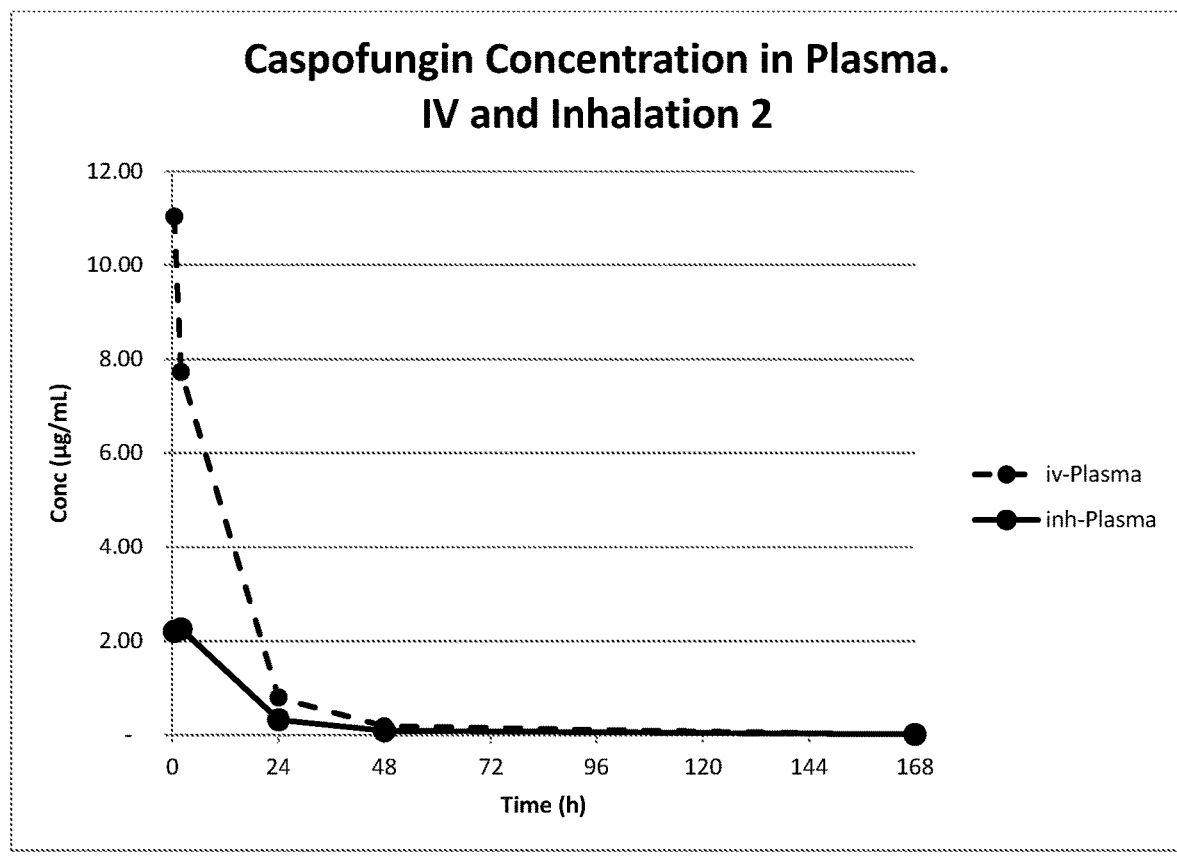
FIG. 3 shows the pharmacokinetics of caspofungin in rat plasma when the caspofungin was delivered intravenously or via inhalation with inhalation solution 2 (inh2) at 2 mg/kg.

FIG. 3 shows the pharmacokinetics of caspofungin in rat plasma when the caspofungin was delivered intravenously or via inhalation with inhalation solution 2 (inh2) at 2 mg/kg.

Figure 4:
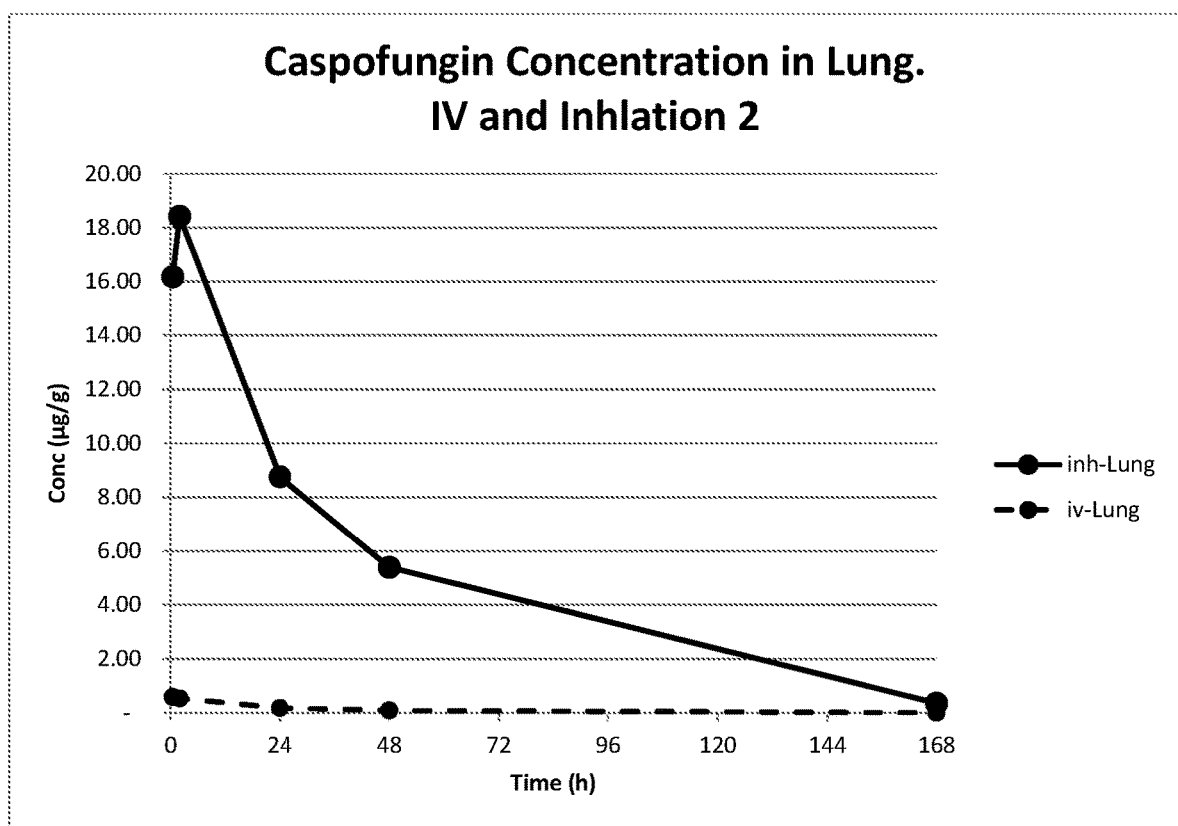
FIG. 4 shows the pharmacokinetics of caspofungin in rat lung tissue when the caspofungin was delivered intravenously or via inhalation with inhalation solution 2 (inh2) at 2 mg/kg.

FIG. 4 shows the pharmacokinetics of caspofungin in rat lung tissue when the caspofungin was delivered intravenously or via inhalation with inhalation solution 2 (inh2) at 2 mg/kg.

Figure 5:
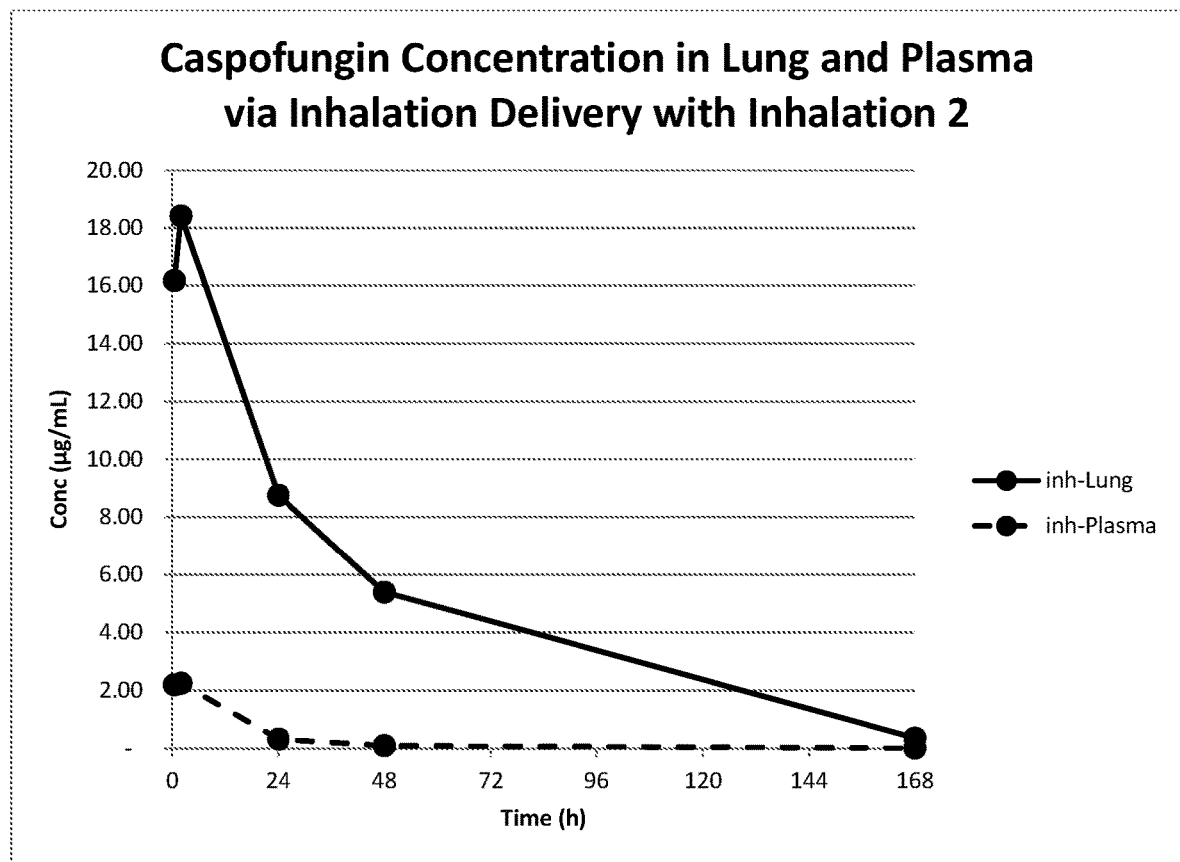
FIG. 5 shows the pharmacokinetics of caspofungin in rat plasma and lung when the caspofungin was delivered via inhalation with inhalation solution 2 (inh2) at 2 mg/kg.

FIG. 5 shows the pharmacokinetics of caspofungin in rat plasma and lung when the caspofungin was delivered via inhalation with inhalation solution 2 (inh2) at 2 mg/kg.

Figure 6:
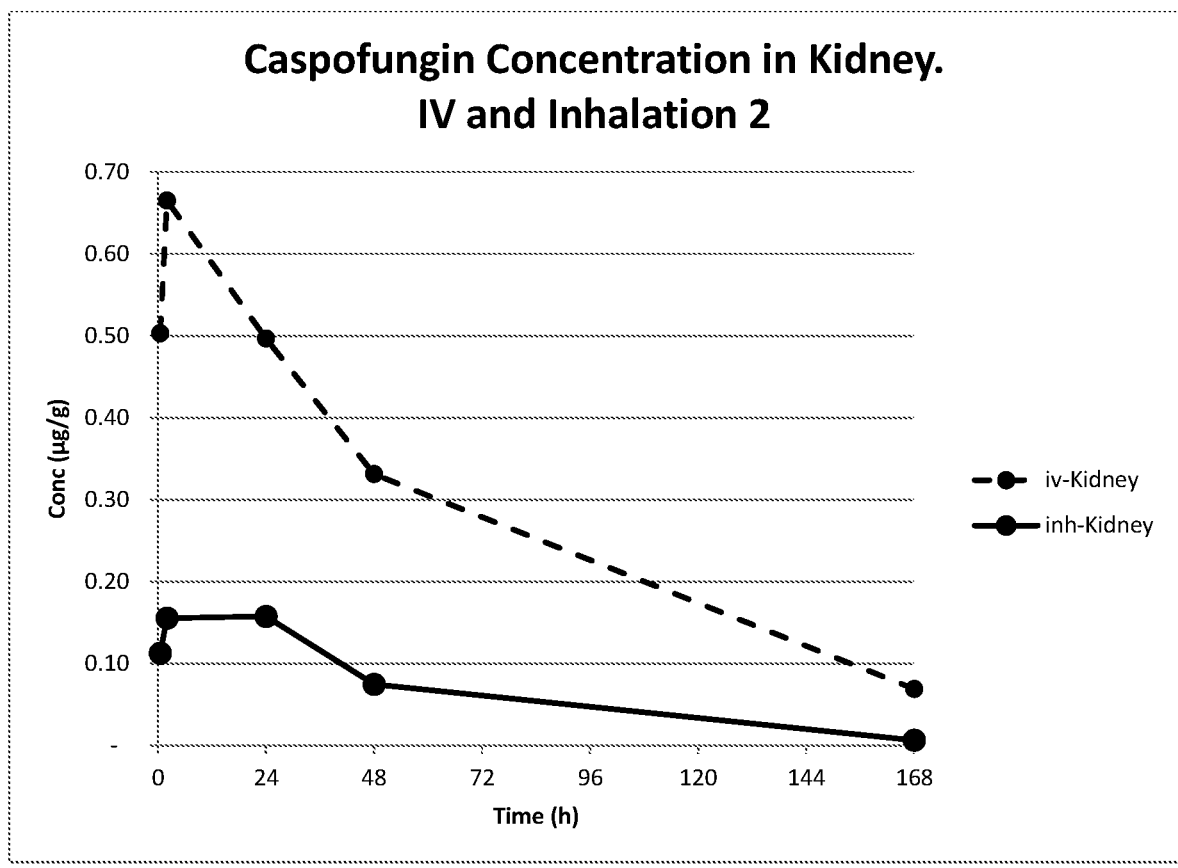
FIG. 6 shows the pharmacokinetics of caspofungin in rat kidney tissue when the caspofungin was delivered intravenously or via inhalation with inhalation solution 2 (inh2) at 2 mg/kg.

FIG. 6 shows the pharmacokinetics of caspofungin in rat kidney tissue when the caspofungin was delivered intravenously or via inhalation with inhalation solution 2 (inh2) at 2 mg/kg.

Figure 7:
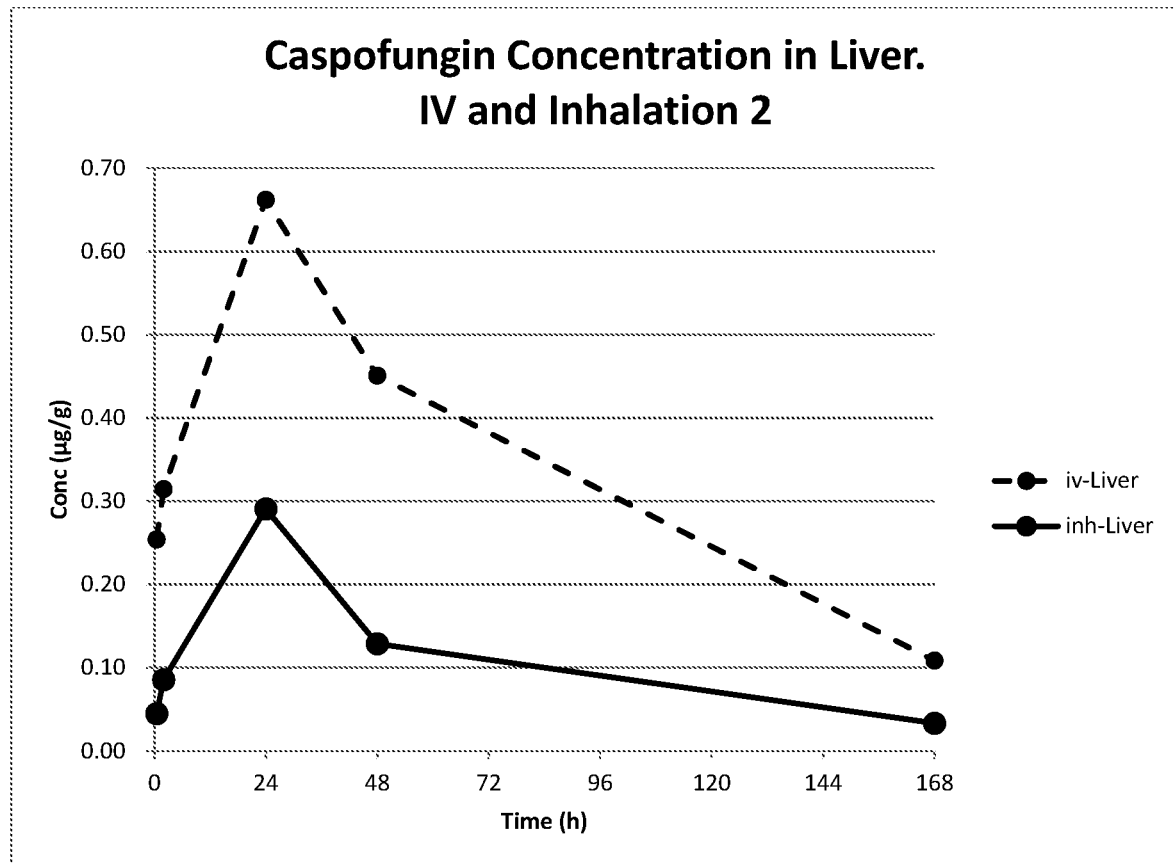
FIG. 7 shows the pharmacokinetics of caspofungin in rat liver tissue when the caspofungin was delivered intravenously or via inhalation with inhalation solution 2 (inh2) at 2 mg/kg.

FIG. 7 shows the pharmacokinetics of caspofungin in rat liver tissue when the caspofungin was delivered intravenously or via inhalation with inhalation solution 2 (inh2) at 2 mg/kg.

Tables 24-27 show the caspofungin concentration as indicated below.

TABLE 24

Caspofungin Concentrations in Rat Lungs.

| Time (h) | IV (μg/g) | Inhaled with Inhalation 2 (μg/g) | Inhaled/IV |
|---|---|---|---|
| 0.5 | 0.58 | 16.17 | 27.72 |
| 2 | 0.54 | 18.43 | 34.27 |
| 24 | 0.18 | 8.76 | 48.77 |

TABLE 24-continued

Caspofungin Concentrations in Rat Lungs.

| Time (h) | IV (µg/g) | Inhaled with Inhalation 2 (µg/g) | Inhaled/IV |
|---|---|---|---|
| 48 | 0.09 | 5.40 | 59.73 |
| 168 | 0.00 | 0.36 | — |

TABLE 25

Caspofungin Concentration in Rat Tissues Following Inhaled Delivery at a dose of 2 mg/kg with Inhalation 2.

| Time (h) | Lung (µg/g) | Plasma (µg/mL) | Kidney (µg/g) | Liver (µg/g) |
|---|---|---|---|---|
| 0.5 | 16.17 | 2.20 | 0.11 | 0.04 |
| 2 | 18.43 | 2.25 | 0.16 | 0.09 |
| 24 | 8.76 | 0.32 | 0.16 | 0.29 |
| 48 | 5.40 | 0.09 | 0.07 | 0.13 |
| 168 | 0.36 | 0.01 | 0.01 | 0.03 |

TABLE 26

Caspofungin Concentration in Rat Tissues Following IV Delivery at a dose of 2 mg/kg.

| Time (h) | Lung (µg/g) | Plasma (µg/mL) | Kidney (µg/g) | Liver (µg/g) |
|---|---|---|---|---|
| 0.5 | 0.58 | 11.03 | 0.50 | 0.25 |
| 2 | 0.54 | 7.72 | 0.67 | 0.31 |
| 24 | 0.18 | 0.80 | 0.50 | 0.66 |
| 48 | 0.09 | 0.19 | 0.33 | 0.45 |
| 168 | 0.00 | 0.00 | 0.07 | 0.11 |

TABLE 27

Lung/Tissue Concentrations Ratios Following Inhaled Delivery with Inhalation Solution 2.

| Time (h) | Lung/Plasma | Lung/Kidney | Lung/Liver |
|---|---|---|---|
| 0.5 | 7.36 | 143.27 | 360.68 |
| 2 | 8.19 | 118.37 | 215.52 |
| 24 | 27.16 | 55.53 | 30.15 |
| 48 | 57.11 | 71.97 | 41.93 |
| 168 | 29.18 | 52.17 | 10.68 |

Figure 8:
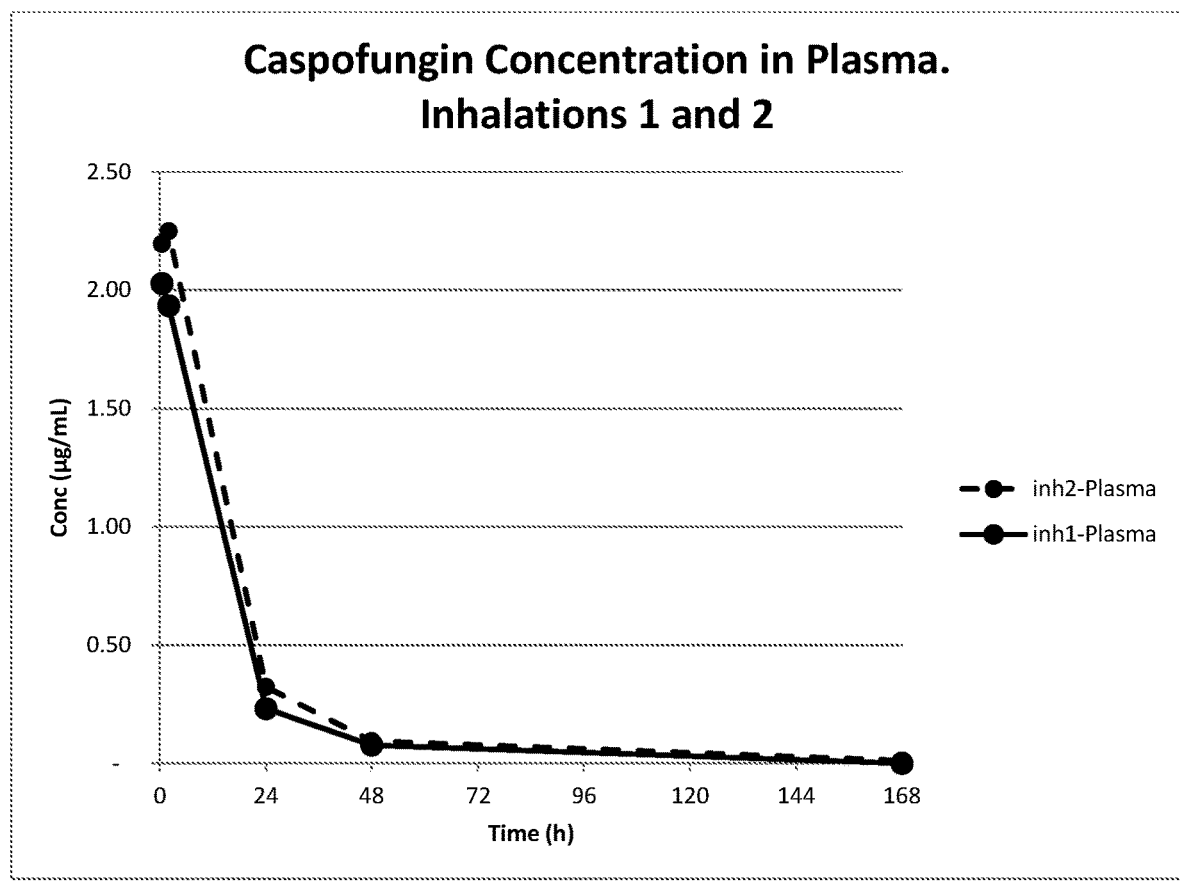
FIG. 8 shows the pharmacokinetics of caspofungin in rat plasma when the caspofungin was delivered via inhalation with inhalation solution 2 (inh2) and inhalation solution 1 (inh1) at 2 mg/kg.

Comparison Between Inhalation Solution 2 (Inh2) and Inhalation Solution 1 (Inh1) Administered FIG. 8 shows the pharmacokinetics of caspofungin in rat plasma when the caspofungin was delivered via inhalation with inhalation solution 2 (inh2) and inhalation solution 1 (inh1) at 2 mg/kg.

Figure 9:
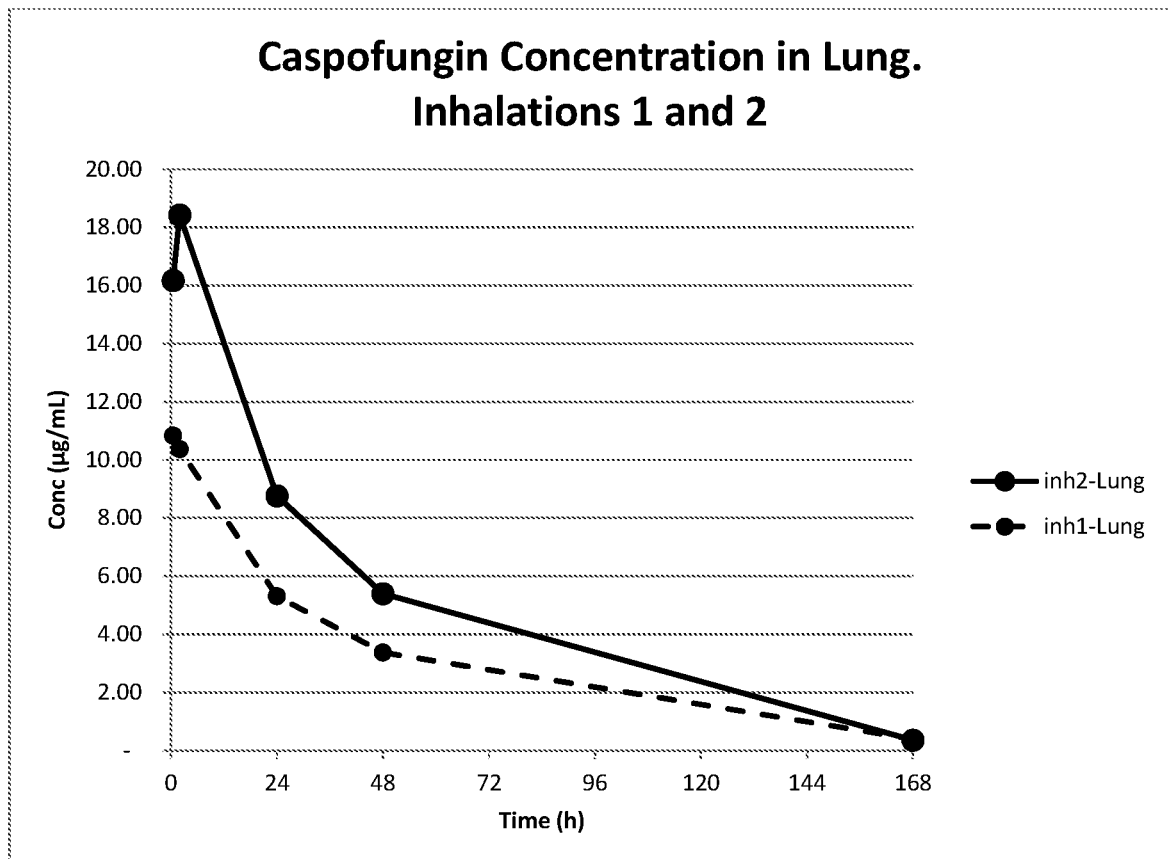
FIG. 9 shows the pharmacokinetics of caspofungin in rat lung tissue when the caspofungin was delivered via inhalation with inhalation solution 2 (inh2) and inhalation solution 1 (inh1) at 2 mg/kg.

FIG. 9 shows the pharmacokinetics of caspofungin in rat lung tissue when the caspofungin was delivered via inhalation with inhalation solution 2 (inh2) and inhalation solution 1 (inh1) at 2 mg/kg.

Figure 10:
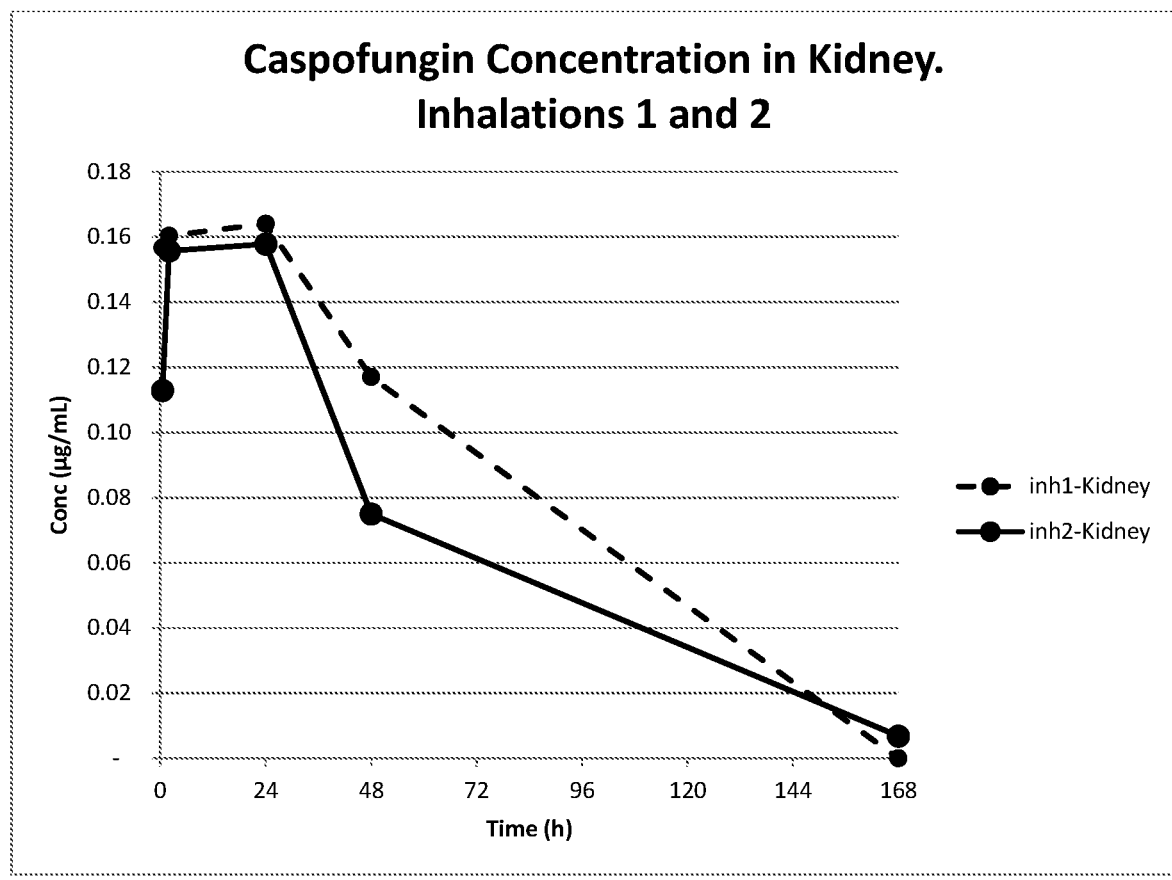
FIG. 10 shows the pharmacokinetics of caspofungin in rat kidney tissue when the caspofungin was delivered via inhalation with inhalation solution 2 (inh2) and inhalation solution 1 (inh1) at 2 mg/kg.

FIG. 10 shows the pharmacokinetics of caspofungin in rat kidney tissue when the caspofungin was delivered via inhalation with inhalation solution 2 (inh2) and inhalation solution 1 (inh1) at 2 mg/kg.

Figure 11:
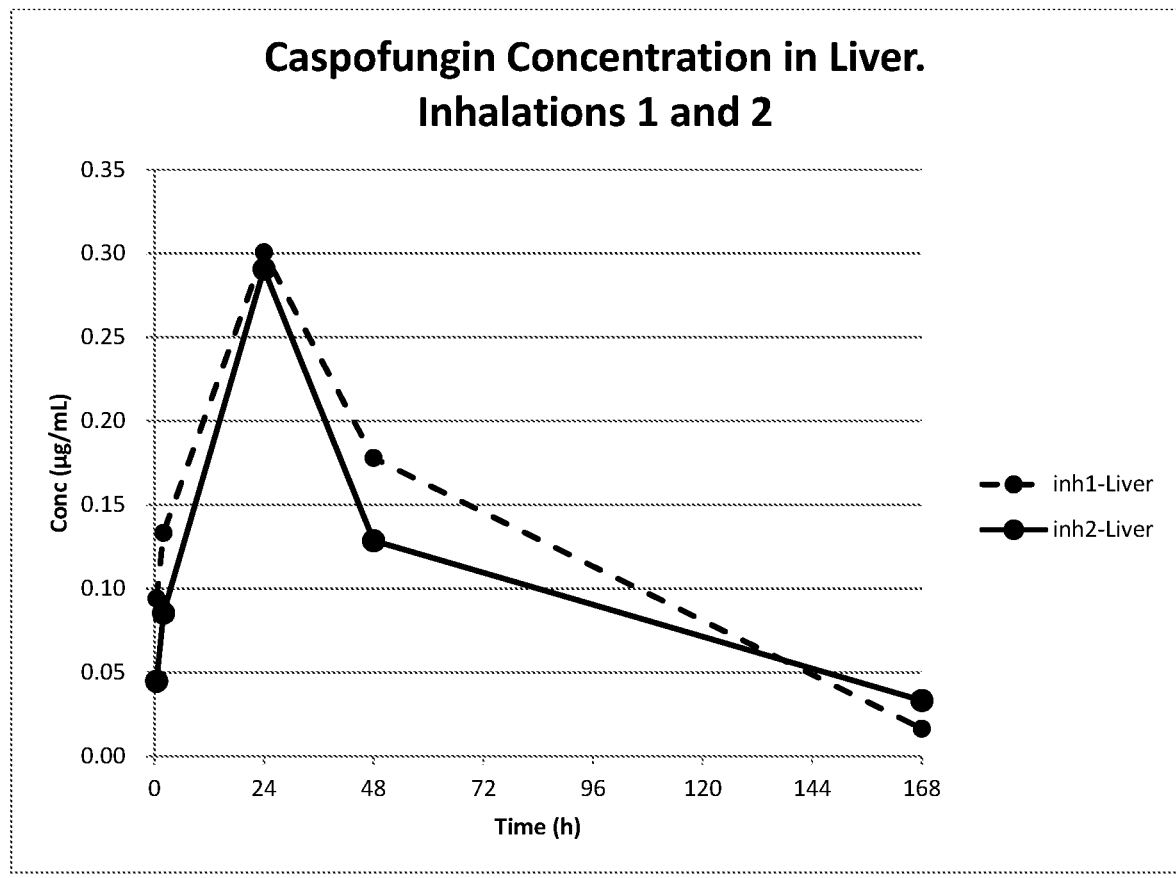
FIG. 11 shows the pharmacokinetics of caspofungin in rat liver tissue when the caspofungin was delivered via inhalation with inhalation solution 2 (inh2) and inhalation solution 1 (inh1) at 2 mg/kg.

FIG. 11 shows the pharmacokinetics of caspofungin in rat liver tissue when the caspofungin was delivered via inhalation with inhalation solution 2 (inh2) and inhalation solution 1 (inh1) at 2 mg/kg.

Tables 28-33 show the caspofungin concentration as indicated below.

TABLE 28

Caspofungin Concentration in Rat Tissues Following Inhaled Delivery at a dose of 2 mg/kg with Inhalation 1.

| Time (h) | Lung (µg/g) | Plasma (µg/mL) | Kidney (µg/g) | Liver (µg/g) |
|---|---|---|---|---|
| 0.5 | 10.83 | 2.03 | 0.16 | 0.09 |
| 2 | 10.37 | 1.93 | 0.16 | 0.13 |
| 24 | 5.31 | 0.23 | 0.16 | 0.30 |
| 48 | 3.37 | 0.08 | 0.12 | 0.18 |
| 168 | 0.39 | 0.00 | 0.00 | 0.02 |

TABLE 29

Lung/Tissue Concentrations Ratios Following Inhaled Delivery with Inhalation Solution 1.

| Time (h) | Lung/Plasma | Lung/Kidney | Lung/Liver |
|---|---|---|---|
| 0.5 | 5.33 | 67.69 | 120.33 |
| 2 | 5.37 | 64.81 | 79.77 |
| 24 | 23.09 | 33.19 | 17.70 |
| 48 | 42.13 | 28.08 | 18.72 |

TABLE 30

Caspofungin Concentrations and Ratios in Rat Plasma Following Inhaled Delivery with Inhalation Solution 1 and Inhalation Solution 2.

| Time (h) | Inhaled with Inhalation 2 (Inh2, µg/g) | Inhaled with Inhalation 1 (Inh1, µg/g) | Inh2/Inh1 |
|---|---|---|---|
| 0.5 | 2.20 | 2.03 | 1.08 |
| 2 | 2.25 | 1.93 | 1.16 |
| 24 | 0.32 | 0.23 | 1.39 |
| 48 | 0.09 | 0.08 | 1.23 |
| 168 | 0.01 | 0.00 | — |

TABLE 31

Caspofungin Concentrations and Ratios in Rat Lung Tissue Following Inhaled Delivery with Inhalation Solution 1 and Inhalation Solution 2.

| Time (h) | Inhaled with Inhalation 2 (Inh2, µg/g) | Inhaled with Inhalation 1 (Inh1, µg/g) | Inh2/Inh1 |
|---|---|---|---|
| 0.5 | 16.17 | 10.83 | 1.49 |
| 2 | 18.43 | 10.37 | 1.78 |
| 24 | 8.76 | 5.31 | 1.65 |
| 48 | 5.40 | 3.37 | 1.60 |
| 168 | 0.36 | 0.39 | 0.90 |

TABLE 32

Caspofungin Concentrations and Ratios in Rat Kidney Tissue Following Inhaled Delivery with Inhalation Solution 1 and Inhalation Solution 2.

| Time (h) | Inhaled with Inhalation 2 (Inh2, µg/g) | Inhaled with Inhalation 1 (Inh1, µg/g) | Inh2/Inh1 |
|---|---|---|---|
| 0.5 | 0.11 | 0.16 | 0.72 |
| 2 | 0.16 | 0.16 | 0.97 |
| 24 | 0.16 | 0.16 | 0.96 |
| 48 | 0.07 | 0.12 | 0.64 |
| 168 | 0.01 | 0.00 | — |

TABLE 33

Caspofungin Concentrations and Ratios in Rat Liver Tissue Following Inhaled Delivery with Inhalation Solution 1 and Inhalation Solution 2.

| Time (h) | Inhaled with Inhalation 2 (Inh2, μg/g) | Inhaled with Inhalation 1 (Inh1, μg/g) | Inh2/Inh1 |
|---|---|---|---|
| 0.5 | 0.04 | 0.09 | 0.48 |
| 2 | 0.09 | 0.13 | 0.64 |
| 24 | 0.29 | 0.30 | 0.97 |
| 48 | 0.13 | 0.18 | 0.72 |
| 168 | 0.03 | 0.02 | 2.02 |

Table 34 shows the MIC and MEC for *Aspergillus* spp. isolate susceptibility to caspofungin based from MIC data from Table 4, Caspofungin Acetate FDA Advisory Committee Meeting Background, Merck 2000 and MEC data from Espinel-Ingrof et al. Wild-Type MIC Distributions and Epidemiological Cutoff Values for Caspofungin and *Aspergillus* spp. for the CLSI Broth Microdilution Method, *Antimicrob. Agents Chemo.*, 2011, 55, 6, p 2855-2858.

TABLE 34

| | $MIC_{90}$ (μg/mL) | | | MEC (μg/mL) | | |
|---|---|---|---|---|---|---|
| Species | No. isolates | Range | Average[a] | No. isolates | Range | Average[b] |
| Aspergillus fumigatus | 56 | 0.12-4 | 0.25 | 1691 | 0.016-32 | 0.25 |
| Aspergillus flavus | 13 | 0.06-2 | 0.2 | 432 | 0.016-32 | 0.06 |
| Aspergillus nidulans | 13 | 0.2-4 | 0.44 | 192 | 0.032-16 | 0.12 |
| Aspergillus niger | 10 | 0.06-0.5 | 0.14 | 440 | 0.016-2 | 0.06 |
| Aspergillus terrus | 11 | 0.06-.2 | 0.12 | 385 | 0.016-2 | 0.06 |
| Aspergillus versicolor | | | | 75 | 0.032-2 | 0.12 |

[a] Geometric Mean MIC
[b] b. Mode - most frequent minimum effective concentration (MEC)

Table 35 shows the MIC *Candida* spp. isolate susceptibility to caspofungin based from Pfaller et al. Correlation of MIC with Outcome for *Candida* Species Tested against Caspofungin, Anidulafungin, and Micafungin: Analysis and Proposal for Interpretive MIC Breakpoints, *J. Clin Microbiol*, 2008, 46, 8, p 2620-2629.

TABLE 35

| Species | No. isolates | $MIC_{90}$ (μg/mL) |
|---|---|---|
| Candida albicans | 2869 | 0.06 |
| Candida glabrata | 747 | 0.06 |
| Candida tropicalis | 625 | 0.06 |
| Candida krusei | 136 | 0.25 |
| Candida parapsilosis | 759 | 1 |
| Candida guilliermondii | 61 | 1 |
| All Candida spp. | 5,346 | 0.25 |

The half-life of caspofungin in the lung, as determined from the studies described herein, is 39 hours i.e. every 39 hours 50% of the remaining drug is eliminated from the lung for Inhalation Solution 1. A projection of the amount of caspofungin remaining in the lung following a time period equivalent to one half-life following the administration of Inhalation Solution 1 is shown below in Table 36. The half-life of caspofungin in the lung, as determined from the studies described herein, is 32 hours i.e. every 32 hours 50% of the remaining drug is eliminated from the lung for Inhalation Solution 2. A projection of the amount of caspofungin remaining in the lung following a time period equivalent to one half-life following the administration of Inhalation Solution 2 is shown below in Table 37. The lung concentration columns show two starting concentrations; one is the concentration measured in the rat lung from the 2 mg/kg dose, the second is the projected concentration that would result from an inhaled dose of 7.2 mg/kg. To be effective the drug concentration should remain above the MIC and MEC. The average MIC and MEC for caspofungin versus *Aspergillus fumigatus*, the species most commonly associated with Aspergillosis is 0.25 μg/mL.

TABLE 36

Inhalation Solution 1.

| | | Drug | Lung Concentration (μg/g) | |
|---|---|---|---|---|
| Hours | Days | Remaining | 2 mg/kg | 7.2 mg/kg |
| 0 | — | 100% | 10.83 | 38.99 |
| 39 | 1.6 | 50% | 5.42 | 19.49 |
| 78 | 3.3 | 25% | 2.71 | 9.75 |

TABLE 36-continued

Inhalation Solution 1.

| | | Drug | Lung Concentration (μg/g) | |
|---|---|---|---|---|
| Hours | Days | Remaining | 2 mg/kg | 7.2 mg/kg |
| 117 | 4.9 | 13% | 1.35 | 4.87 |
| 156 | 6.5 | 6% | 0.68 | 2.44 |
| 195 | 8.1 | 3% | 0.34 | 1.22 |

TABLE 37

Inhalation Solution 2.

| | | Drug | Lung Concentration (μg/g) | |
|---|---|---|---|---|
| Hours | Days | Remaining | 2 mg/kg | 7.2 mg/kg |
| 0 | — | 100% | 16.17 | 58.21 |
| 32 | 1.3 | 50% | 8.09 | 29.11 |
| 64 | 2.7 | 25% | 4.04 | 14.55 |
| 96 | 4.0 | 13% | 2.02 | 7.28 |
| 128 | 5.3 | 6% | 1.01 | 3.64 |
| 160 | 6.7 | 3% | 0.51 | 1.82 |
| 192 | 8.0 | 1.50% | 0.25 | 0.91 |

The measurement of the particles produced during the inhalation experiment with Inhalation Solution 1 showed that they had a MMAD=1.15 μm with a GSD (geometric standard deviation) of 2.67. The measurement of the particles produced during the inhalation experiment with Inhalation Solution 2 showed that they had a MMAD=1.21 μm with a GSD (geometric standard deviation) of 2.31.

Example 5: Comparative Tissue Distribution Studies of Caspofungin

A pharmacokinetic study was performed in rats to investigate the distribution of caspofungin parent compound to the organs most associated with Aspergillosis and compound safety (i.e. lungs, liver and kidney) when delivered either through an intravenous or inhaled route. A comparison with the radiolabeled data from Stone 2004 (Stone, et. al. Disposition of Caspofungin: Role of Distribution in Determining Pharmacokinetics in Plasma, *Antimicrob. Agents Chemo.*, 2004, 48, 3, p 815-823) is shown in Table 38, and the studies shown below are for IV. IV study presented below at the 24 hour time point is in line with IV data previously reported by Sandhu 2004 (Sandhu et al., Disposition of Caspofungin, a Novel Antifungal Agent, in Mice, Rats, Rabbits, and Monkeys, *Antimicrob. Agents Chemo.*, 2004, 48, 4, p 1272-1280). It is clear that the amounts of caspofungin recovered from the IV dosed study are substantially different from the previously reported caspofungin concentrations. Not only are the distributions significantly different, but they are in no way predictable.

TABLE 38

| Time (h) | Plasma (μg/mL) | | Lung (μg/g) | | Kidney (μg/g) | | Liver (μg/g) | |
|---|---|---|---|---|---|---|---|---|
| | Stone 2004[a] | IV study[b] | Stone 2004[a] | IV study[b] | Stone 2004[a] | IV study[b] | Stone 2004[a] | IV study[b] |
| 0.5 | 11 | 11.03 | 5.12 | 0.58 | 9.15 | 0.50 | 5.03 | 0.25 |
| 2 | 6.1 | 7.72 | 4.50 | 0.54 | 10.60 | 0.67 | 7.04 | 0.31 |
| 24 | 1.74 | 0.80 | 2.44 | 0.18 | 11.40 | 0.50 | 22.20 | 0.66 |

*Both studies dosed at 2 mg/kg
[a] quantities are of radiolabeled compound
[b] quantities are parent caspofungin acetate Example 7: Stability Studies with Reconstituted Solutions The lyophilized formulations, such as any one of the formulations described in Example 2 (i.e., Formulations 1-3, 7-9, and 13-17, are reconstituted with saline or buffered PBS to provide reconstituted solutions. The reconstituted solutions are stored under appropriate storage conditions, such as at about 5° C. or about 25° C. after 0 hours, 12 hours, 24 hours, 48 hours, or 72 hours. The % of caspofungin remaining and/or any degradation products are determined through HPLC analysis as described in Example 2.

Preparation of the Reconstituted Solutions of Formulations 16 and 17.

The lyophilized vials of Formulation 16 and 17 were prepared as described in Example 2 (Table 39). One vial of the lyophilized cake was reconstituted in 1 mL of 0.9% saline to obtain a 10 mg/mL caspofungin diacetate solution. An aliquot (55 μL) was removed and diluted with 1 mL of deionized water for HPLC analysis.

CANCIDAS®:

Reconstituted according to the Package Insert; the manufacture's instruction for preparation of the daily 50-mg infusion is to aseptically add 10.5 mL of 0.9% NaCl injection, Bacteriostatic Water for Injection with methylparaben and propylparaben, or Bacteriostatic Water for Injection with 0.9% benzyl alcohol to the CANCIDAS® 50-mg vial. The reconstituted solution may be stored for up to one hour at <25° C. (<77° F.).

The reconstituted solution stability of Formulations 16 and 17 are tested and stable at 25° C. up to 7 hours and at 5° C. up to 240 hours (Table 40 and 41).

TABLE 39

| | Form 16 | Form 17 |
|---|---|---|
| Caspofungin diacetate (mg) | 10 | 10 |
| Povidone K30 (mg) | 40 | 40 |
| Total Lyo Volume (mL) | 0.5 | 0.5 |
| Acetate buffer pH | 6 | 6 |
| Povidone/Caspofungin diacetate ratio | 4:1 | 4:1 |
| Appearance After lyophilization | white cake | white cake |
| KF water content of lyo cake % | 0.74 | 0.92 |
| Reconstituted Volume (mL) | 1.0 | 1.0 |
| Reconstituted solution HPLC Purity %@T0 | 99.34 | 99.38 |

TABLE 40

HPLC Purity of Reconstituted Solution Stability of Formulations 16 and 17 at 25° C.

| HPLC Purity % | Form 16 | Form 17 |
|---|---|---|
| HPLC Purity % 25° C. @T0 | 99.34 | 99.38 |
| HPLC Purity % 25° C. @T1 hr | 99.25 | 99.33 |
| HPLC Purity % 25° C. @T4 hr | 99.00 | 99.04 |
| HPLC Purity % 25° C. @T7 hr | 98.93 | 98.73 |

TABLE 41

HPLC Purity of Reconstituted Solution Stability of Formulations 16 and 17 at 5° C.

| HPLC Purity % | Form 16 | Form 17 |
|---|---|---|
| HPLC Purity % 5° C. @T0 | 99.34 | 99.38 |
| HPLC Purity % 5° C. @T1 hr | 99.39 | 99.37 |
| HPLC Purity % 5° C. @T4 hr | 99.38 | 99.27 |
| HPLC Purity % 5° C. @T7 hr | 99.31 | 99.31 |
| HPLC Purity % 5° C. @T24 hr | 99.34 | 99.26 |
| HPLC Purity % 5° C. @T72 hr | 99.09 | 99.15 |
| HPLC Purity % 5° C. @T96 hr | 99.17 | 99.15 |
| HPLC Purity % 5° C. @T168 hr | 98.67 | 98.68 |
| HPLC Purity % 5° C. @T240 hr | 98.67 | 98.43 |

Example 8: Aerosolization Studies with PBS Solutions

The aerosolization studies as described in the Example 1 are performed with the different combinations of caspofungin diacetate and polyvinylpyrrolidone (PVP K30) below. The stock solutions of caspofungin diacetate (100 mg/ml) and polyvinylpyrrolidone (PVP K30, 100 mg/mL) are prepared. Six different combination are prepared and tested and their concentrations are listed in Table 42. In addition, PBS buffer are used to generate aerosols for the purpose of comparing particle size.

Methods: Test Solution Preparation and Composition:
1. Preparation of Caspofungin Diacetate Stock Solution:
   500 mg of caspofungin diacetate is dissolved in 5.0 mL of PBS buffer to obtain 5 mL of caspofungin diacetate stock solution. The concentration should be close to 100 mg/mL° (assuming the density of the stock solution is close to 1).

2. Preparation of PVP K30 Stock Solution:
   In a 25 mL volumetric flask 2.5 g of PVP K30 is dissolved in 20 mL PBS buffer. The pH is adjusted to 6 with 1N NaOH solution. Normal saline is added to the mark and is mixed well. This provides 100 mg/mL PVP K30 stock solution.

The table below shows the proposed aerosolization formulations.

TABLE 43

Aerosolization Formulations
Formulation Configuration

| | Solution Number | | | | | | |
|---|---|---|---|---|---|---|---|
| | B1 | B2 | B3 | B4 | B5 | B6 | B7 |
| Caspofungin diacetate final concentration, mg/mL | 5 | 5 | 5 | 10 | 10 | 10 | PBS Buffer |
| PVP concentration final concentration, mg/mL | 5 | 10 | 20 | 10 | 20 | 40 | |
| Caspofungin diacetate/PVP K30 ratio (w/w) | 1:1 | 1:2 | 1:4 | 1:1 | 1:2 | 1:4 | |
| Caspofungin diacetate Stock (100 mg/mL) in mL | 0.5 | 0.5 | 0.5 | 1 | 1 | 1 | |
| PVP K30 Stock (100 mg/mL) in mL | 0.5 | 1 | 2 | 1 | 2 | 4 | |
| PBS Buffer Solution (approx volumes) in mL | 9 | 8.5 | 7.5 | 8 | 7 | 5 | |
| Total (fill to mark in 10 mL vol flask w saline) | 10 | 10 | 10 | 10 | 10 | 10 | |

Example 9: Pharmacokinetic Studies with Caspofungin Formulations

The pharmacokinetic studies as described in Example 3 are performed with the following inhalation formulations as described below.

Test Article Preparation for Inhalation Solution 1 (PBS-Inh1)

One day prior to the study day, caspofungin diacetate is transferred from the −70° C. freezer to −20° C. freezer overnight. On the study day, caspofungin diacetate is transferred from −20° C. freezer to 4° C. refrigerator for 2 hrs. Prior to opening the vial, the vial is stored in a room temperature desiccator for 1 hour to allow the contents to come to room temperature.

For inhalation exposure, a 10 mg/mL dosing solution is prepared by dissolving 800 mg of caspofungin diacetate powder in 80 mL of PBS buffer solution. The resulting solution is aseptically filtered and is kept refrigerated between 2-8° C. until used. The formulation is aerosolized for inhalation administration.

Test Article Preparation for Inhalation Solution 2 (PBS-Inh2)

1. Preparation of Caspofungin Diacetate Stock Solution 800 mg of caspofungin diacetate, which is warmed from storage as previously described, is dissolved in 8.0 mL of PBS buffer to obtain 8 mL of caspofungin diacetate stock solution. The concentration should be close to 100 mg/mL (assuming the density of the stock solution is close to 1).

2. Preparation of PVP K30 Stock Solution

In a 50 mL volumetric flask, 5.0 g of PVP K30 is dissolved in 45 mL of PBS buffer. The pH is adjusted to 6 with 1N NaOH solution dropwise. PBS buffer is added to the mark, approximately 5 mL, and is mixed well to give a total volume of 50 mL. This provides 100 mg/mL PVP K30 stock solution.

3. Preparation of Test Article: Caspofungin Diacetate (10 mg/mL), PVP K30 (40 mg/ML)

In a 100 mL flask or glass bottle, 8.0 mL of caspofungin diacetate stock solution and 32 ml of PVP stock solution are added. 40 mL of PBS buffer is added in the flask and is gently well mixed. The solution is sterile filtered through a 0.2-micron filter using a slight vacuum into a sterile 100 mL flask or bottle. The flask is stoppered. The test article is stored at 4° C. until use.

TABLE 44

| Caspofungin diacetate final concentration | 10 mg/mL |
|---|---|
| PVP concentration final concentration | 40 mg/mL |
| Caspofungin diacetate/PVP K30 ratio (w/w) | 1:4 |
| Caspofungin diacetate Stock (100 mg/mL) | 8 mL |
| PVP K30 Stock (100 mg/mL) | 32 mL |
| PBS buffer (approx volumes) | 40 mL |
| Total | 80 mL |

Example 10: Prophylactic Efficacy of Aerosol Caspofungin in Experimental Pulmonary Aspergillosis The objective of the study is to determine the antifungal efficacy of any one of the caspofungin compositions or formulations described herein administered via inhalation therapy in the prophylaxis of invasive pulmonary aspergillosis in rats.

The experimental procedures are performed according to the procedures described in van de Cicogna et. al., *Antimicrob. Agents Chemother.* 1997, 41, 259-261 with further modifications. Caspofungin is used instead of amphotericin B.

The caspofungin formulation used herein include any one of the formulations as described herein, such as those from Examples 1-3, 8, and 9, or any one of the following formulations: Formulations 1-3, 7-9, and 13-17.

Male Sprague-Dawley rats (Charles River Breeding Laboratories, Wilmington, Mass.) are fed a low-protein diet (8% protein, Dyet, Bethlehem, Pa.) and are given a suitable amount of tetracycline (i.e. 250 mg dissolved in 750 mL of drinking water) to prevent bacterial infection. Furthermore, rats are treated with subcutaneous injections of cortisone acetate (150 mg/kg of body weight) three times a week under anesthesia with enflurane. These injections are either given for two weeks until the day of injection (trial 1) or throughout the duration of the experiment (trial arm 2).

*Aspergillus fumigatus* H11-20 is obtained from a steroid-treated rat dying from spontaneously acquired pulmonary aspergillosis. Other clinical strains of *Aspergillus fumigatus* are also suitable for these experiments. Suitable pores are obtained from subculturing the organism on Sabouraud dextrose for an appropriate time (i.e. 4 to 5 days) and are harvested with 0.02% Tween 80 and washed with sterile saline. The final suspension containing the desired amount of spores/mL, such as $10^7$ spores/mL, is prepared and confirmed by counting with a hemocytometer.

General anesthesia in rats is induced with inhaled enflurane, wherein a suitable amount of the *Aspergillus* spore suspension (i.e., 0.1 mL to deliver $10^6$ spores) is injected with a syringe to the exposed trachea. Wounds are closed surgical staples.

The rats are administered the formulations of caspofungin as described above with an inhalation device, such as a jet nebulizer or an ultrasonic nebulizer, in a glass chamber. Rats are treated at an appropriate time point before infection, such as 48 hours. The estimated amount of drug inhaled by the rats is calculated from the concentration of the product in the chamber, the minute volume of the rats (lung volume times respiratory rate), and exposure time.

For trial 1, rats (8-10 rats in each group) are either treated with a placebo, such as sterile water, or with a suitable dose of caspofungin at a suitable time period before infection (i.e., 48 hours). Immunosuppressive treatments with cortisone acetate are discontinued after time of infection. Rats in this group are monitored for survival on daily basis for an appropriate amount of time (i.e., 7 days).

For trial 2, rats (8-10 rats in each group) are either treated with a placebo, such as sterile water or with an appropriate dose of caspofungin at a suitable time period before infection (i.e., 48 hours). Immunosuppressive treatments with cortisone acetate are continued for the duration of the experiment after infection (i.e., 14 days).

The outcome variables used to assess efficacy of this study include but are not limited: survival of the infected rats during therapy and after termination of therapy and caspofungin concentration in the lung tissue and other organs (liver, kidney, spleen, and pancreas) and plasma.

Example 11: Antifungal Efficacy of Caspofungin in Treatment of Experimental Pulmonary Aspergillosis in Transiently Neutropenic Rats The objective of the study is to determine the antifungal efficacy of any one of the caspofungin compositions or formulations described herein administered via inhalation therapy in the treatment of invasive pulmonary aspergillosis in transiently neutropenic rats.

The experimental procedures are performed according to the procedures described in van de Sande et. al., *Antimicrob. Agents Chemother.* 2008, 52, 1345-1350 with further modifications.

The caspofungin formulation used herein include any one of the formulations as described herein, such as those from Examples 1-3, 8, and 9, or any one of the following formulations: Formulations 1-3, 7-9, and 13-17.

A clinical strain of *Aspergillus fumigatus* is obtained from a hemato-oncological patient with pulmonary aspergillosis. The strain is passed through neutropenic rats and maintained on Sabouraud agar slants in order to maintain the strain's virulence. The minimal inhibitory concentration (MIC) and minimal effective concentration (MEC) of the strain used for this experiment against caspofungin are determined accordingly.

Infection Model and Antifungal Treatment

The rat model of aerogenic left-sided invasive pulmonary aspergillosis as described in van de Sande et. al., *Antimicrob. Agents Chemother.* 2008, 52, 1345-1350 is used. Neutropenia is induced by intraperitoneal administration of a suitable dose of cyclophosphamide, such as 75 mg/kg, and is administered before inoculation (i.e., 5 days) followed by administration of a suitable dose prior to inoculation (i.e., 60 mg/kg 1 day before inoculation) and several doses following inoculation (i.e., 50, 40, and 30 mg/kg on days 3, 7, and 11 after fungal inoculation).

Fungal infection is established by intubation of the left main bronchus while the rats are under general anesthesia. A cannula is passed through the tube, and the left lobe is inoculated with the appropriate amount of aspergillosis, such as $6 \times 10^4$ conidia.

Antifungal therapy is initiated at a suitable time point after inoculation, such as 16 h, 24 h, or 72 h after inoculation. The rats are administered the formulations of caspofungin as described above with an inhalation device, such as a jet nebulizer or an ultrasonic nebulizer, in an appropriate dose (i.e., 4 mg/kg or 10 mg/kg) and suitable dosing schedule, such as once a day, once every two days, or once every three days. The antifungal therapy is continued for a suitable amount of time, such as 7 days, 14 days, or 21 days.

Outcome Variables

The outcome variables used to assess efficacy include but not limited to following: survival of the infected rats during therapy and after termination of therapy, pulmonary infarct score, lung weight, residual, fungal burden (log CFU/gram), fungal growth (log CFU/gram) in bronchoalveolar lavage fluid, computerized tomograph (CT) scores, galactomannan index (GMI), and histopathology.

Example 12: Antifungal Efficacy of Caspofungin for Prophylaxis of Experimental Pulmonary Aspergillosis in Transiently Neutropenic Rats The objective of the study is to determine the antifungal efficacy of any one of the caspofungin compositions or formulations described herein administered via inhalation therapy in the prophylaxis of invasive pulmonary aspergillosis in transiently neutropenic rats.

The experimental procedures are performed according to the procedures described in van de Sande et. al., *Antimicrob. Agents Chemother.* 2008, 52, 1345-1350 with further modifications.

The caspofungin formulation used herein include any one of the formulations as described herein, such as those from Examples 1-3, 8, and 9, or any one of the following formulations: Formulations 1-3, 7-9, and 13-17.

To assess the efficacy of caspofungin inhalation therapy for the prophylaxis of pulmonary aspergillosis in a transiently neutropenic rat model, the same methods used for the assessing the therapeutic efficacy as described in Example 11 are utilized with the following exceptions: caspofungin administration via inhalation is started at a suitable time period before inoculation (i.e., 24 to 48 hours before infection); and a lower load of administered inoculum is administered in order to simulate the low initial tissue burden of *A. fumigatus*. Similar outcome variables as described in Example 11 are used to assess efficacy.

What is claimed is:

1. A stabilized composition suitable for inhalation administration comprising
   i) caspofungin, or a polymorph, pharmaceutically acceptable salt, hydrate, or solvate thereof; and
   ii) polyvinylpyrrolidone (PVP)
   wherein a weight ratio of polyvinylpyrrolidone (PVP) to caspofungin, or the polymorph, pharmaceutically acceptable salt, hydrate, or solvate thereof, is from about 2:1 to about 4:1, and wherein the stabilized composition comprises after storage greater than about 95% of caspofungin, or a polymorph, pharmaceutically acceptable salt, hydrate, or solvate thereof that has not degraded after storage at about 25° C. for about 8 weeks, and wherein the PVP stabilizes purity of caspofungin.

2. The stabilized composition of claim 1, wherein the pharmaceutically acceptable salt of caspofungin is the acetate salt.

3. The stabilized composition of claim 2, wherein the composition comprises from about 1 mg to about 100 mg of caspofungin acetate.

4. The stabilized composition of claim 1, wherein the weight ratio of polyvinylpyrrolidone (PVP) to caspofungin, or the polymorph, pharmaceutically acceptable salt, hydrate, or solvate thereof is about 4:1.

5. The stabilized composition of claim 1, wherein the composition further comprises at least one stability-enhancing salt.

6. The stabilized composition of claim 5, wherein the at least one stability-enhancing salt is selected from the group consisting of sodium chloride, potassium chloride, sodium phosphate, potassium phosphate, or a combination thereof.

7. The stabilized composition of claim 1, wherein the composition further comprises a pH modifier.

8. The stabilized composition of claim 7, wherein the pH modifier is sodium hydroxide or acetic acid.

9. The stabilized composition of claim 1, wherein the composition has a pH of from about 5 to about 7.

10. The stabilized composition of claim 1, wherein the composition further comprises a vehicle.

11. The stabilized composition of claim 10, wherein the vehicle is selected from the group consisting of water, saline, or phosphate-buffered saline.

12. The stabilized composition of claim 1, wherein the composition consists essentially of (i) caspofungin, or a polymorph, pharmaceutically acceptable salt, hydrate, or solvate thereof; and (ii) polyvinylpyrrolidone (PVP).

13. A method of preventing or treating a fungal infection in the pulmonary system of a subject in need thereof, comprising administering to the subject the composition of claim 1, wherein administration of the composition utilizing an inhalation delivery device provides a lung tissue concentration of caspofungin, or the polymorph, pharmaceutically acceptable salt, hydrate, or solvate thereof, that is from about 25-fold to about 100-fold greater than intravenous administration at the same delivery dose.

14. The method of claim 13, wherein the lung tissue concentration of caspofungin, or the polymorph, pharmaceutically acceptable salt, hydrate, or solvate thereof, administered utilizing the inhalation delivery device is greater than intravenous administration at the same delivery dose for about 0.5 hour to about 168 hours.

15. The method of claim 13, wherein administration of the composition provides a concentration of caspofungin, or the polymorph, pharmaceutically acceptable salt, hydrate, or solvate thereof, in the lung that is from about 5-fold greater to about 1000-fold greater than a concentration of caspofungin, or the polymorph, pharmaceutically acceptable salt, hydrate, or solvate thereof, in the liver, kidney, or plasma.

16. The method of claim 15, wherein the concentration of caspofungin, or the polymorph, pharmaceutically acceptable salt, hydrate, or solvate thereof, in the lung is greater than a concentration of caspofungin, or the polymorph, pharmaceutically acceptable salt, hydrate, or solvate thereof, in the liver, kidney, or plasma for about 0.5 hour to about 168 hours.

17. The method of claim 13, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 3 hours after administration.

18. The method of claim 17, wherein the concentration of caspofungin, or the polymorph, pharmaceutically acceptable salt, hydrate, or solvate thereof, in the lung is above the minimum inhibitory concentration (MIC) or the minimum effective concentration (MEC) for about 168 hours after administration.

19. The method of claim 17, wherein the minimum inhibitory concentration (MIC) or the minimum effective concentration (MEC) is from about 0.001 µg/mL to about 32 µg/mL.

20. The method of claim 13, wherein the half-life of the caspofungin, or a polymorph, pharmaceutically acceptable salt, hydrate, or solvate thereof, in the lung is about 24 hours to about 50 hours.

21. The method of claim 13, wherein the composition provides an increase of greater than about 50% of caspofungin, or a polymorph, pharmaceutically acceptable salt, hydrate, or solvate thereof, deposit in the lung without increasing systemic exposure when compared to a composition that does not comprise polyvinylpyrrolidone (PVP).

22. A method of preventing or treating a fungal infection in the pulmonary system of a subject in need thereof comprising administering to the subject a composition of claim 1.

23. The method of claim 22, wherein the method is for treating or preventing a fungal infection caused by *Candida* species, *Aspergillus* species, and/or *Pneumocystis jirovecii*.

* * * * *